(12) United States Patent
Paul, Jr. et al.

(10) Patent No.: US 11,724,073 B2
(45) Date of Patent: Aug. 15, 2023

(54) MRI COMPATIBLE INTERVENTIONAL WIREGUIDE

(71) Applicant: Cook Medical Technologies LLC, Bloomington, IN (US)

(72) Inventors: Ram H Paul, Jr., Bloomington, IN (US); Richard Swift, South Bend, IN (US); Shuo Yang, West Lafayette, IN (US); Tracy Willis, Bloomington, IN (US); Gary Neff, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 17/539,683

(22) Filed: Dec. 1, 2021

(65) Prior Publication Data

US 2022/0088353 A1    Mar. 24, 2022

Related U.S. Application Data

(63) Continuation of application No. 16/207,391, filed on Dec. 3, 2018, now Pat. No. 11,202,888.
(Continued)

(51) Int. Cl.
*A61B 5/00* (2006.01)
*A61M 25/09* (2006.01)
(Continued)

(52) U.S. Cl.
CPC ............ *A61M 25/09* (2013.01); *A61B 5/055* (2013.01); *G01R 33/285* (2013.01);
(Continued)

(58) Field of Classification Search
CPC combination set(s) only.
See application file for complete search history.

(56) References Cited

U.S. PATENT DOCUMENTS

| 5,346,473 A | 9/1994 | Bowman |
| 5,362,478 A | 11/1994 | Desai et al. |

(Continued)

FOREIGN PATENT DOCUMENTS

| AT | 312640 | 12/2005 |
| AU | 2002334881 | 4/2003 |

(Continued)

OTHER PUBLICATIONS

Carpenter Corporation. "Magnetic Properties of Stainless Steels," pp. 1-9. Retrieved from Internet May 3, 2018.
(Continued)

*Primary Examiner* — Joel F Brutus
(74) *Attorney, Agent, or Firm* — MacMillan, Sobanski & Todd, LLC

(57) ABSTRACT

The disclosure relates to medical devices and methods of assembling medical devices, such as MRI-compatible interventional wireguides. An example of a wireguide includes a series of individual segments, a plurality of connectors, and a plurality of spacers. Each segment in the series of individual segments has a first end and a second end. Each connector of the plurality of connectors joins adjacent segments in the series of individual segments to one another such that a first end of a first segment and a second end of a second segment in the series of individual segments are attached to a connector of the plurality of connectors. A spacer of the plurality of spacers is disposed between each pair of adjacent segments in the series of individual segments. Each of the segments in the series of individual segments is electrically insulated from an adjacent segment in the series of individual segments.

20 Claims, 26 Drawing Sheets

Related U.S. Application Data

(60) Provisional application No. 62/594,010, filed on Dec. 3, 2017.

(51) Int. Cl.
*G01R 33/36* (2006.01)
*G01R 33/28* (2006.01)
*A61B 5/055* (2006.01)

(52) U.S. Cl.
CPC ....... *G01R 33/286* (2013.01); *G01R 33/3685* (2013.01); *A61M 2025/09083* (2013.01); *A61M 2025/09133* (2013.01)

(56) References Cited

U.S. PATENT DOCUMENTS

| | | |
|---|---|---|
| 5,578,009 A | 11/1996 | Kraus et al. |
| 5,690,120 A | 11/1997 | Jacobsen et al. |
| 5,792,055 A | 8/1998 | McKinnon |
| 5,813,996 A | 9/1998 | St. Germain et al. |
| 5,833,632 A | 11/1998 | Jacobsen et al. |
| 5,853,375 A | 12/1998 | Orr |
| 5,897,536 A | 4/1999 | Nap et al. |
| 5,916,162 A | 6/1999 | Snelten et al. |
| 5,951,494 A | 9/1999 | Wang et al. |
| 6,017,319 A | 1/2000 | Jacobsen et al. |
| 6,019,737 A | 2/2000 | Murata |
| 6,394,976 B1 | 5/2002 | Winston et al. |
| 6,451,026 B1 | 9/2002 | Biagtan et al. |
| 6,458,088 B1 | 10/2002 | Hurtak et al. |
| 6,574,497 B1 | 6/2003 | Pacetti |
| 6,612,998 B2 | 9/2003 | Gosiengfiao et al. |
| 6,675,033 B1 | 1/2004 | Lardo et al. |
| 6,687,533 B1 | 2/2004 | Hirano et al. |
| 6,714,809 B2 | 3/2004 | Lee et al. |
| 6,772,000 B2 | 8/2004 | Talpade |
| 6,799,067 B2 | 9/2004 | Pacetti et al. |
| 6,845,259 B2 | 1/2005 | Pacetti et al. |
| 6,911,016 B2 | 6/2005 | Balzum et al. |
| 6,918,882 B2 | 7/2005 | Skujins et al. |
| 6,975,896 B2 | 12/2005 | Ehnholm et al. |
| 7,074,197 B2 | 7/2006 | Reynolds et al. |
| 7,169,118 B2 | 1/2007 | Reynolds et al. |
| 7,182,735 B2 | 2/2007 | Shireman et al. |
| 7,278,973 B2 | 10/2007 | Iwami et al. |
| 7,507,211 B2 | 3/2009 | Pacetti et al. |
| 7,540,845 B2 | 6/2009 | Parins |
| 7,553,287 B2 | 6/2009 | Reynolds et al. |
| 7,596,402 B2 | 9/2009 | Duerk et al. |
| 7,618,379 B2 | 11/2009 | Reynolds et al. |
| 7,641,621 B2 | 1/2010 | Crank |
| 7,651,578 B2 | 1/2010 | Sharrow et al. |
| 7,747,314 B2 | 6/2010 | Parins et al. |
| 7,758,520 B2 | 7/2010 | Griffin et al. |
| 7,761,138 B2 | 7/2010 | Wang et al. |
| 7,785,273 B2 | 8/2010 | Eskuri |
| 7,789,906 B2 | 9/2010 | Blank |
| 7,792,568 B2 | 9/2010 | Zhong et al. |
| 7,833,175 B2 | 11/2010 | Parins |
| 7,841,994 B2 | 11/2010 | Skujins et al. |
| 7,943,161 B2 | 5/2011 | Carlgren et al. |
| 7,993,286 B2 | 8/2011 | Reynolds et al. |
| 8,002,715 B2 | 8/2011 | Shireman |
| 8,021,311 B2 | 9/2011 | Munoz et al. |
| 8,067,073 B2 | 11/2011 | Zhong et al. |
| 8,070,693 B2 | 12/2011 | Ayala et al. |
| 8,082,021 B2 | 12/2011 | Hyde et al. |
| 8,137,292 B2 | 3/2012 | Skujins et al. |
| 8,137,293 B2 | 3/2012 | Zhou et al. |
| 8,163,326 B2 | 4/2012 | Zhong et al. |
| 8,167,821 B2 | 5/2012 | Sharrow |
| 8,292,828 B2 | 10/2012 | Uihlein |
| 8,376,961 B2 | 2/2013 | Layman et al. |
| 8,409,114 B2 | 4/2013 | Parins |
| 8,414,506 B2 | 4/2013 | Reynolds et al. |
| 8,419,658 B2 | 4/2013 | Eskur |
| 8,478,381 B2 | 7/2013 | Kocaturk |
| 8,485,992 B2 | 7/2013 | Griffin et al. |
| 8,529,872 B2 | 9/2013 | Frank et al. |
| 8,535,243 B2 | 9/2013 | Shireman |
| 8,551,020 B2 | 10/2013 | Chen et al. |
| 8,551,021 B2 | 10/2013 | Voeller et al. |
| 8,556,914 B2 | 10/2013 | Vrba |
| 8,620,406 B2 | 12/2013 | Smith et al. |
| 8,728,010 B2 | 5/2014 | Hirshman |
| 8,795,202 B2 | 8/2014 | Northorp et al. |
| 8,795,254 B2 | 8/2014 | Layman et al. |
| 8,846,006 B2 | 9/2014 | Frank et al. |
| 9,038,639 B2 | 5/2015 | Pfeffer et al. |
| 9,072,874 B2 | 7/2015 | Northrop et al. |
| 9,138,561 B2 | 9/2015 | Stenzel et al. |
| 9,192,743 B2 | 11/2015 | Stenzel et al. |
| 9,227,037 B2 | 1/2016 | Northrop |
| 9,383,421 B2 | 7/2016 | Vij |
| 9,656,004 B2 | 5/2017 | Duering et al. |
| 9,775,523 B2 | 10/2017 | Gregorich |
| 10,028,666 B2 | 1/2018 | Gregorich |
| 10,035,002 B2 | 7/2018 | Weiss |
| 10,065,023 B2 | 9/2018 | Sela |
| 2003/0055332 A1 | 3/2003 | Daum et al. |
| 2003/0055449 A1 | 3/2003 | Lee et al. |
| 2003/0060731 A1 | 3/2003 | Fleischhacker |
| 2003/0069520 A1 | 4/2003 | Skujins et al. |
| 2003/0069521 A1 | 4/2003 | Reynolds et al. |
| 2003/0120148 A1 | 6/2003 | Pacetti |
| 2003/0135114 A1 | 7/2003 | Pacetti et al. |
| 2003/0208142 A1 | 11/2003 | Boudewijn et al. |
| 2004/0143180 A1 | 7/2004 | Zhong et al. |
| 2004/0167437 A1 | 8/2004 | Sharrow et al. |
| 2004/0167438 A1 | 8/2004 | Sharrow |
| 2004/0167439 A1 | 8/2004 | Sharrow |
| 2004/0254450 A1 | 12/2004 | Griffin et al. |
| 2005/0054952 A1 | 3/2005 | Eskuri et al. |
| 2005/0065437 A1 | 3/2005 | Weber et al. |
| 2005/0070793 A1 | 3/2005 | Pacetti et al. |
| 2005/0096665 A1 | 5/2005 | Reynolds et al. |
| 2005/0119615 A1 | 6/2005 | Noriega et al. |
| 2005/0148865 A1 | 7/2005 | Weber |
| 2006/0122537 A1 | 6/2006 | Reynolds et al. |
| 2007/0016131 A1 | 1/2007 | Munger et al. |
| 2007/0060878 A1 | 3/2007 | Bonnette et al. |
| 2007/0083132 A1 | 4/2007 | Sharrow |
| 2007/0135734 A1 | 6/2007 | Reynolds et al. |
| 2007/0162108 A1 | 7/2007 | Carlson et al. |
| 2007/0244414 A1 | 10/2007 | Reynolds et al. |
| 2007/0280850 A1 | 12/2007 | Carlson |
| 2008/0045908 A1 | 2/2008 | Gould et al. |
| 2008/0097294 A1 | 4/2008 | Prather et al. |
| 2008/0125674 A1 | 5/2008 | Bilecen et al. |
| 2008/0262474 A1 | 10/2008 | Northrop |
| 2008/0312597 A1 | 12/2008 | Uihlein |
| 2009/0036832 A1 | 2/2009 | Skujins et al. |
| 2009/0118675 A1 | 5/2009 | Czyscon et al. |
| 2009/0118704 A1 | 5/2009 | Sharrow et al. |
| 2009/0177119 A1 | 7/2009 | Heidner et al. |
| 2009/0227901 A1 | 9/2009 | Hofmann |
| 2009/0292225 A1 | 11/2009 | Chen et al. |
| 2010/0063479 A1 | 3/2010 | Merdan et al. |
| 2010/0254897 A1 | 10/2010 | Frank et al. |
| 2011/0166439 A1 | 7/2011 | Pfeffer et al. |
| 2011/0270169 A1 | 11/2011 | Gardeski et al. |
| 2012/0053572 A1 | 3/2012 | Rusu et al. |
| 2013/0030362 A1 | 1/2013 | Wright et al. |
| 2013/0085444 A1 | 4/2013 | Heinrich |
| 2013/0123692 A1 | 5/2013 | Zhang et al. |
| 2013/0158478 A1 | 6/2013 | Kaufmann et al. |
| 2013/0274591 A1 | 10/2013 | Sonmez et al. |
| 2013/0274618 A1 | 10/2013 | Hou et al. |
| 2013/0324837 A1 | 12/2013 | Meyer et al. |
| 2014/0005558 A1 | 1/2014 | Gregorich |
| 2014/0058275 A1 | 2/2014 | Gregorich et al. |
| 2014/0081244 A1 | 3/2014 | Voeller et al. |
| 2014/0121642 A1 | 5/2014 | Jordan et al. |
| 2014/0243615 A1 | 8/2014 | Schaeffer et al. |

(56) References Cited

U.S. PATENT DOCUMENTS

| | | |
|---|---|---|
| 2014/0243742 A1 | 8/2014 | Pacheco et al. |
| 2014/0350414 A1 | 11/2014 | McGowan et al. |
| 2015/0051696 A1 | 2/2015 | Hou et al. |
| 2015/0073391 A1 | 3/2015 | Hutchins et al. |
| 2015/0148706 A1 | 5/2015 | Abner |
| 2015/0151081 A1 | 6/2015 | Keith et al. |
| 2015/0182671 A1 | 7/2015 | Duering |
| 2015/0190614 A1 | 7/2015 | Uihlein |
| 2015/0265167 A1 | 9/2015 | McGowan et al. |
| 2015/0338477 A1 | 11/2015 | Schmidt et al. |
| 2015/0351644 A1 | 12/2015 | Lee et al. |
| 2016/0008584 A1 | 1/2016 | Root et al. |
| 2016/0051798 A1 | 2/2016 | Weber et al. |
| 2016/0082228 A1 | 3/2016 | Sela |
| 2016/0089515 A1 | 3/2016 | Hansen et al. |
| 2017/0055908 A1 | 3/2017 | Radman et al. |
| 2017/0106171 A1 | 4/2017 | Flores et al. |
| 2017/0202480 A1 | 7/2017 | Kim et al. |
| 2017/0232158 A1 | 8/2017 | Düring et al. |
| 2017/0239450 A1 * | 8/2017 | Kocaturk .............. A61M 25/09 |
| 2017/0291013 A1 | 10/2017 | Pereira et al. |
| 2018/0078742 A1 | 3/2018 | Butler et al. |
| 2018/0161121 A1 | 6/2018 | Butler et al. |
| 2018/0185618 A1 | 7/2018 | Sweeney |
| 2018/0193606 A1 | 7/2018 | Patel et al. |
| 2018/0193608 A1 | 7/2018 | Bodewadt et al. |
| 2018/0243530 A1 | 8/2018 | Lederman et al. |

FOREIGN PATENT DOCUMENTS

| | | |
|---|---|---|
| AU | 2002358281 | 7/2003 |
| CA | 2462335 | 4/2003 |
| CN | 2930741 | 8/2007 |
| DE | 19843427 | 3/2000 |
| DE | 20019484 | 5/2001 |
| DE | 10029738 | 1/2002 |
| DE | 20017836 | 2/2002 |
| DE | 1 0243261 | 3/2004 |
| DE | 60208057 | 6/2006 |
| DE | 102005022688 | 11/2006 |
| DE | 202010004107 U1 | 7/2010 |
| DE | 202010016473 U1 | 2/2012 |
| DE | 102011101680 A1 | 9/2012 |
| DE | 102011081445 | 2/2013 |
| EP | 0744186 | 11/1996 |
| EP | 0775500 | 5/1997 |
| EP | 1432467 | 12/2005 |
| EP | 1596894 | 6/2006 |
| EP | 1011491 | 1/2007 |
| EP | 1242138 | 5/2007 |
| EP | 1551490 | 5/2007 |
| EP | 1819374 | 8/2012 |
| EP | 2675353 | 12/2013 |
| EP | WO2016064753 | 4/2016 |
| EP | 3093037 | 11/2016 |
| EP | 2508213 | 3/2018 |
| EP | 3288629 | 3/2018 |
| EP | 3349650 | 7/2018 |
| JP | 1998290839 | 11/1998 |
| JP | 2005528126 | 9/2005 |
| JP | 3962724 | 8/2007 |
| JP | 2009183765 | 8/2009 |
| JP | 4494782 | 6/2010 |
| NL | 1006612 | 1/1999 |
| WO | WO199842268 | 10/1998 |
| WO | WO9855016 | 12/1998 |
| WO | WO20000064003 | 1/2001 |
| WO | WO0195794 | 12/2001 |
| WO | WO200303982 | 7/2003 |
| WO | WO2003057302 | 7/2003 |
| WO | WO2003092791 | 11/2003 |
| WO | WO2006036786 | 6/2006 |
| WO | WO2006116538 | 11/2006 |
| WO | WO2006119645 | 11/2006 |
| WO | WO2012032881 | 3/2012 |
| WO | WO2017048759 | 3/2017 |

OTHER PUBLICATIONS

Basar et al. "Segmented nitinol guidewires with stiffness-matched connectors for cardiovascular magnetic resonance catheterization: preserved mechanical performance and freedom from heating," J. Cardiovascular Magnetic Resonance (2015) 17:105. Published Nov. 30, 2015.

European Patent Office. "Supplementary European Search Report" for EP application No. 01942159, completed Feb. 2, 2006.

International Searching Authority. International Search Report and Written Opinion for international application No. PCT/US2018/063562, dated Sep. 26, 2019, pp. 1-10.

European Communication pursuant to Article 94(3), Application No. 18 829 568.7, dated Mar. 24, 2022.

\* cited by examiner

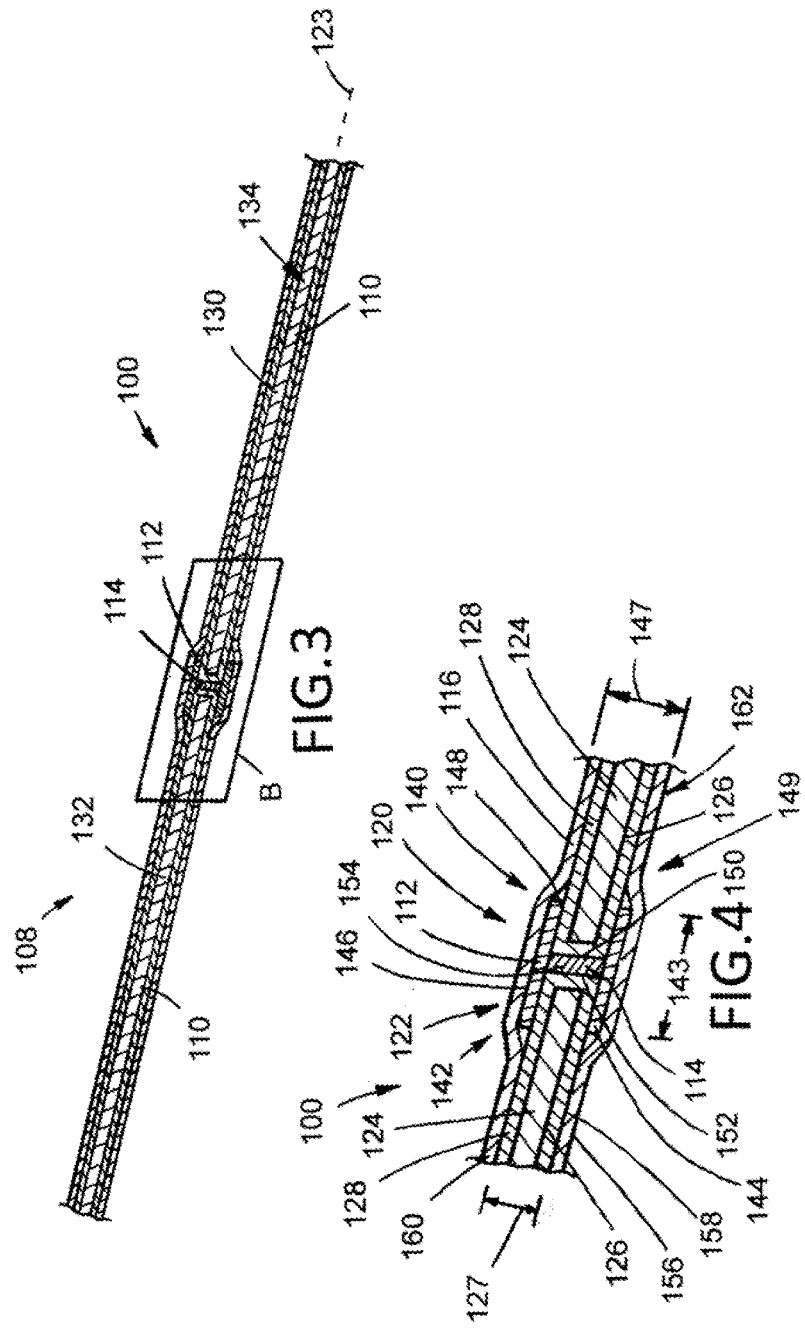

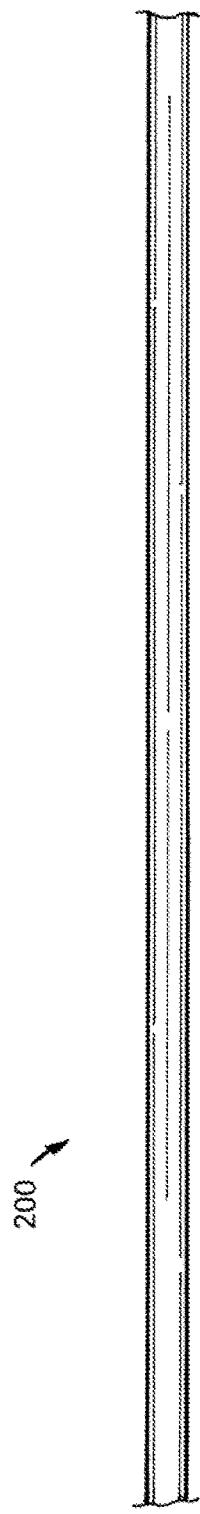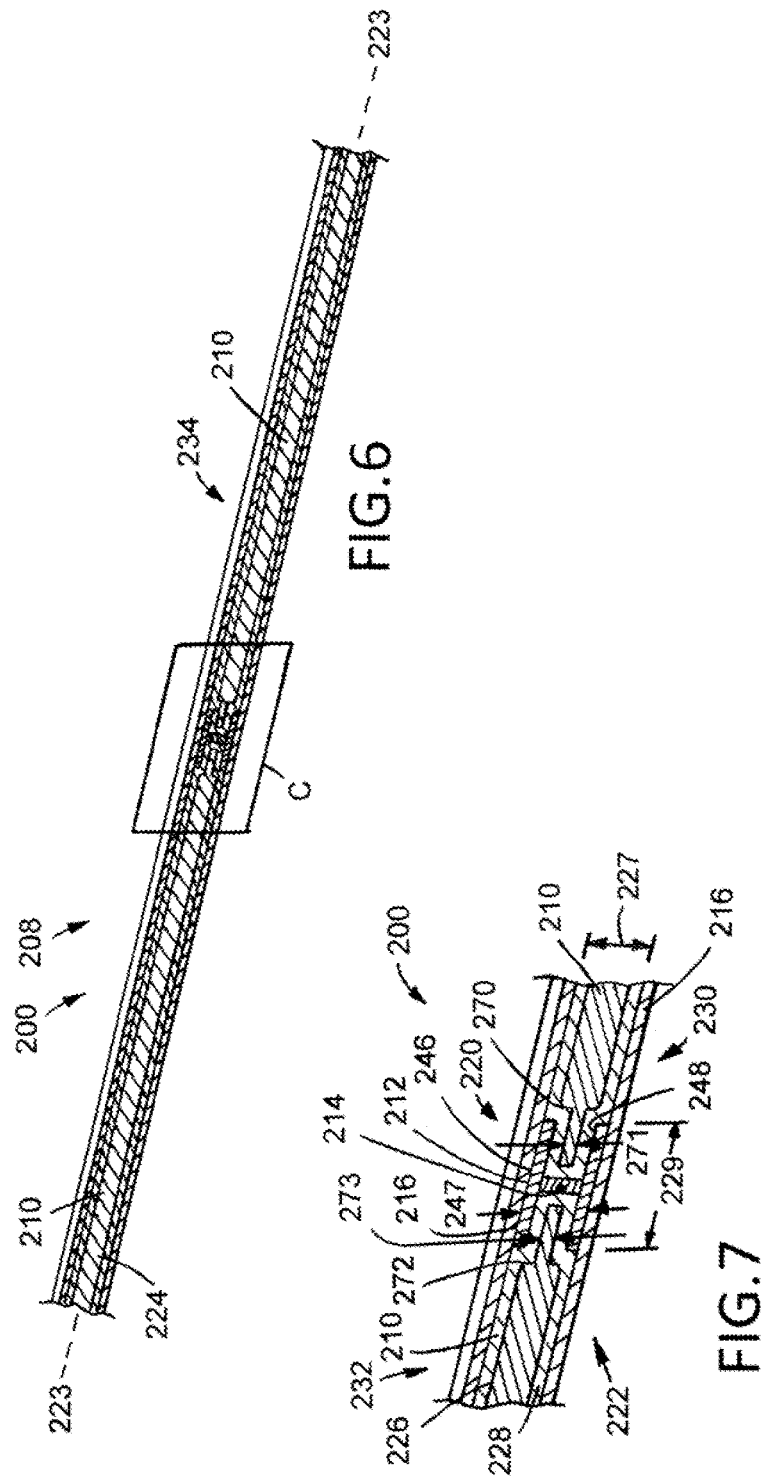

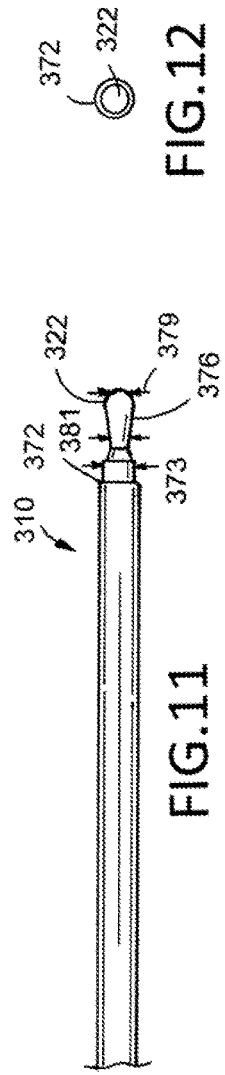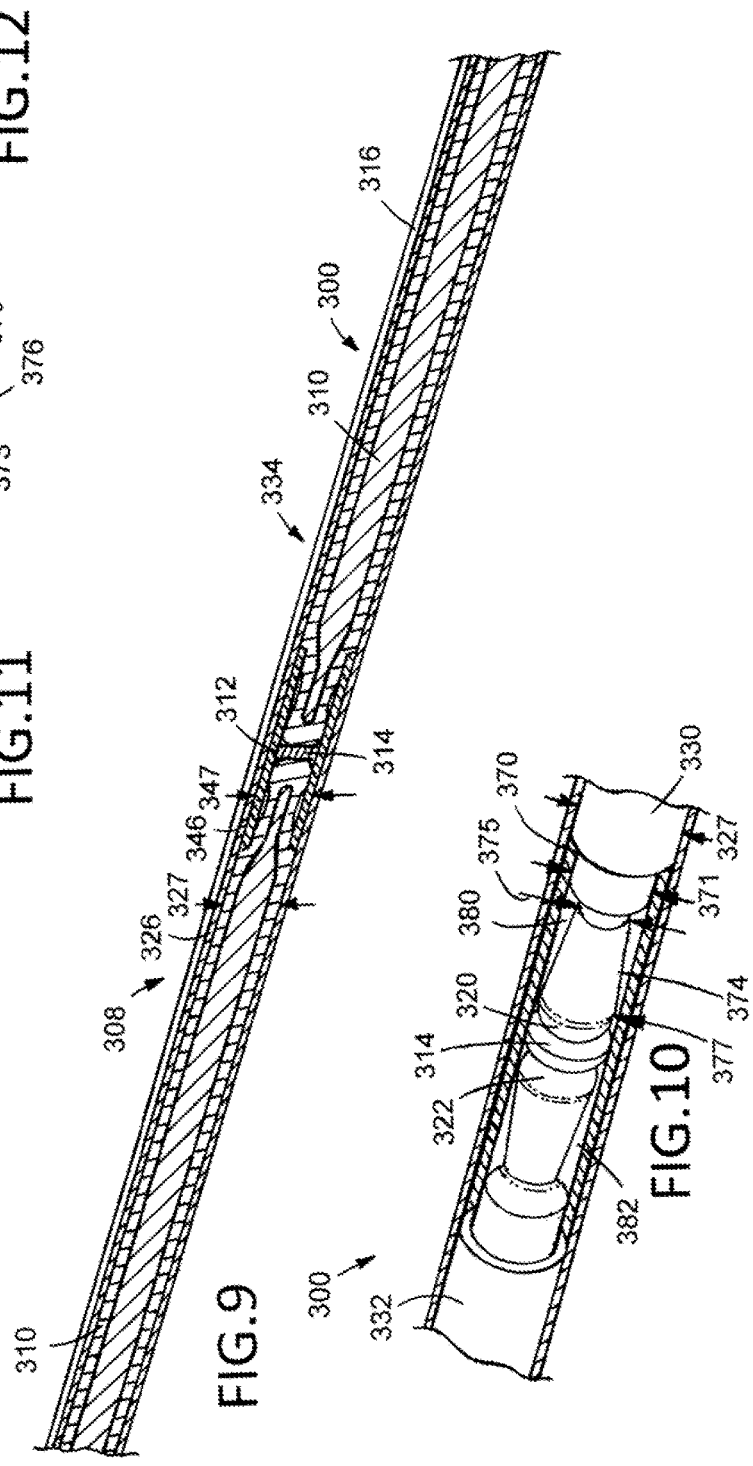

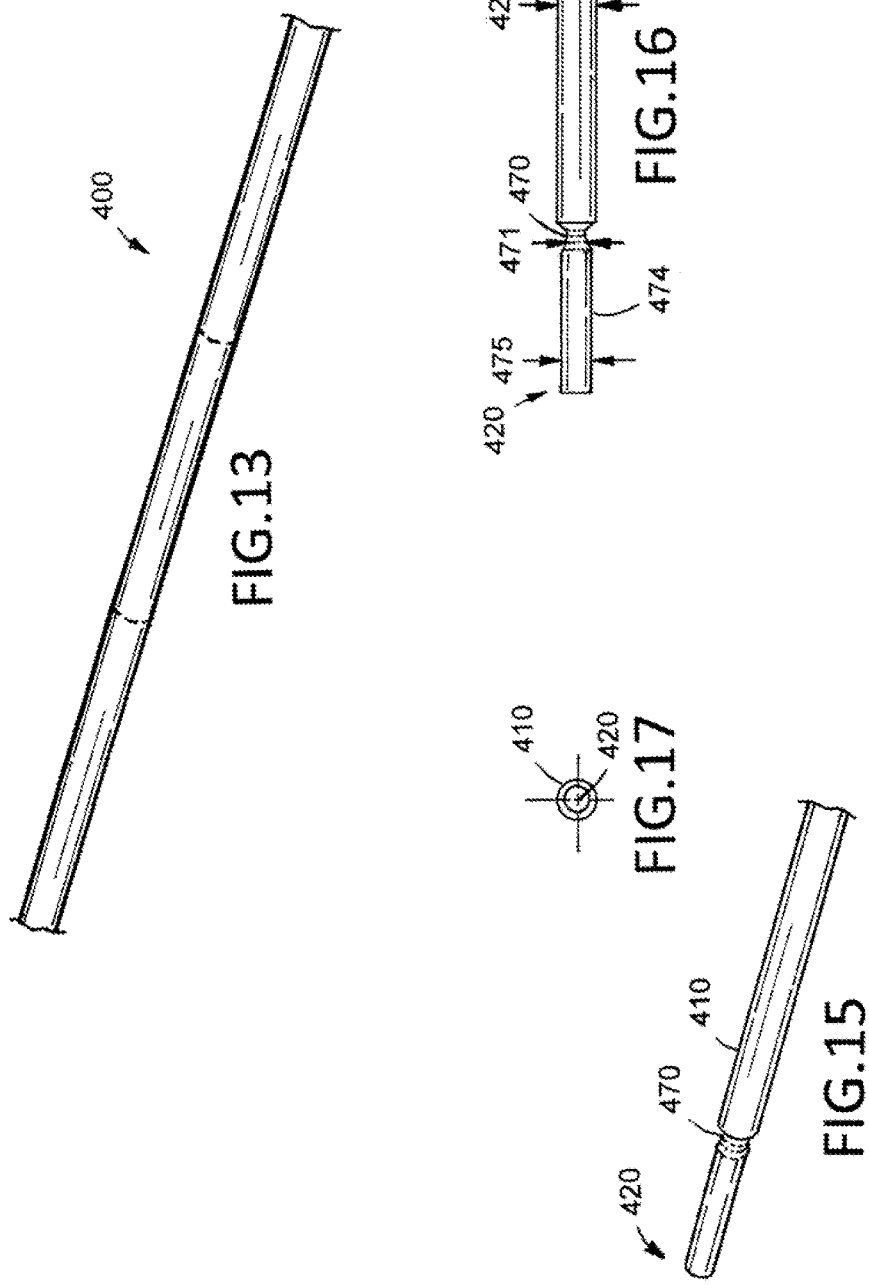

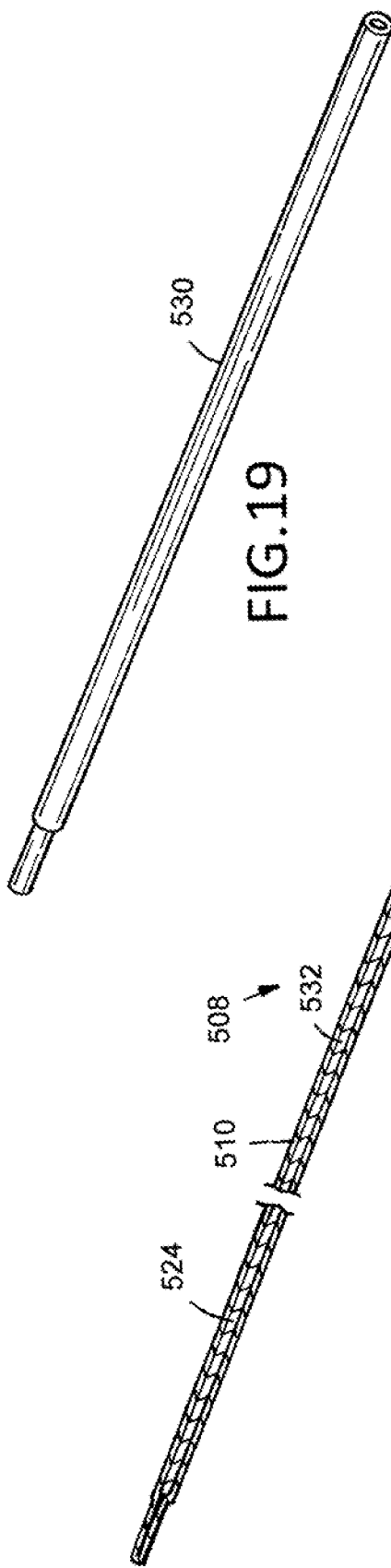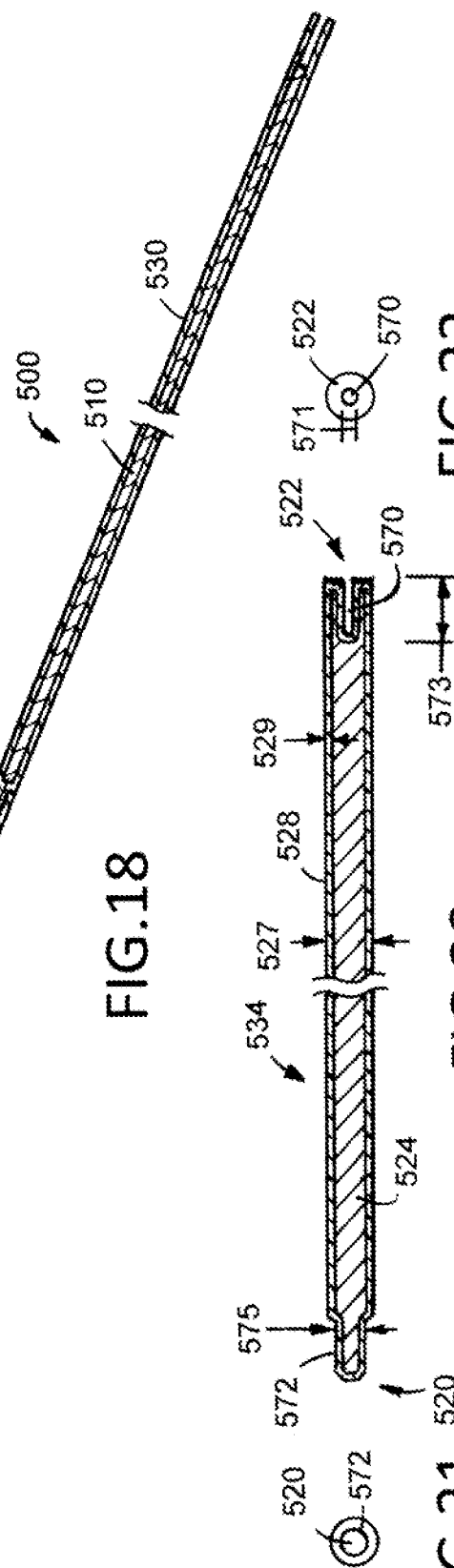

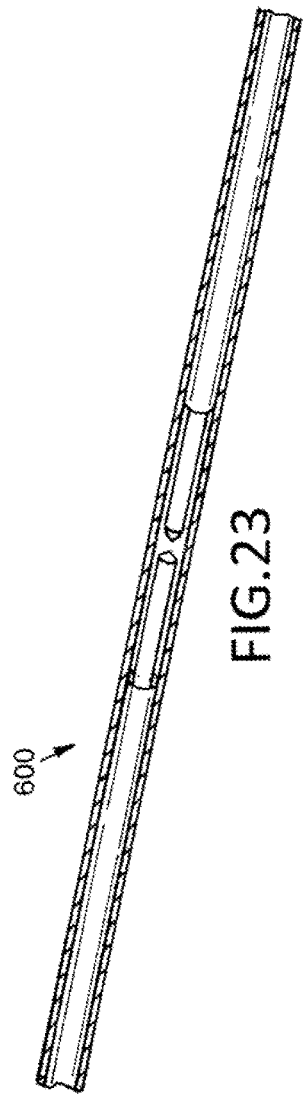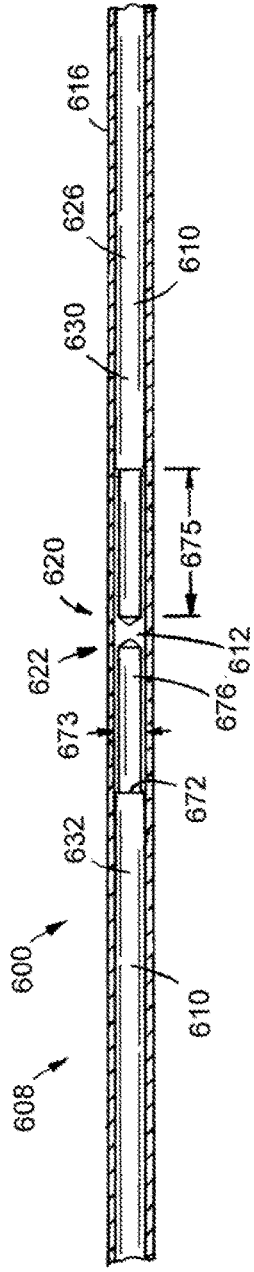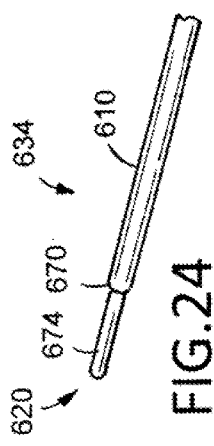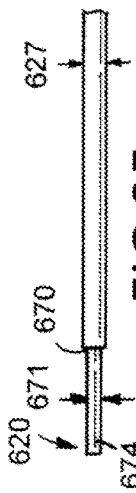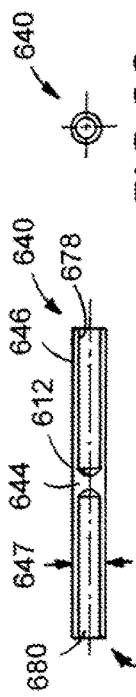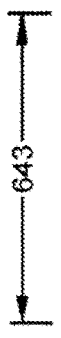

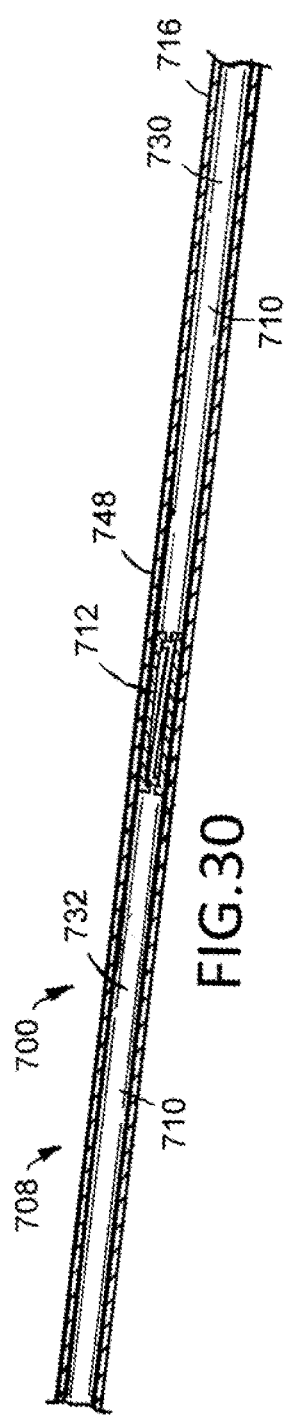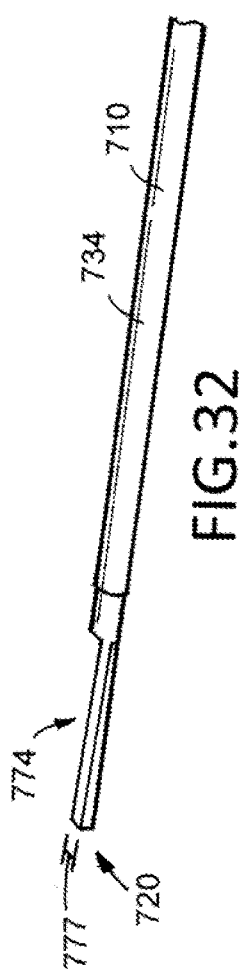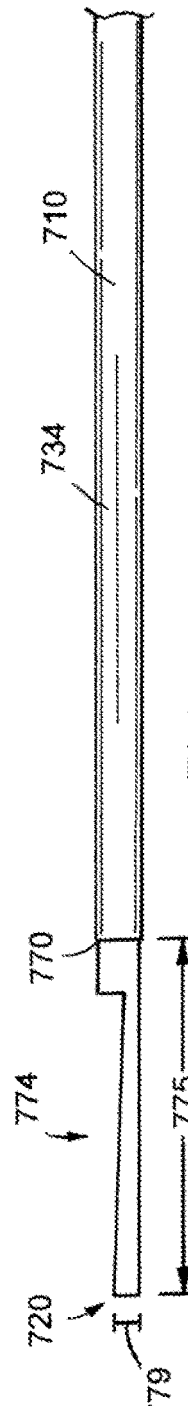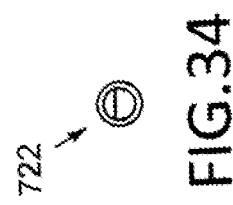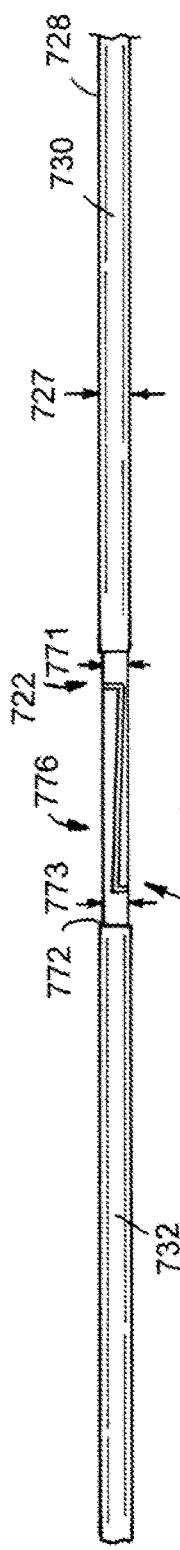

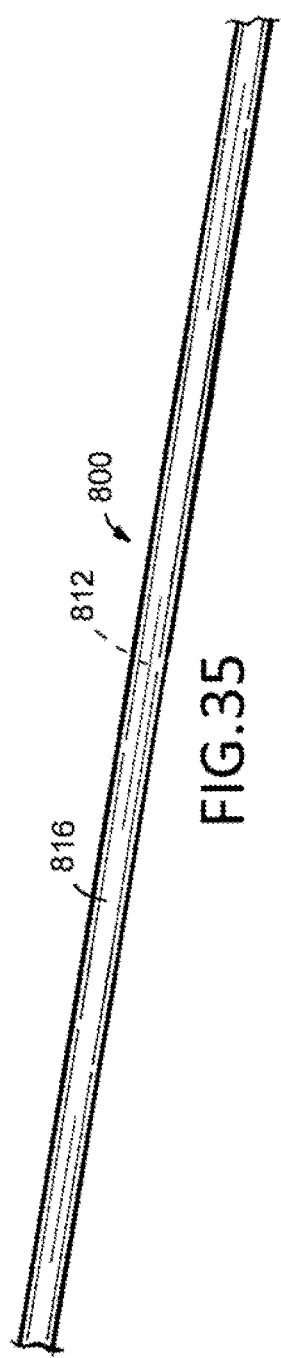
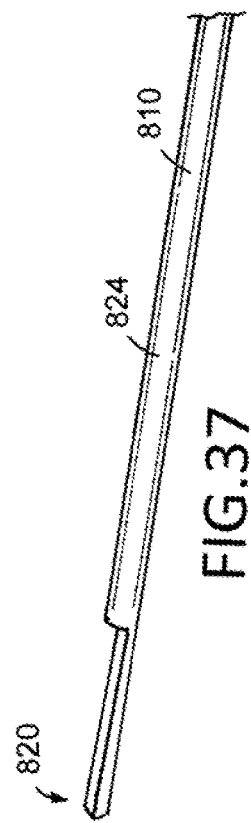
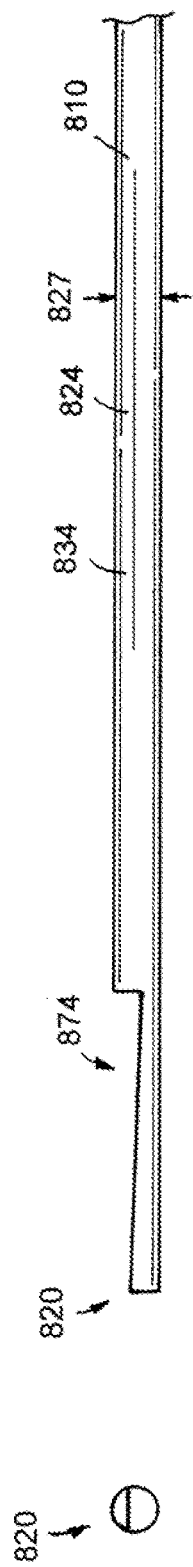
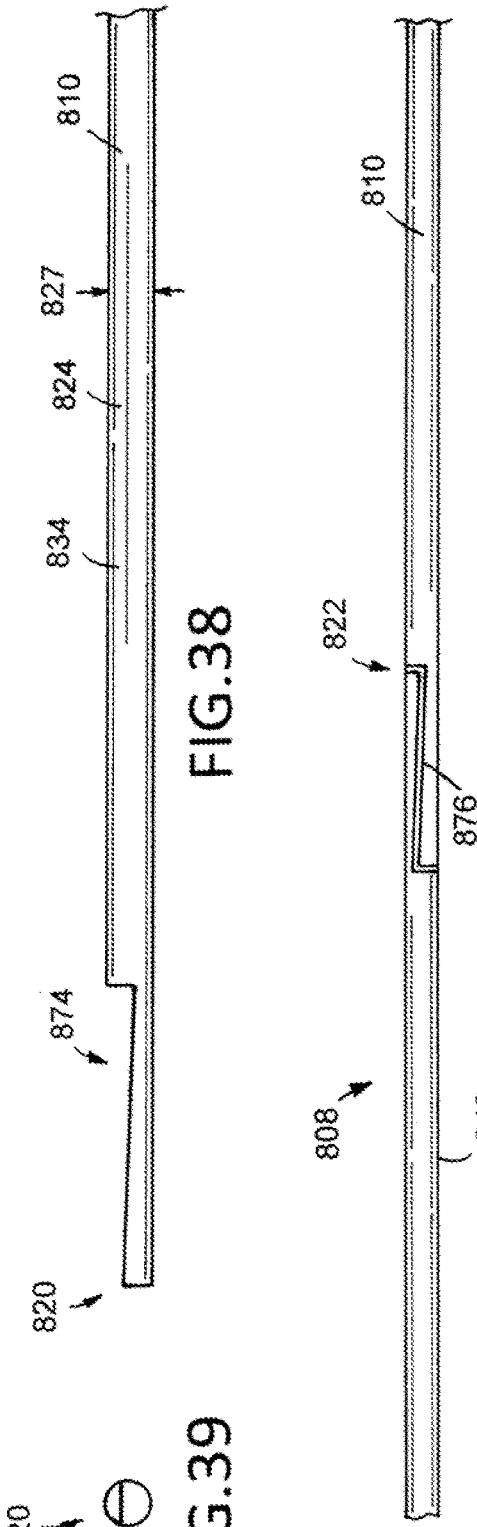

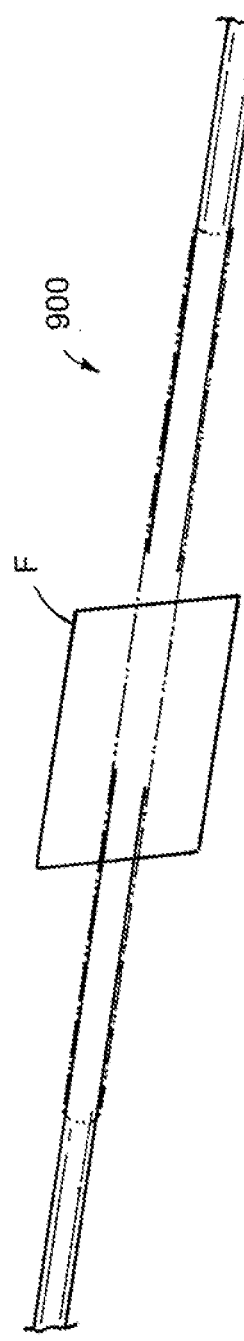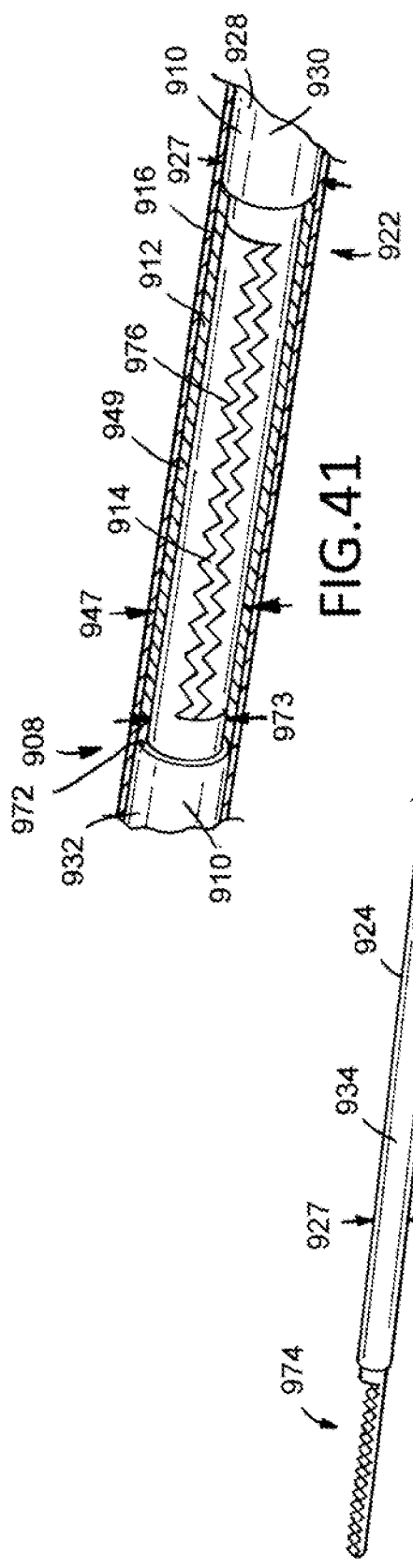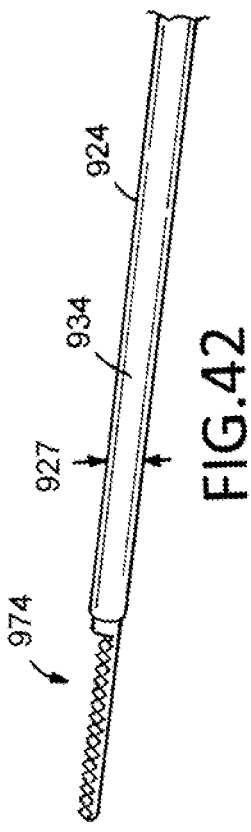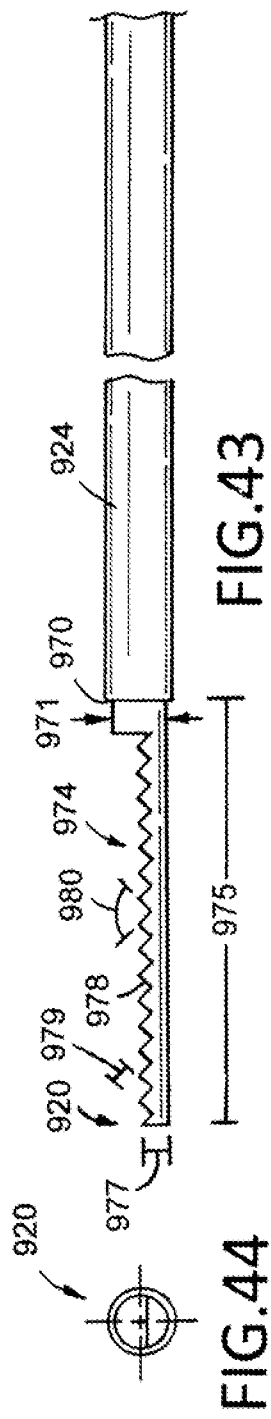

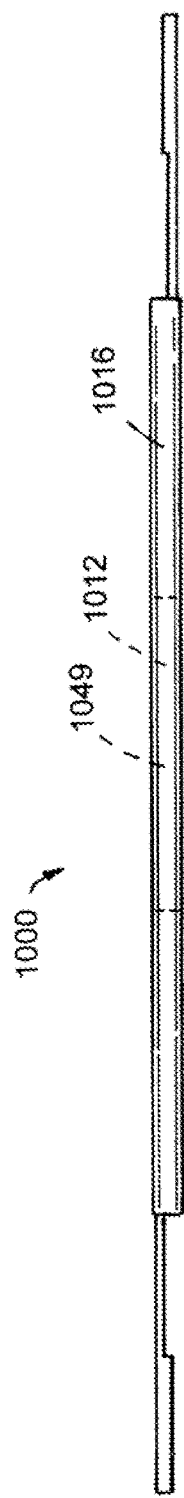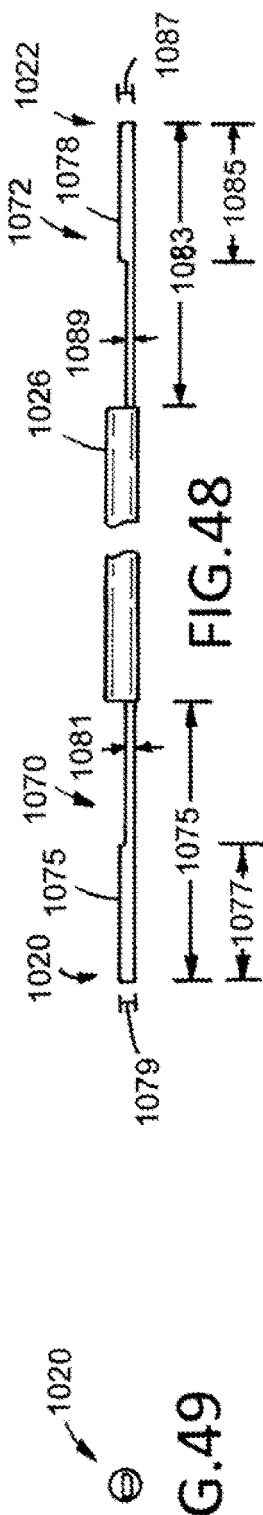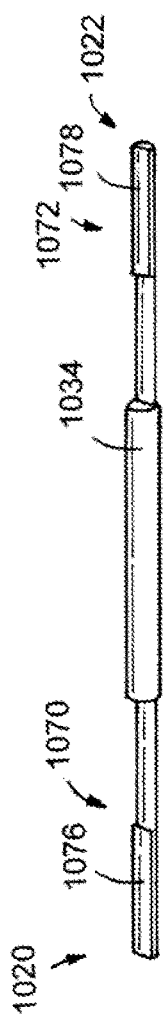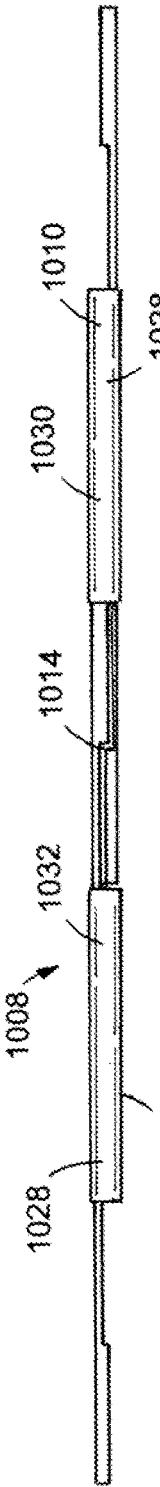

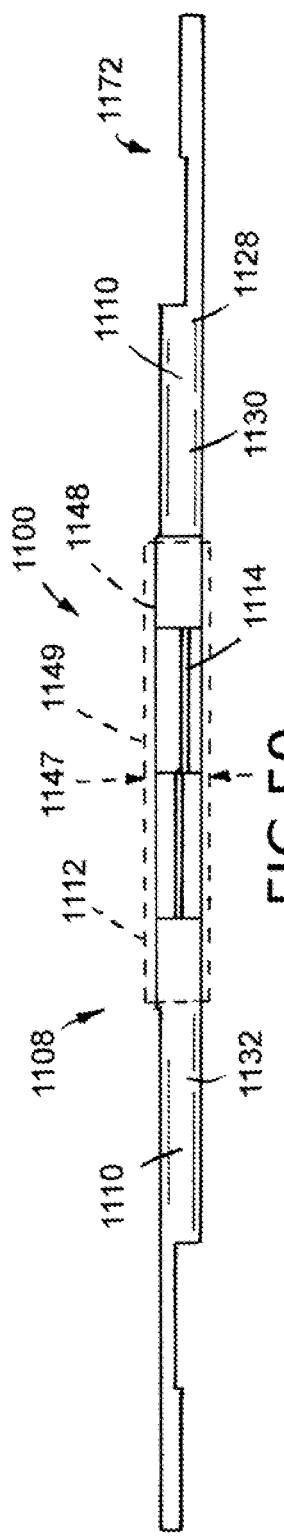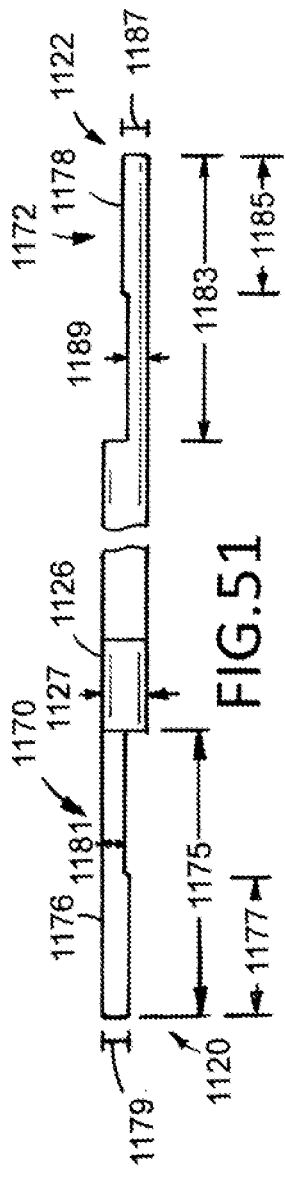

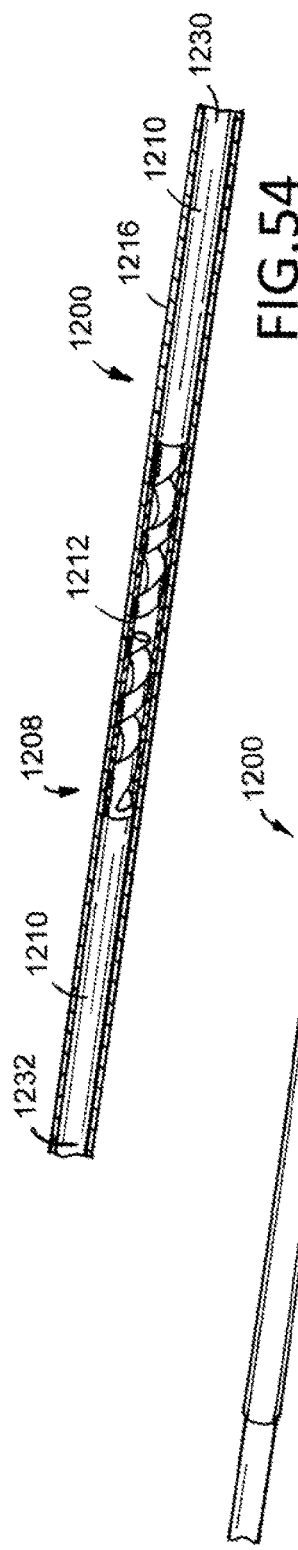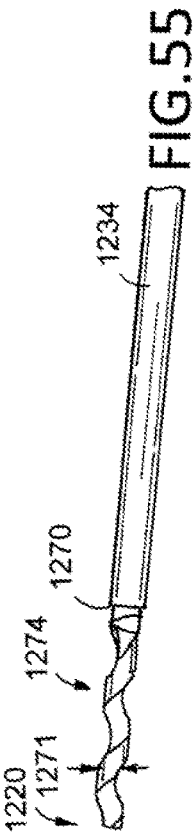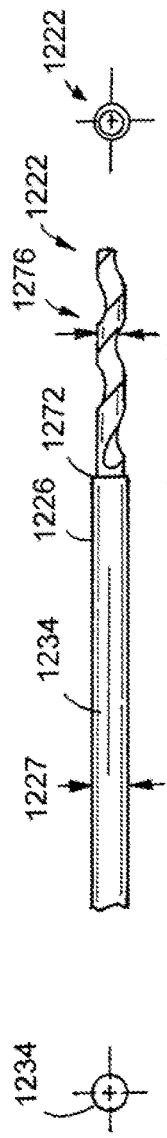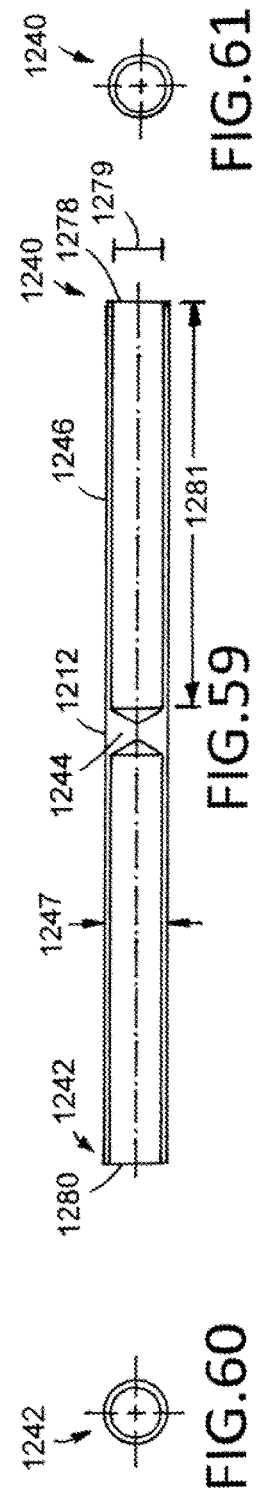

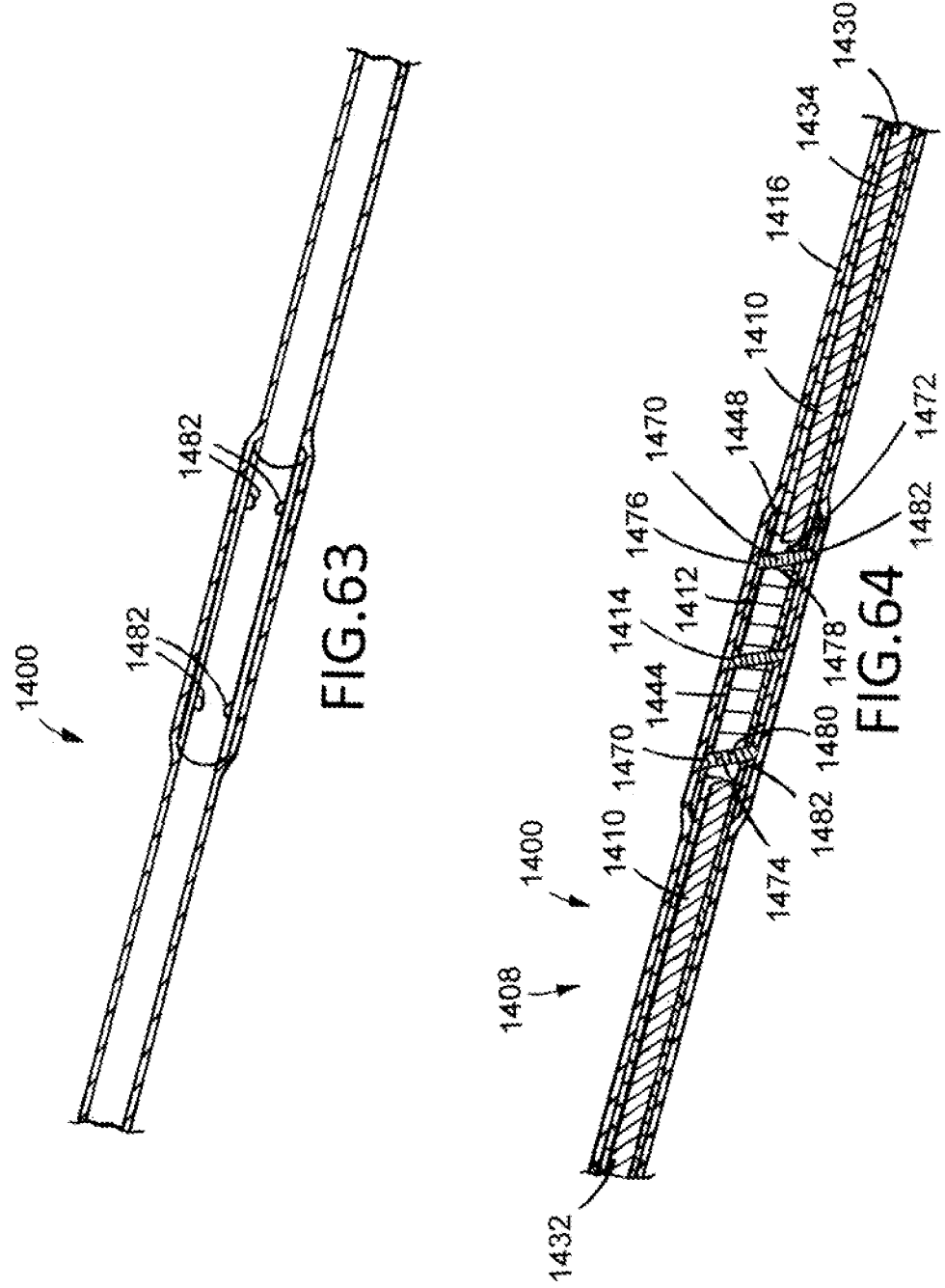

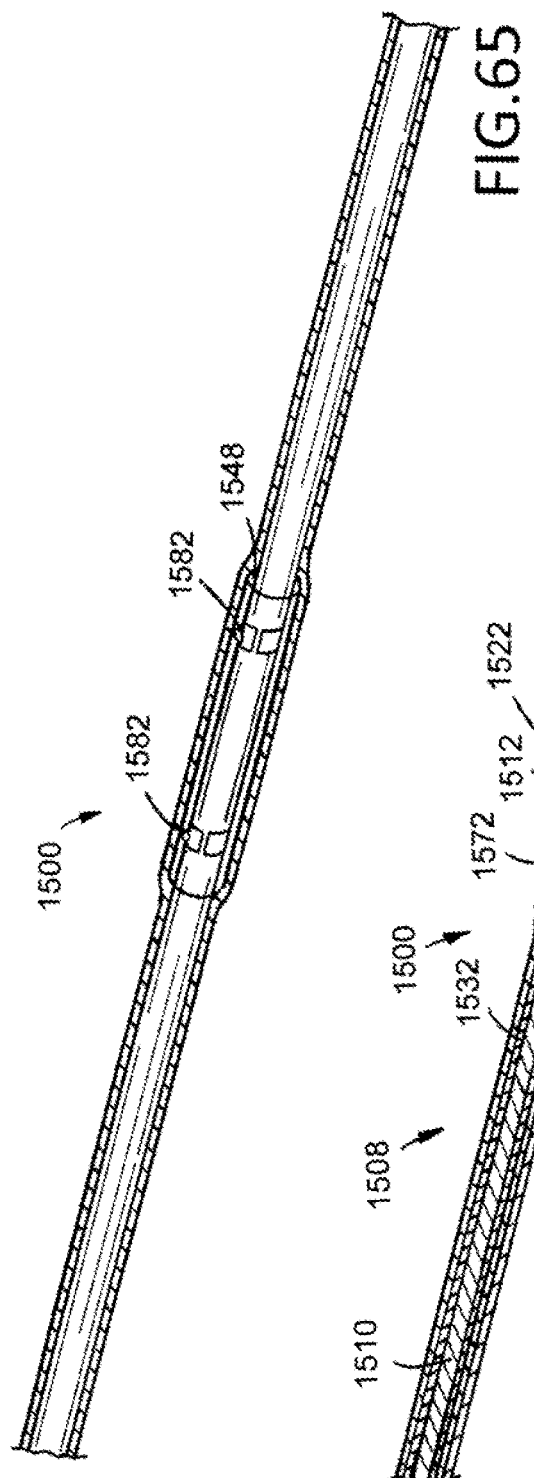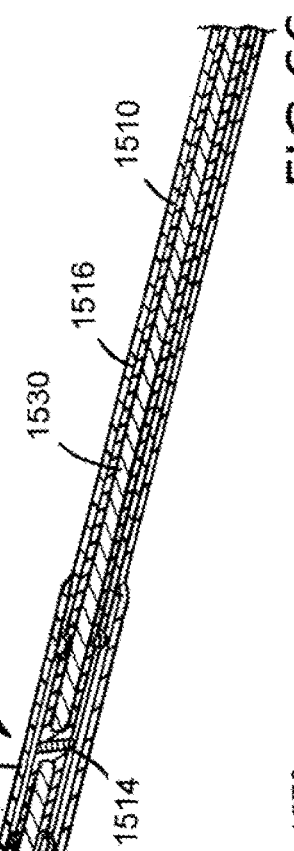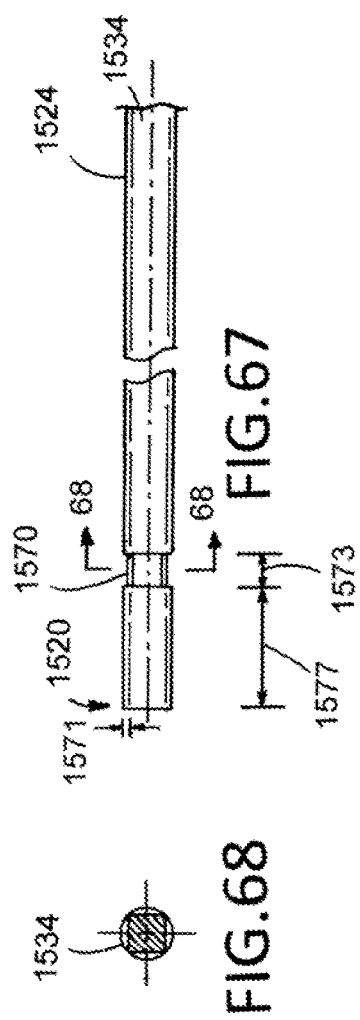

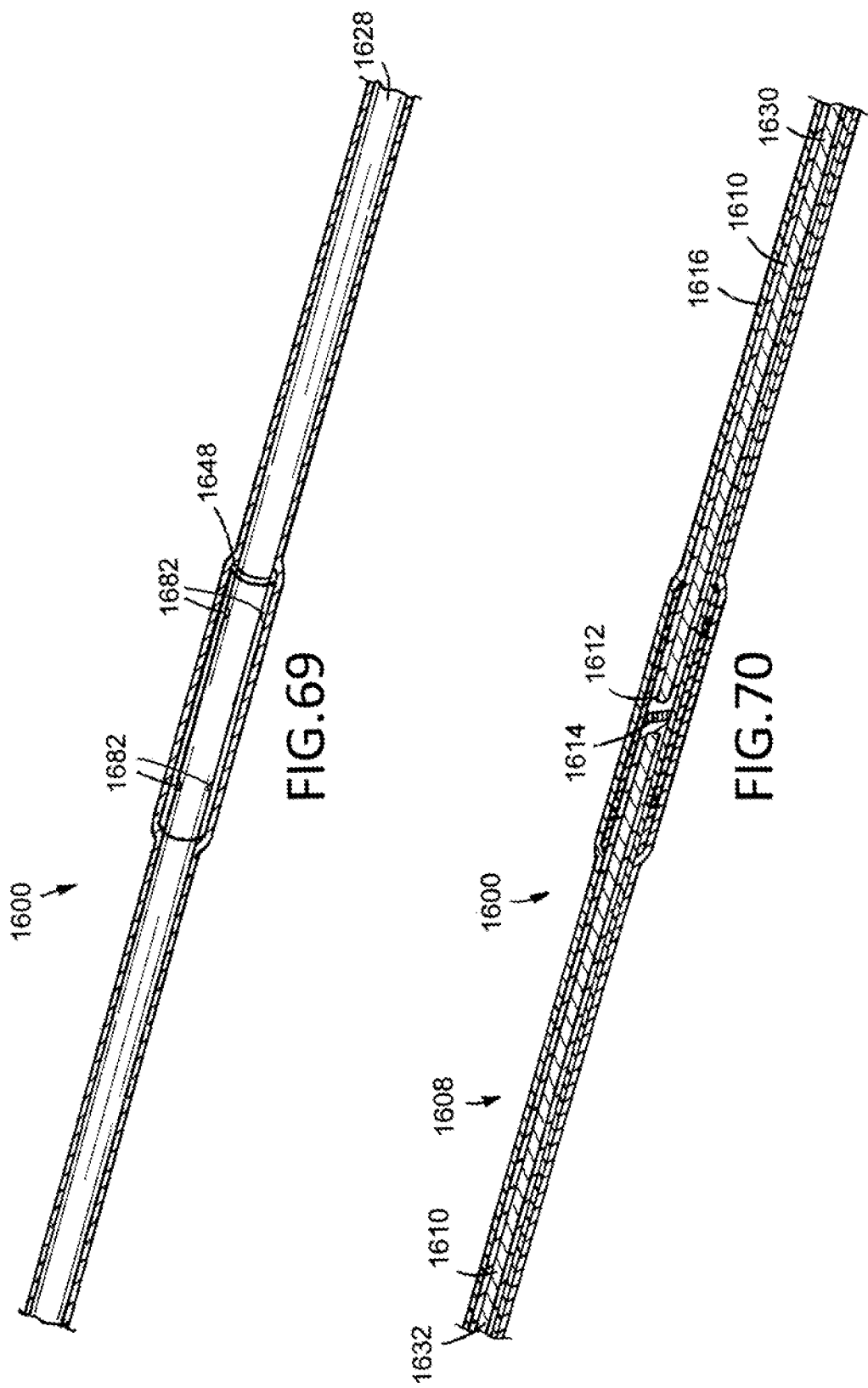

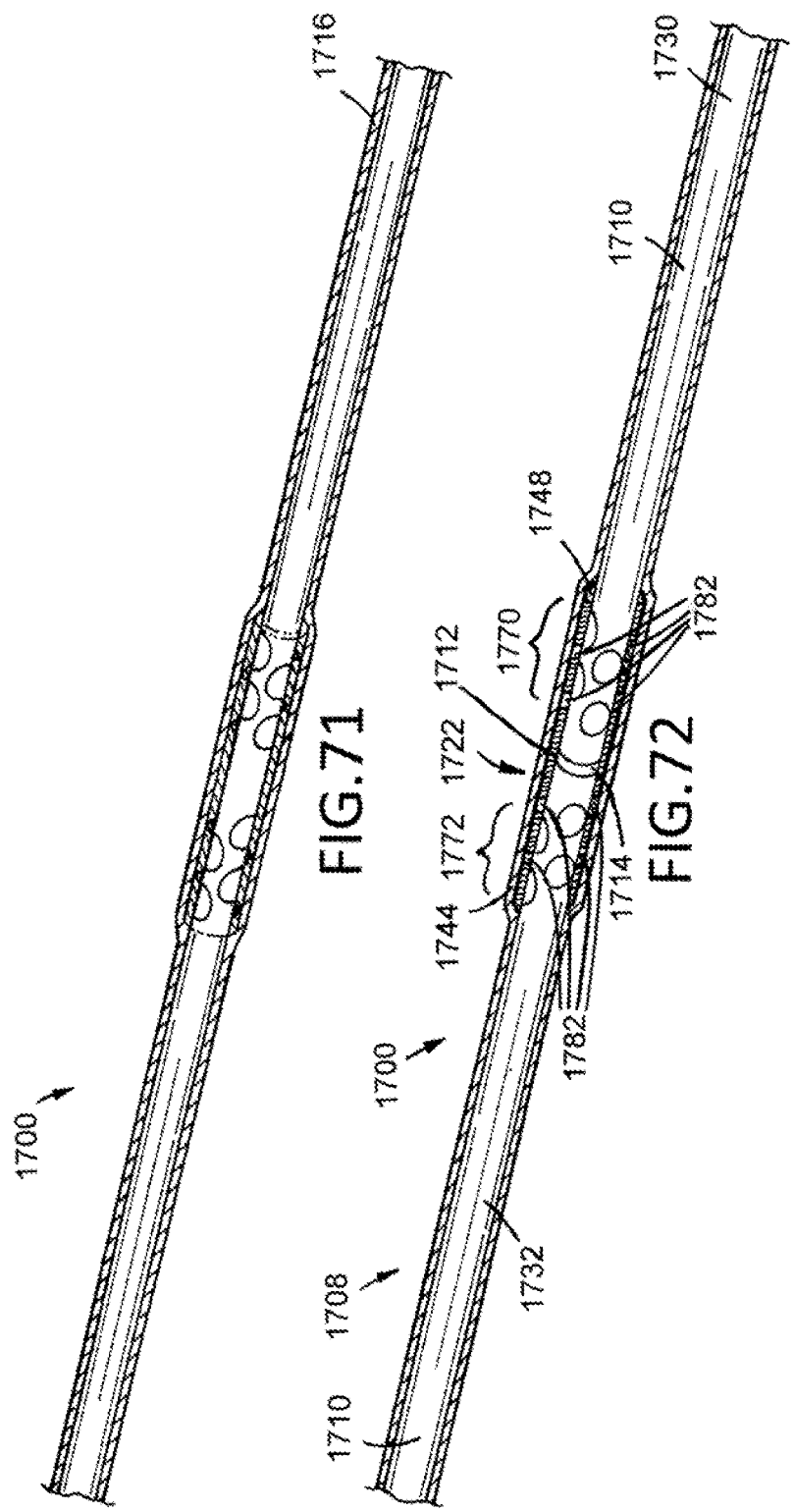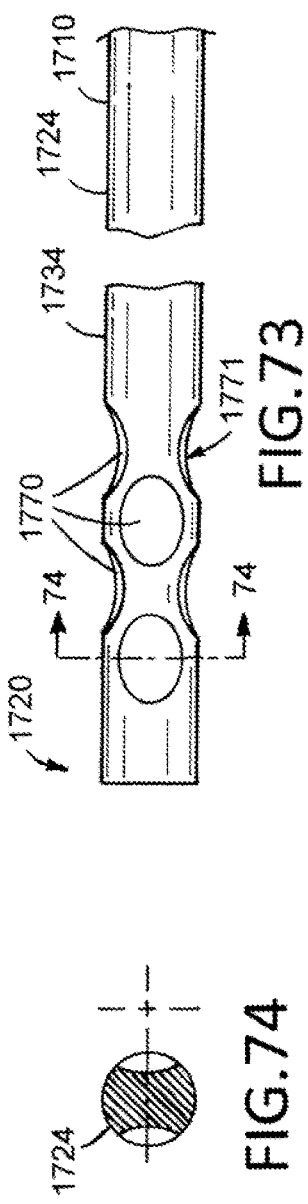

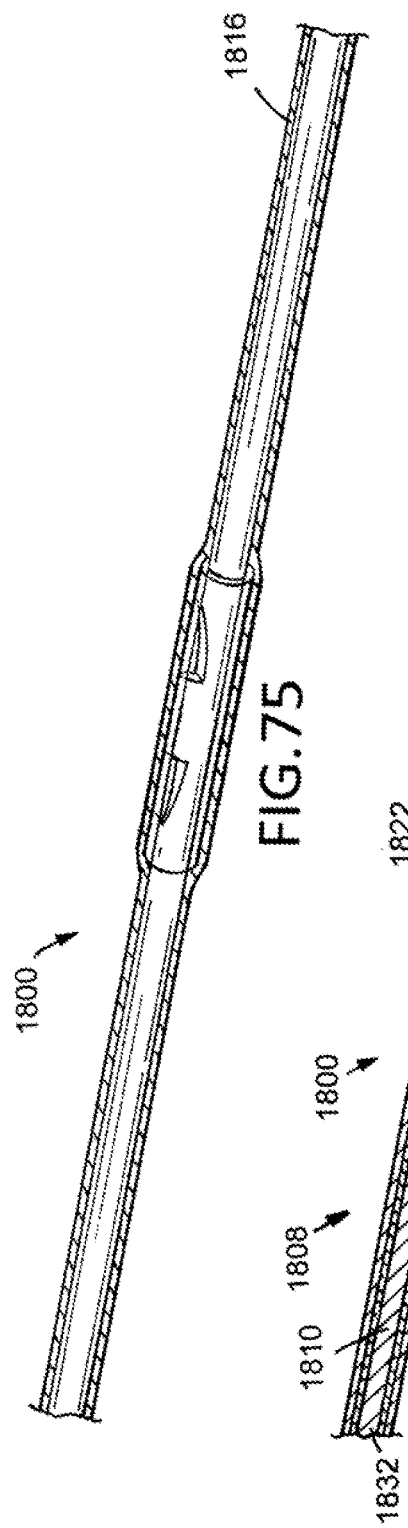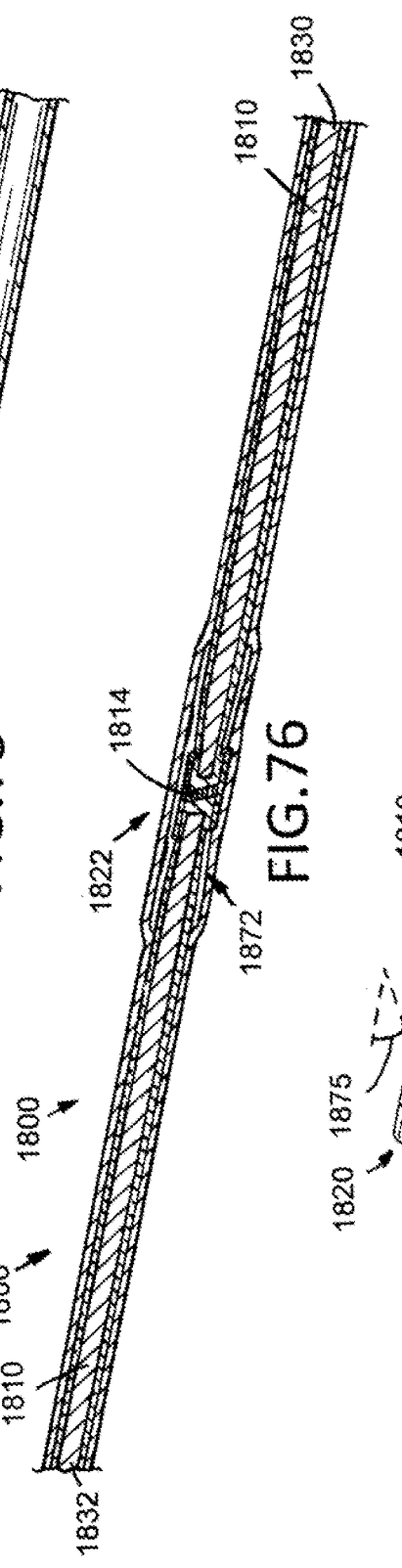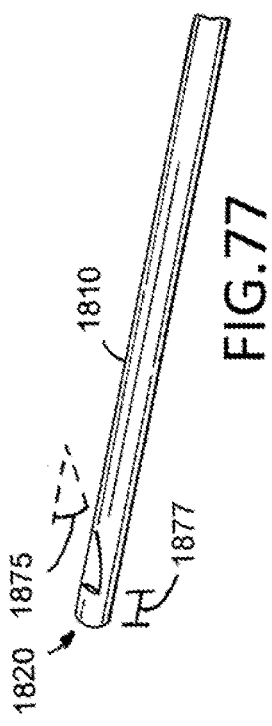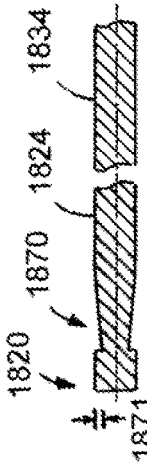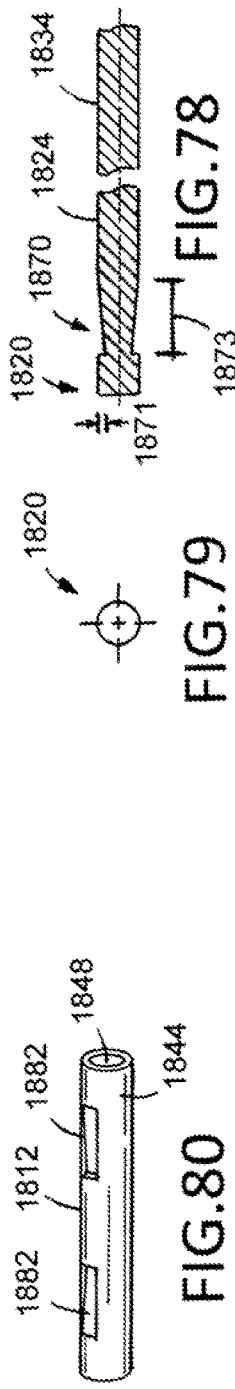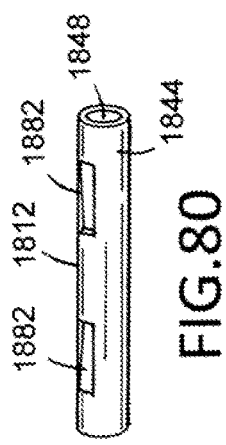

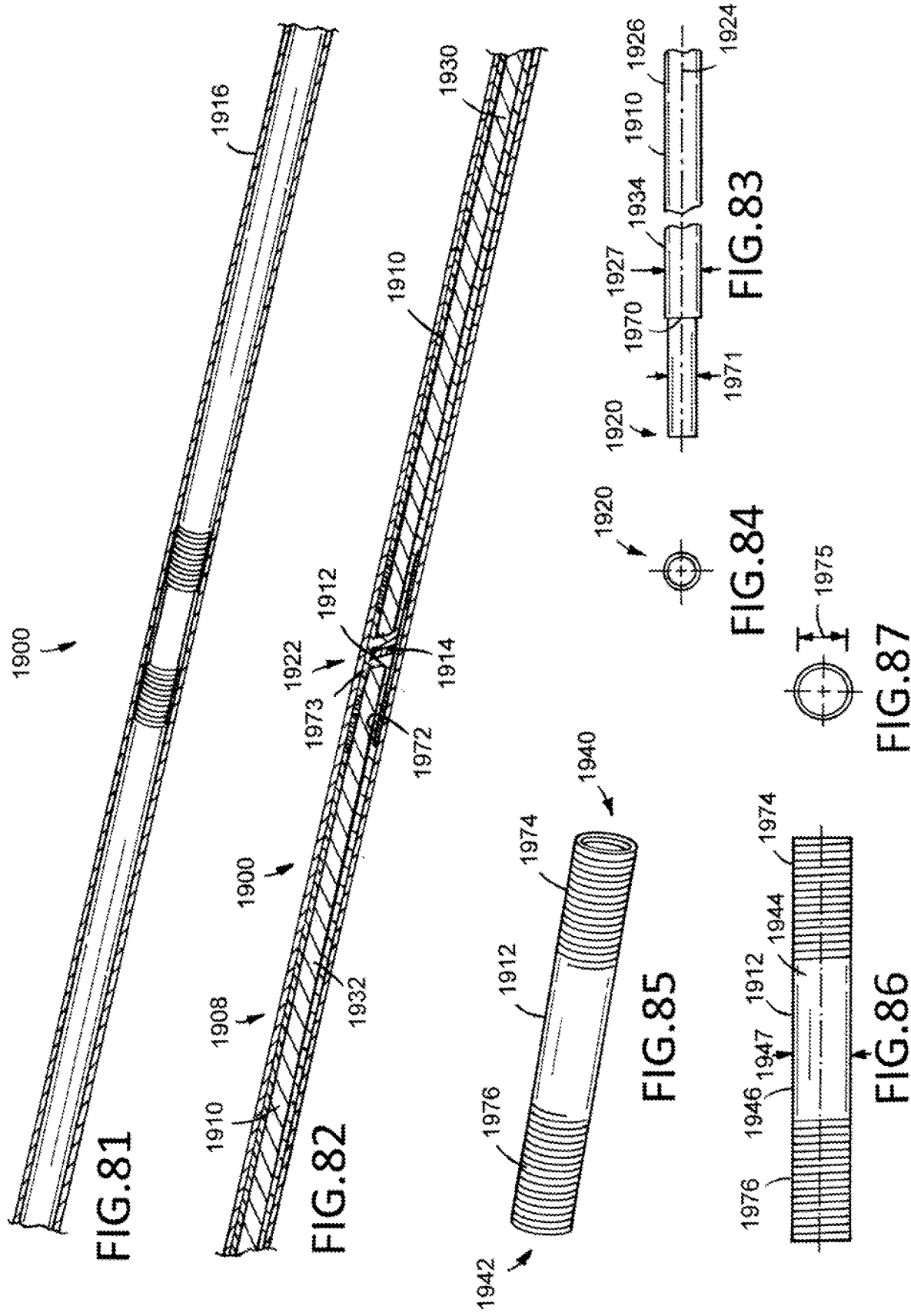

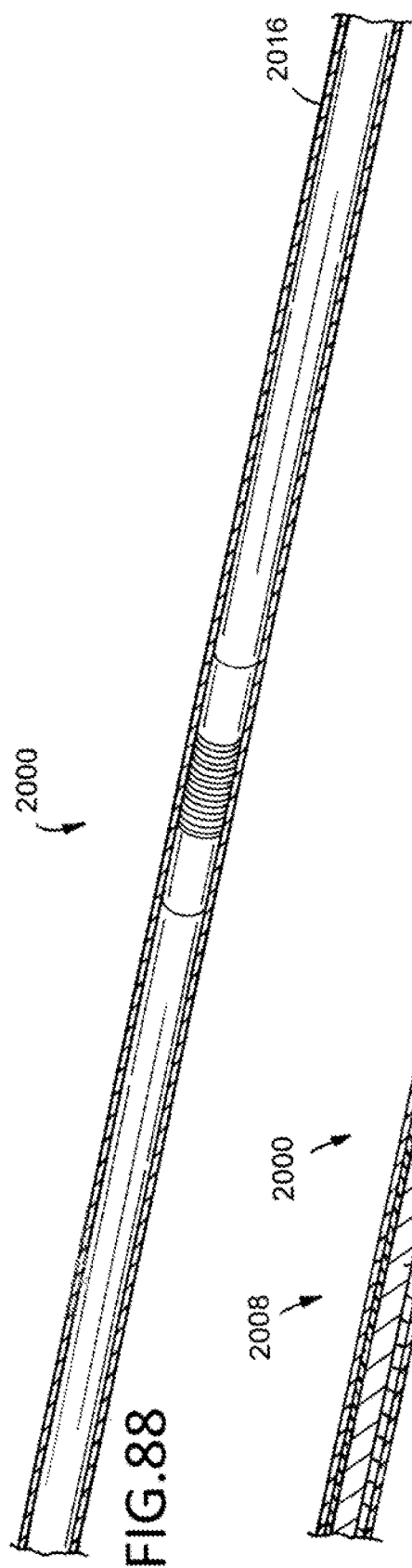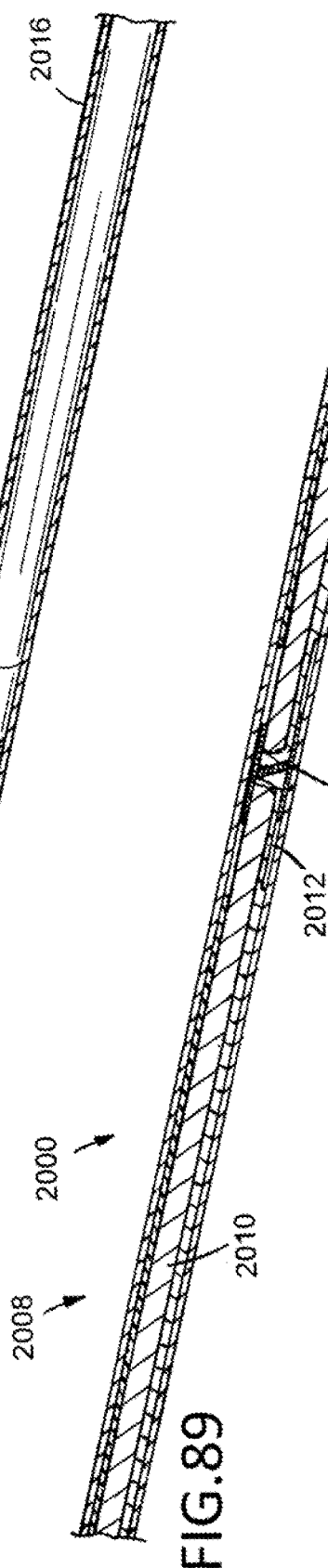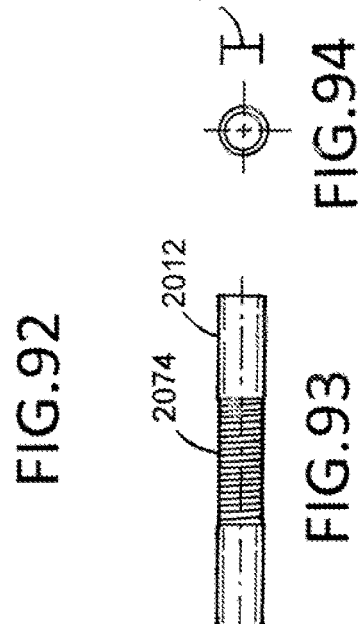

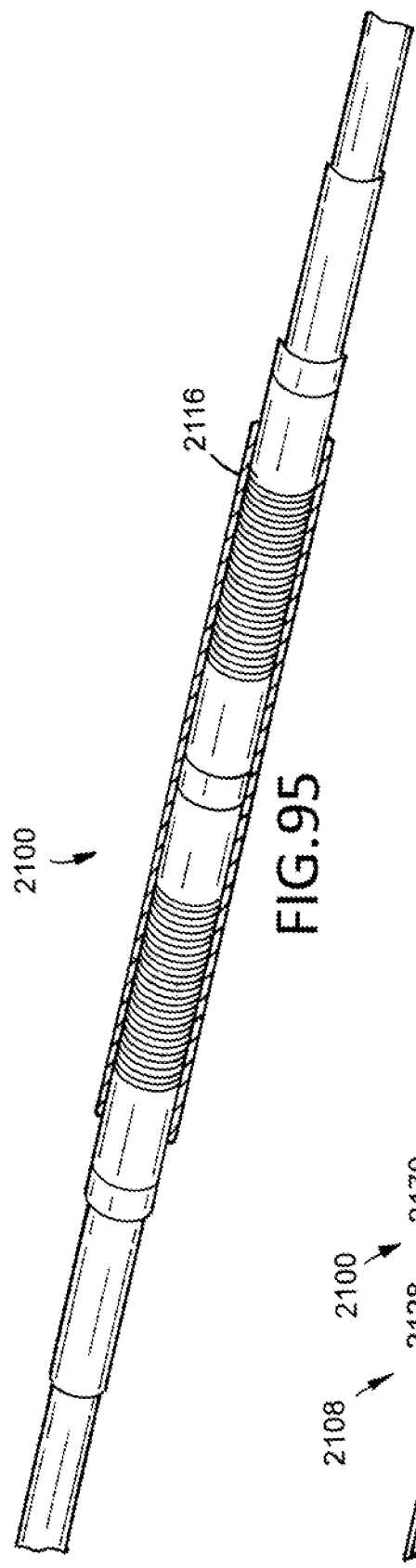
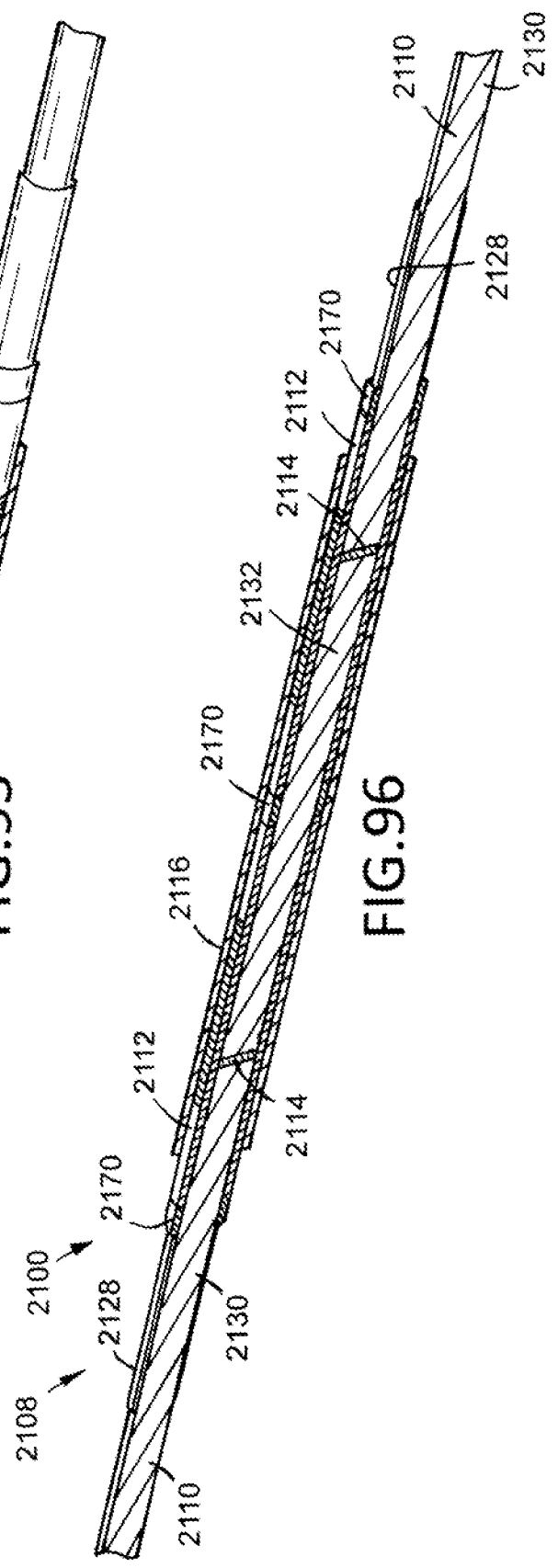
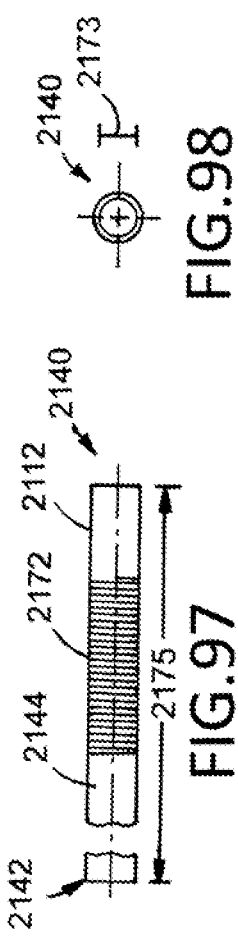

MRI COMPATIBLE INTERVENTIONAL WIREGUIDE

RELATED APPLICATION

This application is a continuation of U.S. application Ser. No. 16/207,391, filed Dec. 3, 2018, which claims the benefit of U.S. Provisional Application No. 62/594,010, filed Dec. 3, 2017. The entire contents of each of these related applications are hereby incorporated by reference into this disclosure.

FIELD

The disclosure relates to the field of medical devices. More particularly, the disclosure relates to interventional wireguides suitable for use with magnetic resonance imaging (MRI) equipment and techniques.

BACKGROUND

The field of interventional MRI is gaining wider acceptance and seeing an increase in the number of procedures that can be performed. Interventional procedures conducted under MRI have several benefits over X-Ray-guided interventions. For example, the patient is not exposed to ionizing radiation. Also, MRI provides the ability to characterize tissue and functional flow during an interventional procedure.

To further advance the development and adoption of interventional MRI procedures, interventional devices that are suitable for use with MRI equipment and techniques must be developed. To be MRI compatible, these devices must be safe from radiofrequency (RF) heating, deflection, and significant image artifact that impedes navigation while remaining visible to the MRI operator without obscuring the anatomical structures.

Interventional Cardiovascular Magnetic Resonance (iCMR) catheter procedures have been known for several years. To date these procedures have been carried out using non-metallic polymeric catheters, balloons, and sheaths. These procedures have been performed without the benefit of the core tool for interventional procedures—the guidewire. To date, no suitable MRI-compatible guidewire has been developed that meets the user needs for these procedures. The lack of an appropriate designed guidewire has been a significant impediment to adoption of iCMR. Conventional guidewires, such as those that are ferromagnetic, are not suitable for use during iCMR because they employ metallic shafts for mechanical performance and as such, they are conductors subject to RF heating, deflection, and significant image artefact. Non-metallic guidewires have proven to have inadequate mechanical properties, trackability, and torquability such that clinical adoption has not occurred.

A need exists, therefore, for new and improved guidewires suitable for use with magnetic resonance imaging (MRI) equipment and techniques.

Brief Summary of Selected Examples

Various example interventional wireguides are described.

An example wireguide has a series of individual segments, a plurality of connectors, and a plurality of spacers. Each segment in the series of individual segments has a first end and a second end. Each connector of the plurality of connectors joins adjacent segments in the series of individual segments to one another such that a first end of a first segment and a second end of a second segment in the series of individual segments are attached to a connector of the plurality of connectors. A spacer of the plurality of spacers disposed between each pair of adjacent segments in the series of individual segments. Each of the segments in the series of individual segments is electrically insulated from an adjacent segment in the series of individual segments.

Another example wireguide has a series of individual segments, a plurality of connectors, and a plurality of spacers. Each segment in the series of individual segments has a first end, a second end, and a main body. Each segment in the series of individual segments includes a segment coating formed of an electrically insulating material. The main body of each segment in the series of individual segments defines a first plurality of recesses and a second plurality of recesses. The first plurality of recesses is defined between the first end of a segment in the series of individual segments and the second end of the segment in the series of individual segments. The second plurality of recesses is defined between the first plurality of recesses and the second end of the segment in the series of individual segments. Each connector of the plurality of connectors joins adjacent segments in the series of individual segments to one another such that a first end of a first segment and a second end of a second segment in the series of individual segments are attached to a connector of the plurality of connectors. Each connector in the plurality of connectors has a main body that defines a first passageway and a plurality of passageways. Each passageway of the plurality of passageways extends through the main body and is in communication with the first passageway. A portion of the plurality of passageways is aligned with a recess of the plurality of recesses. A spacer of the plurality of spacers is disposed between each pair of adjacent segments in the series of individual segments. Each spacer of the plurality of spacers is a separate member relative to the segment coating and is formed of an electrically insulating material. Each of the segments in the series of individual segments is electrically insulated from an adjacent segment in the series of individual segments.

Another example wireguide has a series of individual segments, a plurality of connectors, a plurality of spacers, a wireguide coating, and a plurality of markers. Each segment in the series of individual segments is formed of Nitinol and has a first end, a second end, and a main body. Each segment in the series of individual segments includes a segment coating formed of a polymer and has a length that is less than 10 centimeters. The main body of each segment in the series of individual segments defines a first plurality of recesses and a second plurality of recesses. The first plurality of recesses is defined between the first end of a segment in the series of individual segments and the second end of the segment in the series of individual segments. The second plurality of recesses is defined between the first plurality of recesses and the second end of the segment in the series of individual segments. Each recess of the first plurality of recesses and the second plurality of recesses has a hemispheroid configuration. Each connector of the plurality of connectors joins adjacent segments in the series of individual segments to one another such that a first end of a first segment and a second end of a second segment in the series of individual segments are attached to a connector of the plurality of connectors. Each connector in the plurality of connectors has a main body defining a first passageway and a plurality of passageways. Each passageway of the plurality of passageways extends through the main body and is in communication with the first passageway. A portion of the plurality of passageways is aligned with a recess of the plurality of recesses. A spacer of the plurality of spacers is disposed between each pair of adjacent segments in the series of individual segments. Each spacer of the plurality of spacers is a separate member relative to the segment coating and is formed of an electrically insulating material. The wireguide coating is disposed over the series of individual segments and the plurality of connectors. The wireguide coating is formed of an electrically insulating material. The plurality of markers is attached to the series of individual segments. Each marker of the plurality of markers is formed of a material that is visible under MRI. Each of the segments in the series of individual segments is electrically insulated from an adjacent segment in the series of individual segments.

Various example methods of assembling a medical device are included, including methods of assembly that produce the various example medical devices described and illustrated herein.

Various example methods of using an interventional wireguide, various example imaging methods, and various example methods of performing an interventional medical treatment are also included.

Additional understanding of the example interventional wireguides and methods can be obtained by reviewing the detailed description of selected examples, below, with reference to the appended drawings.

DESCRIPTION OF FIGURES

FIG. 2 is a magnified view of Area A shown in FIG. 1.
FIG. 3 is a sectional view of the wireguide shown in FIG. 2 taken along the lengthwise axis of the wireguide.
FIG. 4 is a magnified view of Area B shown in FIG. 3.
FIG. 5 is a partial perspective view of another example interventional wireguide.
FIG. 6 is a sectional view of the wireguide shown in FIG. 5 taken along the lengthwise axis of the wireguide.
FIG. 7 is a magnified view of Area C shown in FIG. 6.
FIG. 8 is a partial side view of another example interventional wireguide.
FIG. 9 is a perspective sectional view of the wireguide shown in FIG. 8 taken along the lengthwise axis of the wireguide.
FIG. 10 is a partial perspective view of a portion of the wireguide shown in FIG. 8 partially broken away.
FIG. 11 is a partial side view of a segment of the wireguide shown in FIG. 8.
FIG. 12 is an end view of the segment shown in FIG. 11.
FIG. 13 is a partial perspective view of another example interventional wireguide.
FIG. 14 is side view of the wireguide shown in FIG. 13 partially broken away.
FIG. 15 is a partial perspective view of a segment of the wireguide shown in FIG. 13.
FIG. 16 is a side view of the segment shown in FIG. 15.
FIG. 17 is an end view of the segment shown in FIG. 15.
FIG. 18 is a perspective sectional view of adjacent segments of another example interventional wireguide taken along the lengthwise axis of the wireguide.
FIG. 19 is a perspective view of a segment of the wireguide shown in FIG. 18.
FIG. 20 is a side view of the segment shown in FIG. 19.
FIG. 21 is an end view of the segment shown in FIG. 19.
FIG. 22 is another end view of the segment shown in FIG. 19.
FIG. 23 is a partial perspective view of another example interventional wireguide partially broken away.
FIG. 24 is a partial perspective view of a segment of the wireguide shown in FIG. 23.
FIG. 25 is a side view of the segment shown in FIG. 24.
FIG. 26 is an end view of the segment shown in FIG. 24.
FIG. 27 is a side view of the wireguide shown in FIG. 23.
FIG. 28 is a side view of a connector of the wireguide shown in FIG. 23.
FIG. 29 is an end view of the connector shown in FIG. 28.
FIG. 30 is a partial perspective view of another example interventional wireguide partially broken away.
FIG. 31 is a partial side view of adjacent segments of the wireguide shown in FIG. 30.
FIG. 32 is a partial perspective view of a segment of the wireguide shown in FIG. 30.
FIG. 33 is a side view of the segment shown in FIG. 32.
FIG. 34 is an end view of the segment shown in FIG. 32.
FIG. 35 is a partial perspective view of another example interventional wireguide.
FIG. 36 is a partial side view of adjacent segments of the wireguide shown in FIG. 35.
FIG. 37 is a partial perspective view of a segment of the wireguide shown in FIG. 35.
FIG. 38 is a side view of the segment shown in FIG. 37.
FIG. 39 is an end view of the segment shown in FIG. 37.
FIG. 40 is a partial perspective view of another example interventional wireguide.
FIG. 41 is a magnified view of Area F shown in FIG. 40 partially broken away.
FIG. 42 is a partial perspective view of a segment of the wireguide shown in FIG. 40.
FIG. 43 is a side view of the segment shown in FIG. 42.
FIG. 44 is an end view of the segment shown in FIG. 42.
FIG. 45 is a side view of a portion of another example interventional wireguide.
FIG. 46 is a side view of adjacent segments of the wireguide shown in FIG. 45.
FIG. 47 is a perspective view of a segment of the wireguide shown in FIG. 45.
FIG. 48 is a partial side view of the segment shown in FIG. 47.
FIG. 49 is an end view of the segment shown in FIG. 47.
FIG. 50 is a side view of a portion of another example interventional wireguide. The connector is shown in hidden lines and the wireguide coating is omitted for clarity.
FIG. 51 is a partial side view of a segment of the wireguide shown in FIG. 50.
FIG. 52 is an end view of the segment shown in FIG. 51.
FIG. 53 is a partial perspective view of another example interventional wireguide.
FIG. 54 is a perspective view of the wireguide shown in FIG. 53 partially broken away.
FIG. 55 is a partial perspective view of a segment of the wireguide shown in FIG. 53.
FIG. 56 is a side view of the segment show in FIG. 55.
FIG. 57 is an end view of the segment shown in FIG. 55.
FIG. 58 is another end view of the segment shown in FIG. 55.
FIG. 59 is a side view of a connector of the wireguide shown in FIG. 53.
FIG. 60 is an end view of the connector shown in FIG. 59.
FIG. 61 is another end view of the connector shown in FIG. 59.

FIG. 63 is a partial perspective view of another example interventional wireguide partially broken away.

FIG. 64 is a sectional view of the wireguide shown in FIG. 63 taken along the lengthwise axis of the wireguide.

FIG. 65 is a partial perspective view of another example interventional wireguide partially broken away.

FIG. 66 is a sectional view of the wireguide shown in FIG. 65 taken along the lengthwise axis of the wireguide.

FIG. 67 is a partial side view of a segment of the wireguide shown in FIG. 65.

FIG. 68 is an end view of the segment shown in FIG. 67.

FIG. 69 is a partial perspective view of another example interventional wireguide partially broken away.

FIG. 70 is a sectional view of the wireguide shown in FIG. 69 taken along the lengthwise axis of the wireguide.

FIG. 71 is a partial perspective view of another example interventional wireguide partially broken away.

FIG. 72 is another partial perspective view of the wireguide shown in FIG. 71 partially broken away.

FIG. 73 is a partial side view of a segment of the wireguide shown in FIG. 71.

FIG. 74 is a cross-sectional view of the segment shown in FIG. 73 taken along line 74-74.

FIG. 75 is a partial perspective view of another example interventional wireguide partially broken away.

FIG. 76 is a sectional view of the wireguide shown in FIG. 75 taken along the lengthwise axis of the wireguide.

FIG. 77 is a partial perspective view of a segment of the wireguide shown in FIG. 75.

FIG. 78 is a partial sectional side view of the segment shown in FIG. 77 taken along the lengthwise axis of the segment.

FIG. 79 is an end view of the segment shown in FIG. 77.

FIG. 80 is a perspective view of a connector of the wireguide shown in FIG. 75.

FIG. 81 is a partial perspective view of another example interventional wireguide partially broken away.

FIG. 82 is a sectional view of the wireguide shown in FIG. 81 taken along the lengthwise axis of the wireguide.

FIG. 83 is a partial side view of a segment of the wireguide shown in FIG. 81.

FIG. 84 is an end view of the segment shown in FIG. 83.

FIG. 85 is a perspective view of a connector of the wireguide shown in FIG. 81.

FIG. 86 is a side view of the connector shown in FIG. 85.

FIG. 87 is an end view of the connector shown in FIG. 85.

FIG. 88 is a partial perspective view of another example interventional wireguide partially broken away.

FIG. 89 is a sectional view of the wireguide shown in FIG. 88 taken along the lengthwise axis of the wireguide.

FIG. 90 is a partial side view of a segment of the wireguide shown in FIG. 88.

FIG. 91 is an end view of the segment shown in FIG. 90.

FIG. 92 is a perspective view of a connector of the wireguide shown in FIG. 88.

FIG. 93 is a side view of the connector shown in FIG. 92.

FIG. 94 is an end view of the connector shown in FIG. 92.

FIG. 95 is a partial perspective view of a portion of another example interventional wireguide partially broken away.

FIG. 96 is a sectional view of the wireguide shown in FIG. 95 taken along the lengthwise axis of the wireguide.

FIG. 97 is a partial side view of a connector of the wireguide shown in FIG. 95.

FIG. 98 is an end view of the connector shown in FIG. 97.

DETAILED DESCRIPTION OF SELECTED EXAMPLES

Figure 1:
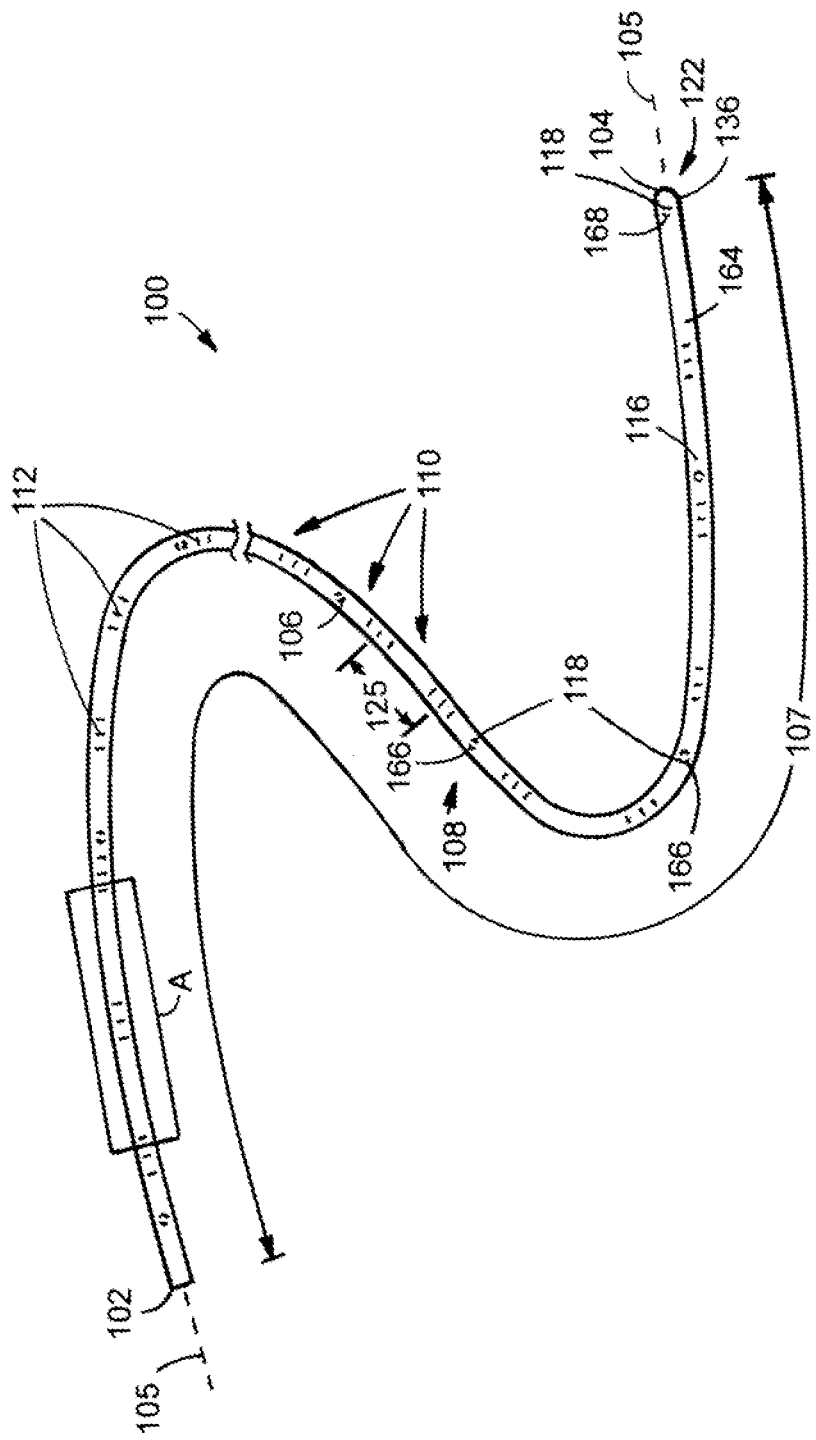
FIG. 1 illustrates a partial perspective view of an example interventional wireguide.

The following detailed description and the appended drawings describe and illustrate various example medical devices and methods. The description and illustration of these examples are provided to enable one skilled in the art to make and use examples of the inventive medical devices and to perform examples of the inventive methods. They do not limit the scope of the claims in any manner.

FIGS. 1, 2, 3, and 4 illustrate an example interventional wireguide 100. The wireguide 100 has a proximal end 102, a distal end 104, a lengthwise axis 105, a body 106 extending between the proximal end 102 and the distal end 104, and a length 107 that extends from the proximal end 102 to the distal end 104. The wireguide 100 has a segmented construction and includes a series 108 of individual segments 110, a plurality of connectors 112, a plurality of spacers 114, a wireguide coating 116, and a plurality of markers 118. Adjacent segments 110 in the series 108 are joined by individual connectors 112.

A wireguide can have any suitable length and selection of a suitable length for a wireguide can be based on various considerations, including the intended use of the wireguide. Examples of lengths considered suitable for a wireguide include lengths equal to, greater than, less than, or about 100 centimeters, 110 centimeters, 120 centimeters, 130 centimeters, 140 centimeters, 240 centimeters, 250 centimeters, 260 centimeters, 270 centimeters, 280 centimeters, between about 50 centimeters and about 350 centimeters, between about 100 centimeters and about 280 centimeters, between about 120 centimeters and about 260 centimeters, and any other length considered suitable for a particular embodiment.

Each of the segments 110 in the series 108 is electrically insulated from an adjacent segment 110 in the series 108, as described in more detail herein, and has a first end 120, a second end 122, a lengthwise axis 123, a main body 124, a length 125 that extends from the first end 120 to the second end 122, an outer surface 126, a segment coating 128, and an outside diameter 127, which includes the thickness of the segment coating 128. Each segment 110 is positioned adjacent to another segment 110 in the series 108, as shown in FIG. 4, such that the first end 120 of a first segment 130 is disposed adjacent a second end 122 of second segment 132. As described in more detail herein, the adjacent segments 130, 132 are insulated from one another using the segment coating 128, a spacer of the plurality of spacers 114, and a connector of the plurality of connectors 112. In the illustrated embodiment, the main body 124 defines an elongate member 134 that has a continuous, and uninterrupted outer surface 126. The segment coating 128 is disposed over the entire main body 124 of each individual segment 110 such that the entire outer surface of the main body 124 of each segment 110 is covered by the coating 128. The segment coating 128 provides electrical insulation of a segment 112 from other elements, including adjacent segments 110 and connectors 112. As shown in FIG. 1, the main body 124 of a segment 110 that is disposed along a distal portion of the wireguide 100 that extends from the distal end 104 toward the proximal end 102 defines an atraumatic distal tip 136 on its second end 122. The distal tip 136 can be precision-ground to a desirable shape, size, and/or configuration. Alternative embodiments, however, can include an atraumatic distal tip that is a separate member attached to a second end of a segment.

A segment included in a wireguide can be formed of any suitable material and selection of a suitable material can be based on various considerations, including the material that forms a connector intended to be attached to a segment. Examples of materials considered suitable to form a segment include metals, metals in light of the electrical insulation provided by the segmented construction, electrically insulating materials, electrically non-conducting materials, shape memory alloys, including nickel-titanium alloys such as Nitinol, Superelastic Nitinol SE508 straight with black oxide, wires, Nitinol wires, matte finished Nitinol, polished Nitinol, combinations of those described herein, and any other material considered suitable for a particular embodiment.

Any suitable number of segments can be included in a wireguide and selection of a suitable number of segments can be based on various considerations, including the intended use of the wireguide. Examples of numbers of segments considered suitable to include in a wireguide include one, two, three, four, five, six, seven, eight, nine, ten, eleven, twelve, thirteen, fourteen, fifteen, more than fifteen, twenty, more than twenty, twenty-six, more than twenty-six, more than thirty, between one and thirty, between six and thirty-two, between twelve and twenty-six, and any other number of segments considered suitable for a particular embodiment. In the illustrated embodiment, the wireguide 100 includes twelve individual segments 110.

A segment included in a wireguide can have any suitable length and diameter. Selection of a suitable length and diameter for a segment can be based on various considerations, including the intended use of the wireguide. Examples of lengths considered suitable for a segment include lengths equal to, greater than, less than, or about 5 centimeters, 6 centimeters, 7 centimeters, 8 centimeters, 9 centimeters, 10 centimeters, 11 centimeters, 12 centimeters, 13 centimeters, 14 centimeters, 15 centimeters, 20 centimeters, 25 centimeters, 30 centimeters, greater than 15 centimeters, greater than 20 centimeters, greater than 30 centimeters, between about 5 centimeters and about 30 centimeters, between about 12 centimeters and about 30 centimeters, between about 5 centimeters and about 15 centimeters, between about 7 centimeters and about 13 centimeters, between about 9 centimeters and about 11 centimeters, lengths that are based on the field strength (e.g., 3 T, 1.5 T) of an magnetic resonance scanner, and any other length considered suitable for a particular embodiment. Examples of diameters considered suitable for a segment include diameters equal to, greater than, less than, or about 0.01 inches, 0.02 inches, 0.022 inches, 0.024 inches, 0.03 inches, 0.04 inches, diameters between about 0.01 inches and about 0.04 inches, diameters between about 0.022 inches and about 0.024 inches, and any other diameter considered suitable for a particular embodiment. In the illustrated embodiment, each segment 110 has a length less than 10 centimeters. Lengths less than 12 centimeters are considered advantageous for use with a 1.5 T magnetic resonance scanner at least because the prevent radiofrequency (RF) heating during use. In alternative embodiments, however, the lengths of segments included in a wireguide could vary. For example, a first segment, or first set of segments, could have a first length and a second segment, or second set of segments, could have a second length that is different than the first length.

A segment included in a wireguide can have any suitable structural configuration and selection of a suitable structural configuration can be based on various considerations, including the structural arrangement of a connector included in a wireguide. In the illustrated embodiment, each segment 110 has the same structural configuration. In alternative embodiments, however, a wireguide can include segments that have varying structural configurations. For example, a first segment, or set of segments, can have a first structural configuration and a second segment, or second set of segments, can have a second structural configuration that is different than the first structural configuration.

A segment coating included on a segment can be formed of any suitable material applied to any suitable portion of a segment using any suitable technique or method. Selection of a material considered suitable to form a segment coating and of a suitable technique or method to apply a segment coating can be based on various considerations, including the material that forms a connector intended to be attached to a segment. Examples of materials considered suitable to form a segment coating include electrically non-conductive materials, electrically insulating materials, such as polymers, thermosetting polymers, polyimides, enamels, and/or epoxy resins, ceramics, non-conductive oxide, thermoplastics, high-temperature thermoplastics, and any other material considered suitable for a particular embodiment. Examples of techniques and methods considered suitable to apply a segment coating include conventional technique and methods, such as spraying, applying with a brush, powder coating, forming a conformal coating, extruding a coating over a main body of a segment, dipping, dipping into a solution, casting, and any other technique or method considered suitable for a particular embodiment. Examples of portions of an outer surface of a main body considered suitable to apply a segment coating include the entire outer surface of a main body, a portion of an outer surface of a main body, and any other portion of a main body considered suitable for a particular embodiment. Alternatively, a segment coating can be omitted from a segment, as described in more detail herein. In the illustrated embodiment, the segment coating 128 is a polyimide that is applied by dipping to the entire outer surface of the main body 124 of each segment 110 into the polyimide. It is considered advantageous to utilize a Nitinol main body 124 that includes a segment coating 128, such as a polyimide, enamel, or epoxy resin at least because of the thermosetting properties of these materials.

Each of the connectors 112 is electrically insulated from the adjacent segments 130, 132 joined by the particular connector 112, as described in more detail herein, and has a first end 140, a second end 142, a length 143, and a main body 144 that defines an outer surface 146 and a passageway 148. Each connector 112 has an outside diameter 147 that is greater than the outside diameter 127 of each segment 110. Each connector 112 is electrically insulated from other elements, including adjacent segments 130, 132 joined by a particular connector 112. This can be accomplished by the segment coating 128, applying a connector coating to a connector similar to the application of a segment coating described herein, and/or using an insulating material to attach a connector to a segment (e.g., adhesive). Any suitable number of connectors can be included in a wireguide and selection of a suitable number of connectors can be based on various considerations, including the intended use of the wireguide. Examples of numbers of connectors considered suitable to include in a wireguide include zero, one, two, three, four, five, six, seven, eight, nine, ten, eleven, twelve, thirteen, fourteen, fifteen, more than fifteen, twenty, more than twenty, twenty-five, more than twenty-five, more than thirty, between one and thirty, between five and thirty-one, between eleven and twenty-five, and any other number of connectors considered suitable for a particular embodiment. In the illustrated embodiment, the wireguide 100 includes eleven connectors 112.

A connector included in a wireguide can be formed of any suitable material and attached to a segment using any suitable technique or method of attachment. Selection of a suitable material and of a suitable technique or method of attachment can be based on carious considerations, including the material that forms a segment to which a connector is intended to be attached. Examples of materials considered suitable to form a connector include metals, metals in light of the electrical insulation provided by the segmented construction, shape memory alloys, including nickel-titanium alloys such as Nitinol, stainless steel, including Austenitic stainless steel, MP35N, stainless steel containing Iron, and Inconel, cobalt chromium, cobalt chromium alloys, electrically non-conductive materials, electrically insulating materials, such as polymeric materials, such as reinforced polyether ether ketone (PEEK), reinforced PEEK, and Polybenzimidazole (Celazole), fiberglass, toughened fiberglass, glass, Quartz, Ceramic composite materials as in oriented fiber polishing stones, materials, such as those described herein, that include embedded markers (e.g., MRI markers), such as those described herein, and any other material considered suitable for a particular embodiment. Examples of techniques and methods of attachment considered suitable between a connector and a segment include using adhesives, such as epoxies, cyanoacrylate, UV-activated adhesives, mechanical connectors, such as screws, shrinking a connector on first and second segments (e.g., shrinking a Nitinol connector thermally expanded then contracted by warming the connector), cryo-fitting, welding, spin welding, friction welding, overmolding, insert-molding, those described herein, and any other technique or method considered suitable for a particular embodiment. Use of adhesives provides a mechanism for both attaching a connector to a segment and for providing electrical insulation of the connector from the segment.

A connector included in a wireguide can have any suitable length and selection of a suitable length for a connector can be based on various considerations, including the intended use of the wireguide. Examples of lengths considered suitable for a connector include lengths equal to, greater than, less than, or about 1 centimeter, 2 centimeters, 2.5 centimeters, 3 centimeters, 4 centimeters, 5 centimeters, between about 1 centimeter and about 5 centimeters, between about 1.5 centimeters and about 3 centimeters, between about 2.25 centimeters and about 2.75 centimeters, lengths that are less than the length of a segment of a wireguide, lengths that are about one quarter of the length of a segment of a wireguide, and any other length considered suitable for a particular embodiment. In the illustrated embodiment, each connector 112 has a length 143 that is less than the length 125 of a segment 110. In alternative embodiments, however, the lengths of connectors included in a wireguide could vary. For example, a first connector, or first set of connectors, could have a first length and a second connector, or second set of connectors, could have a second length that is different than the first length.

A connector included in a wireguide can have any suitable structural configuration and selection of a suitable structural configuration can be based on various considerations, including the structural configuration of a segment included in a wireguide. In the illustrated embodiment, each connector 112 has the same structural configuration and is a tubular member 149. In alternative embodiments, however, a wireguide can include connectors that have varying structural configurations. For example, a first connector, or first set of connectors, can have a first structural configuration and a second connector, or second set of connectors, can have a second structural configuration that is different than the first structural configuration.

A spacer of the plurality of spacers 114 is disposed between each set of adjacent segments 130, 132 and has a first end 150, a second end 152, and a main body 154. Each spacer is a separate member relative to the segment coating 128 and is formed of an electrically insulating material (e.g., electrically non-conductive material) and provides additional electrical insulation between adjacent segments 130, 132. A spacer can have any suitable structural configuration and be formed of any suitable material. Selection of a suitable structural configuration and of a suitable material can be based on various considerations, including the structural configuration of a connector within which a spacer is intended to be disposed. Examples of structural configurations considered suitable for a spacer include cylindrical, and any other structural arrangement considered suitable for a particular embodiment. Examples of materials considered suitable to form a spacer include electrically insulting materials, electrically non-conductive materials, any material described herein, such as the electrically insulating, or non-conductive, materials described herein, polymers, thermoset polymers, ceramics, and any other material considered suitable for a particular embodiment. In the illustrated embodiment, each spacer of the plurality of spacers 114 is cylindrical. In alternative embodiments, a plurality of spacers can be completely omitted from a wireguide or only be disposed between a portion of adjacent segments of a series of individual segments (e.g., in embodiments in which additional electrical insulation between adjacent segments is not required).

In the illustrated embodiment, the wireguide coating 116 is disposed over each segment 110 and connector 112 and along the entire length of the wireguide 100. The wireguide coating 116 has an outer surface 156, an inner surface 158, and main body 160 that defines a jacket 162 over each segment 110 and connector 112. In the illustrated embodiment, a lubricious coating 164 is disposed on the outer surface 156 of the wireguide coating 116. While some embodiments, such as wireguide 100, have been illustrated as including a wireguide coating that has an outside diameter that is greater along the length of a connector than the outside diameter along the length of a segment, depending on the process being used to apply a wireguide coating (e.g., extrusion), some embodiments may include a wireguide coating that has a continuous outside diameter along its entire length or a majority of its length, such that the wireguide coating has a continuous, and uninterrupted, outer surface. A wireguide coating included in a wireguide can be formed of any suitable material and can be applied to any suitable portion of a wireguide using any suitable technique or method. Selection of a suitable material to form a wireguide coating, a suitable portion of a wireguide to include a wireguide coating, and of a suitable technique or method to apply a wireguide coating can be based on various considerations, including the material that forms a segment and/or connector. Examples of materials considered suitable to form a wireguide coating include electrically insulting materials, electrically non-conductive materials, polymeric materials, polymers, such as polyurethane, Pebax, and any other material considered suitable for a particular embodiment. Examples of techniques and methods of applying a wireguide coating considered suitable include extrusion processes, spraying, re-flow techniques, re-flow techniques with shrink tubing over a polymeric sleeve, and any other technique or method considered suitable for a particular embodiment. The inclusion of a wireguide coating advantageously provides a smooth outer surface that is substantially free of bumps or other irregularities. In alternative embodiments, a wireguide coating can be omitted from a wireguide or only disposed along a portion of a length of a wireguide (e.g., in embodiments in which additional electrical insulation and/or a smooth outer surface is not required). For example, a wireguide coating can be disposed over only a portion of the length of a wireguide (e.g., working length, about 150 centimeters, between about 100 centimeters and about 200 centimeters, only over each connector, only over each connector and a portion of a segment disposed adjacent to a connector).

The lubricious coating 164 is applied to the outer surface of the wireguide coating 116 along the entire length of the wireguide coating 116. In alternative embodiments, however, a lubricious coating can be applied only to a portion of a length of a wireguide coating (e.g., working length). A lubricious coating can be formed of any suitable material and applied to a wireguide coating using any suitable technique or method. Examples of materials considered suitable to form a lubricious coating include PVP (polyvinylpyrrolidone) based hydrophilic coatings, any lubricious material considered suitable for use in medical devices intended for intravascular use, and any other coating considered suitable for a particular embodiment.

In the illustrated embodiment, the plurality of markers 118 includes a series of individual markers 166 (e.g., passive markers, active markers) disposed along the length 107 of the body 106 (e.g., equally spacer along the length 107 (e.g., every 10 centimeters), staggered along the length 107) of the wireguide 100 and a distal tip marker 168 (e.g., passive marker, active marker) disposed on the distal end 104 of the wireguide 100. Alternatively, a distal tip marker can comprise a plurality of distal tip markers (e.g., three) disposed at the distal end such that the distal end of a wireguide can be differentiated from the length of the wireguide. Each marker of the plurality of markers 118 can be formed of any suitable material and positioned on a wireguide coating, embedded within the material that forms a wireguide coating, on a segment, embedded within the material that forms a segment, on a connector, embedded within the material that forms a connector, on a spacer, and/or embedded within the material that forms a spacer using any suitable technique or method. Selection of a suitable material to form a marker and of a suitable technique or method to position a marker on a wireguide can be based on various considerations, including the material that forms a wireguide coating, segment, connector, and/or spacer. Examples of materials considered suitable to form a marker include polymers, polymers compounded Iron Oxide, Gadolinium, stainless steel, stainless steel 304, ferromagnetic stainless steel, materials that are visible under MRI, Nitinol oxides, Nitinol oxides that are ferromagnetic, and any other material considered suitable for a particular embodiment. Examples of techniques and methods of positioning a marker on a wireguide include embedding a marker within a material that forms a portion of a wireguide (e.g., wireguide coating, segment, segment coating, connector, spacer), forming a marker and attaching the marker to a portion of a wireguide (e.g., wireguide coating, segment, series of individual segments, connector, spacer), swaging, and any other technique or method considered suitable for a particular embodiment. For examples, a marker, or a plurality of markers, can be incorporated into a wireguide by compounding a nanomagnetite into a polymer, extruding the material into a tube form, cutting the tube into rings, and using the rings as marker bands, which can be disposed over one or more segments and/or connectors and covered by a wireguide coating. Alternatively, a metallic marker band can be utilized due to their ease of use.

In the illustrated embodiment, each marker in the series of individual markers 166 is embedded into the material that forms the wireguide coating 116 such that it is disposed within the main body 160 of the wireguide coating 116. Each marker of the plurality of markers 118 provides MRI conspicuity. In the illustrated embodiment, the distal tip marker 168 is structurally, or otherwise differentiated from, each marker in the series of individual markers 166 such that it can be differentiated from the series of markers 166 under visualization of the plurality of markers 118. In alternative embodiments, a plurality of markers, a portion of a plurality of markers, and/or a distal tip marker, can be omitted from a wireguide (e.g., in embodiments in which visual markers are not required).

In the illustrated embodiment, the wireguide 100 can be assembled by placing a series 108 of segments 110 end to end, positioning a spacer of the plurality of spacers 114 between adjacent segments 130, 132, and joining adjacent segments 130, 132 to one another using a connector of the plurality of connectors 112 such that a spacer of the plurality of spacers 114 is disposed within each connector and between adjacent segments 130, 132 and a portion of each of the adjacent segments 130, 132 is disposed within the connector. The adjacent segments 130, 132 can be attached to one another using the plurality of connectors 112 in a sequential manner until a desired length is achieved. Subsequently, the wireguide coating 116 is applied to the segments 110 and connectors 112. Alternatively, in embodiments in which a desired length is known, the segments can be attached to one another using the plurality of connectors 112 concurrently. Each connector of the plurality of connectors 112 is attached to adjacent segments 130, 132 using an adhesive. The resulting wireguide 100 is a device in which the adjacent segments 130, 132 are not electrically coupled to the connector 112.

The example wireguide 100, and other examples described herein, are considered advantageous at least because they facilitate use of a wireguide that has pushability, torqueability, and steerability and can be utilized during MRI procedures (e.g., MRI-guided cardiovascular catheterization, interventional cardiac procedures) due to the various components (e.g., segments, connectors) being electrically uncoupled (e.g., isolated) from one another. For example, a catheter can be tracked over a wireguide, such as those described herein, during an MRI procedure. In addition, in embodiments that include one or more markers, a wireguide also facilitates visualization of the wireguide under MRI.

FIGS. 5, 6, and 7 illustrate another example wireguide 200. The wireguide 200 is similar to the wireguide 100 illustrated in FIGS. 1, 2, 3, and 4 and described above, except as detailed below. The wireguide 200 has a segmented construction and includes a series 208 of individual segments 210, a plurality of connectors 212, a plurality of spacers 214, and a wireguide coating 216.

In the illustrated embodiment, each of the segments 210 in the series 208 is electrically insulated from an adjacent segment 210 in the series 208 and has a first end 220, a second end 222, a lengthwise axis 223, a main body 224, an outer surface 226, and a segment coating 228. Each segment 210 is positioned adjacent to another segment 210 in the series 208, as shown in FIG. 7, such that the first end 220 of a first segment 230 is disposed adjacent a second end 222 of a second segment 232. As described in more detail herein, the adjacent segments 230, 232 are insulated from one another by the segment coating 228, a spacer of the plurality of spacers 214, and a connector of the plurality of connectors 212. In the illustrated embodiment, the main body 224 defines an elongate member 234, a first step 270 between the first end 220 and the second end 222, and a second step 272 between the first step 270 and the second end 222. The main body 224 has a first outside diameter 227 between the first step 270 and the second step 272, a second outside diameter 271 between the first step 270 and the first end 220, and a third outside diameter 273 between the second step 272 and the second end 222. The first outside diameter 227 is greater than the second outside diameter 271 and the third outside diameter 273. In the illustrated embodiment, the second outside diameter 271 and the third outside diameter 273 are equal. However, in alternative embodiments, a second outside diameter can be different than a third outside diameter.

In the illustrated embodiment, each connector of the plurality of connectors 212 has a length 229 that is less than the length of a segment 210 and equal to about the length of the spacer, the length of a segment that extends from the second end 222 to the second step 272, and the length of a segment that extends from the first end 220 to the first step 270. Each connector 212 has an outside diameter 247 that is equal to the first outside diameter 227 of a segment 210 such that the outside surface 246 of the connector 214 is flush with the outer surface 226 of the adjacent segments 230, 232 connected by the particular connector 212.

In the illustrated embodiment, the wireguide 200 can be assembled by applying an adhesive to within the passageway 248 of a connector of the plurality of connectors 212, positioning an end of a first segment 230 within the passageway 248, positioning a spacer of the plurality of spacers 214 within the passageway 248 such that it disposed adjacent and contacts the end (e.g., first end 220) of the first segment 230 disposed within the passageway 248, positioning an end of a second segment 232 within the passageway 248, and applying a force on each of the segments toward one another to join the adjacent segments 210 to one another. This results in the spacer of the plurality of spacers 214 being disposed within the passageway 248 defined by the connector 212 and between the adjacent segments 230, 232 and a portion of each of the first and second segments 210 being disposed within the passageway 248 of the connector 212. This process is repeated until a desired wireguide length is achieved. Subsequently, the wireguide coating 216 is applied to the segments 210 and connectors 212. Alternatively, a spacer can be positioned within a passageway prior to positioning an end of a first segment within the passageway.

The structural arrangement of example wireguide 200 is considered advantageous at least because it facilitates extruding the wireguide coating 216 over the series 208 of individual segments 210 and over connectors 214 that have the same outside diameter as the segments 210 and avoids challenges associated with extruding a wireguide coating over diameter changes, or steps, along the length of a wireguide that are present in example wireguide 100 due to the difference in the outside diameters of the segments 110 and connectors 112. To avoid the challenges associated with extruding a wireguide coating over diameter changes, or steps, along the length of the wireguide, such as those that are present in example wireguide 100 due to the difference in the outside diameters of the segments 110 and connectors 112, a feeder portion, or extruder inlet tube, could be tapered to allow for minor changes in the outside diameter of a wireguide (e.g., such as the changes in outside diameter between a segment 110 and a connector 112).

FIGS. 8, 9, 10, 11, and 12 illustrate another example wireguide 300. The wireguide 300 is similar to the wireguide 100 illustrated in FIGS. 1, 2, 3, and 4 and described above, except as detailed below. The wireguide 300 has a segmented construction and includes a series 308 of individual segments 310, a plurality of connectors 312, a plurality of spacers 314, and a wireguide coating 316.

In the illustrated embodiment, the main body 324 defines a rounded first end 320, a rounded second end 322, an elongate member 334, a first step 370 between the first end 320 and the second end 322, a second step 372 between the first step 370 and the second end 322, a first tapered portion 374, and a second tapered portion 376. This results in each segment 310 having a knob type profile on each end 320, 322. The main body 324 has a first outside diameter 327 (e.g., 0.018 inches) between the first step 370 and the second step 372, a second outside diameter 371 (e.g., 0.014 inches) between the first step 370 and the first tapered portion 374, and a third outside diameter 373 (e.g., 0.014 inches) between the second step 372 and the second tapered portion 376. The first outside diameter 327 is greater than the second outside diameter 371 and the third outside diameter 373. In the illustrated embodiment, the second outside diameter 371 and the third outside diameter 373 are equal. However, in alternative embodiments, a second outside diameter can be different than a third outside diameter. The first tapered portion 374 extends from the first end 320 toward the second end 322 and has a first tapered portion first outside diameter 377 (e.g., 0.013 inches) at the first end 320 and a first tapered portion second outside diameter 375 between the first end 320 and the first step 370 (e.g., 0.010 inches). The first tapered portion first outside diameter 377 is greater than the first tapered portion second outside diameter 375 and tapers to the first tapered portion second outside diameter 375 along the length of the wireguide 300. This results in the creation of a first recess 380 between the first step 370 and the first end 320. The second tapered portion 376 extends from the second end 322 toward the first end 320 and has a second tapered portion first outside diameter 379 (e.g., 0.013 inches) at the second end 322 and a second tapered portion second outside diameter 381 (e.g., 0.010 inches) between the second end 322 and the second step 372. The second tapered portion first outside diameter 379 is greater than the second tapered portion second outside diameter 381 and tapers to the second tapered portion second outside diameter 381 along the length of the wireguide 300. This results in the creation of a second recess 382 between the second step 372 and the second end 322.

In the illustrated embodiment, each connector 312 has an outside diameter 347 that is equal to the first outside diameter 327 of a segment 310 such that the outer surface 346 is flush with the outer surface 326 of the adjacent segments 310 connected by the particular connector 312. Each connector of the plurality of connectors 312 is attached to a pair of adjacent segments 320, 322 by crimping the connector to the pair of adjacent segments 320, 322 such that a first portion of the connector is disposed within the first recess 380 and a second portion of the connector is disposed within the second recess 382. This is accomplished by shape setting each connector of the plurality of connectors 314. An example technique of shape setting each connector of the plurality of connectors is heat treating, which can be utilized to take advantage of the shape memory properties of Nitinol. Another example technique that can be utilized is cryo-fitting.

In the illustrated embodiment, the wireguide 300 can be assembled by positioning an end of a first segment 330 within the passageway 348, positioning a spacer of the plurality of spacers 314 within the passageway 348 such that it disposed adjacent and contacts the end (e.g., first end 320) of the first segment 330 disposed within the passageway 348, positioning an end of a second segment 332 within the passageway 348, applying a force on each of the segments toward one another to join the adjacent segments 310 to one another, and positioning a portion of the connector within each of the recesses 380, 382 (e.g., by crimping, heat setting). This results in the spacer of the plurality of spacers 314 being disposed within the passageway 348 defined by the connector 312 and between the adjacent segments 330, 332 and a portion of each of the first and second segments 330, 332 being disposed within the passageway 348 of the connector 312. Alternatively, a spacer can be positioned within a passageway prior to positioning an end of a first segment within the passageway. This process is repeated until a desired wireguide length is achieved. Subsequently, the wire guide coating 316 is applied to the segments 310 and connectors 312.

The structural arrangement of example wireguide 300 is considered advantageous at least because it facilitates extruding the wireguide coating 316 over the segments 310 and connectors 314 that have the same outside diameter and avoids challenges associated with extruding a wireguide coating over diameter changes, or steps, along the length of a wireguide.

FIGS. 13, 14, 15, 16, and 17 illustrate another example wireguide 400. The wireguide 400 is similar to the wireguide 100 illustrated in FIGS. 1, 2, 3, and 4 and described above, except as detailed below. The wireguide 400 has a segmented construction and includes a series 408 of individual segments 410, a plurality of connectors 412, a plurality of spacers 414, and a wireguide coating 416.

In the illustrated embodiment, the main body 424 defines an elongate member 434, a first necked down section 470 between the first end 420 and the second end 422, a second necked down section 472 between the first necked down section 470 and the second end 422, a first stem 474, and a second stem 476. The main body 424 has a first outside diameter 427 (e.g., 0.018 inches) between the first necked down section 470 and the second necked down section 472, a second outside diameter 471 (e.g., 0.010 inches) at the first necked down section 470, and a third outside diameter 473 (e.g., 0.010 inches) at the second necked down section 472. The first outside diameter 427 is greater than the second outside diameter 471 and the third outside diameter 473. In the illustrated embodiment, the second outside diameter 471 and the third outside diameter 473 are equal. However, in alternative embodiments, a second outside diameter can be different than a third outside diameter. The first stem 474 extends from the first end 420 to the first necked down section 470 and has a first stem outside diameter 475 (e.g., 0.014 inches) that is greater than the second outside diameter 471. The second stem 476 extends from the second end 422 to the first necked down section 472 and has a second stem outside diameter 477 (e.g., 0.014 inches) that is greater than the third outside diameter 473.

In the illustrated embodiment, each connector 412 has an outside diameter 447 that is equal to about the first outside diameter 427 of a segment 410 such that the outer surface 446 is flush with the outer surface 426 of the adjacent segments 410 connected by the particular connector 412. Each connector of the plurality of connectors 412 is attached to a pair of adjacent segments 410 such that a first portion of the connector is disposed within the first necked down section 470 and a second portion of the connector is disposed within the second necked down section 472. This can be accomplished by crimping, cryo-fitting, or heat setting the connector onto the pair of adjacent segments 410. Optionally, a portion of a connector can be disposed within each of a first and second necked down sections, or one of the first and second necked down section, such that the remainder of the open area disposed between the connector and each of the necked down section, or one of the necked down sections, acts as a reservoir that receives marker for MRI visibility (e.g., the marker is disposed within the reservoir).

In the illustrated embodiment, the wireguide 400 can be assembled by positioning an end of a first segment 430 within the passageway 448, positioning a spacer of the plurality of spacers 414 within the passageway 448 such that it disposed adjacent and contacts the end (e.g., first end 420) of the first segment 430 disposed within the passageway 448, positioning an end of a second segment 432 within the passageway 448, applying a force on each of the segments toward one another to join the adjacent segments 410 to one another, and positioning a portion of the connector within each of the necked down sections 470, 472 (e.g., by crimping, heat setting). This results in the spacer of the plurality of spacers 414 being disposed within the passageway 448 defined by the connector 412 and between the adjacent segments 410 and a portion of each of the first and second segments 430, 432 being disposed within the passageway 448 of the connector 412. Alternatively, a spacer can be positioned within a passageway prior to positioning an end of a first segment within the passageway. This process is repeated until a desired wireguide length is achieved. Subsequently, the wire guide coating 416 is applied to the segments 410 and connectors 412.

The structural arrangement of example wireguide 400 is considered advantageous at least because it reduces the open area between a connector and an attached segment and facilitates extruding the wireguide coating 416 over the segments 410 and connectors 414 that have the same outside diameter and avoids challenges associated with extruding a wireguide coating over diameter changes, or steps, along the length of a wireguide. For example, portions of a connector can be disposed within each of the first necked down section and the second necked down section to conserve the bulk material properties of the material that forms a connector (e.g. Nitinol). This is believed to allow for consistent bend radii as the wire is bent into an arc. The connector length can be optimized to allow for optimal bending. The inventors believe that the structural arrangement of wireguide 400 allows for the tensile strength and column strength to be retained during use.

FIGS. 18, 19, 20, 21, and 22 illustrate adjacent segment of another example wireguide 500. The wireguide 500 is similar to the wireguide 100 illustrated in FIGS. 1, 2, 3, and 4 and described above, except as detailed below. The wireguide 500 has a segmented construction and includes a series 508 of individual segments 510 and a wireguide coating.

In the illustrated embodiment, each of the segments 510 is identical, except for the distal most segment, which includes the distal tip, as described herein. The main body 524 defines an elongate member 534, a recess 570, and a stem 572. The recess 570 extends into the main body 524 from the second end 522 toward the first end 520, has an inside diameter 571 (e.g., 0.018 inches), a depth 573 (e.g., 0.079), and is sized and configured to receive a portion of another segment 510 (e.g., stem 572). The stem 572 extends from the first end 520 toward the second end 522, has an outside diameter 575 (e.g., 0.017 inches), a length 577 (e.g., 0.078 inches), and is sized and configured to be received by a portion of another segment 510 (e.g., recess 570). The outside diameter 575 is less than the inside diameter 571 and the length 577 is less than the depth 573. The main body 524 has a first outside diameter 527 (e.g., 0.024 inches) between the second end 522 and the stem 572 that is greater than the inside diameter 571 and the outside diameter 575. As shown in the illustrated embodiment, each segment has chamfered and beveled edges to avoid damaging the segment coating 528 during attachment of the segments to one another. Alternative embodiments, however, can include other types of edges, or combinations of edges, such as rounded, beveled, squared, or chamfered. The adjacent segments 530, 532 are insulated from one another using the segment coating 528.

A segment coating 528 can have any suitable thickness and selection of a suitable thickness can be based on various considerations, including the intended use of a wireguide. Examples of thicknesses considered suitable for a segment coating include thicknesses equal to, greater than, less than, or about 0.0001 inches, 0.0002 inches, 0.0003 inches, 0.0004 inches, 0.0005 inches, thicknesses greater than 0.0005 inches, thicknesses less than 0.0001 inches, thicknesses between about 0.0001 inches and about 0.005 inches, thicknesses between about 0.0002 inches and about 0.003 inches, and any other thickness considered suitable for a particular embodiment. In the illustrated embodiment, the segment coating 528 has a thickness 529 between about 0.0001 inches and about 0.0005 inches.

In the illustrated embodiment, the wireguide 500 can be assembled by applying an adhesive to a stem 572 and/or within a recess 570 of each segment 510, positioning the stem 572 defined by a first segment 530 within a recess 570 defined by a second segment 532, applying a force on each of the segments toward one another to join the adjacent segments 510 to one another. This results in a portion of the first segment 510 (e.g., stem 572) being disposed within the recess 570 defined by the second segment 510. This process is repeated until a desired wireguide length is achieved. Subsequently, the wire guide coating is applied to the segments 510.

The structural arrangement of example wireguide 500 is considered advantageous at least because it was thought to be difficult due to the operations required to form a cylindrical recess within an end of a segment. For example, Nitinol wires are very difficult to machine by conventional machining techniques such as drilling, turning, and milling. However, laser machining (e.g., using an Electric Discharge Machine (EDM)) can be utilized to create the structure illustrated on segments 510. Such processing results in a segment that defines a textured surface on the stem and the walls defining the recess such that a strong bond with an adhesive can be achieved (e.g., using epoxy). The structural arrangement of example wireguide 500 is also considered advantageous at least because it facilitates extruding the wireguide coating over the segments 510 that have the same outside diameter and avoids challenges associated with extruding a wireguide coating over diameter changes, or steps, along the length of a wireguide.

FIGS. 23, 24, 25, 26, 27, 28, and 29 illustrate another example wireguide 600. The wireguide 600 is similar to the wireguide 100 illustrated in FIGS. 1, 2, 3, and 4 and described above, except as detailed below. The wireguide 600 has a segmented construction and includes a series 608 of individual segments 610, a plurality of connectors 612, and a wireguide coating 616.

In the illustrated embodiment, the main body 624 defines an elongate member 634, a first step 670 between the first end 620 and the second end 622, and a second step 672 between the first step 670 and the second end 622. The main body 624 has a first outside diameter 627 (e.g., 0.018 inches) between the first step 670 and the second step 672, a second outside diameter 671 (e.g., 0.0140 inches) between the first step 670 and the first end 620, and a third outside diameter 673 (e.g., 0.0140 inches) between the second step 672 and the second end 622. The first outside diameter 627 is greater than the second outside diameter 671 and the third outside diameter 673. In the illustrated embodiment, the second outside diameter 671 and the third outside diameter 673 are equal. However, in alternative embodiments, a second outside diameter can be different than a third outside diameter. This structural arrangement results in the formation of a first stem 674 and a second stem 676. The first stem 674 extends from the first end 620 to the first step 670 and the second stem 676 extends from the second end 622 to the second step 672. Each of the first stem 674 and the second stem 676 has a length 675 (e.g., 0.090 inches). However, in alternative embodiments, the length of a first stem can be different than the length of a second stem. The adjacent segments 630, 632 are insulated from one another using a connector of the plurality of connectors 612, as described in more detail herein. In the illustrated embodiment, each segment of the individual segments 610 omits the inclusion of a segment coating. However, alternative embodiments could include a segment coating on each, or a plurality, of segments of individual segments included in a wireguide.

In the illustrated embodiment, each connector of the plurality of connectors 612 is formed of a non-conductive material (e.g., polymeric, PEEK, reinforced PEEK, polybenzimidazole (Celazole) tubing, fiberglass, toughened fiberglass, Quartz, ceramic composites, oriented fiber polishing stones), has a main body 644 that defines a first recess 678, a second recess 680, and an outside diameter 647 that is equal to the first outside diameter 627 of a segment 610 such that the outer surface 646 is flush with the outer surface 626 of the adjacent segments 630, 632 connected by the particular connector 612. Alternatively, an outside diameter of a connector can vary (e.g., between about 0.018 inches and about 0.023 inches). The first recess 678 extends into the main body 644 from the first end 640 toward the second end 642. The second recess 680 extends into the main body 644 from the second end 642 toward the first end 640. Each of the first recess 678 and the second recess 680 has an inside diameter 679 (e.g., 0.015 inches) that is sized and configured to receive a portion of a segment. The length 643 of each connector 612 can vary depending on the material that forms the connector. When a connector is formed of a relatively stiff material, the length of the connector should be shorter than if the connector were formed of a relatively flexible material to avoid the creation of stiff portions of the wireguide that are not as flexible as a segment included in the wireguide.

In the illustrated embodiment, the wireguide 600 can be assembled by applying an adhesive to within the first recess 678 and second recess 680 defined by a connector of the plurality of connectors 612, positioning an end of a first segment 630 within the first recess 678, positioning an end of a second segment 632 within the second recess 680, and applying a force on each of the segments toward one another to join the adjacent segments 630, 632 to one another using the connector 612. This results in a portion of each of the first and second segments 630, 632 being disposed within the connector 612. Alternatively, or in combination with the assembly described above, an adhesive can be applied to each of the stems of the adjacent segments intended to be joined to one another. This process is repeated until a desired wireguide length is achieved. Subsequently, a wireguide coating 616 is applied to the segments 610 and connectors 612.

The structural arrangement of example wireguide 600 is considered advantageous at least because it facilitates extruding the wireguide coating 616 over the segments 610 and connectors 614 that have the same outside diameter and avoids challenges associated with extruding a wireguide coating over diameter changes, or steps, along the length of a wireguide. In addition, it is considered advantageous that the material that forms the connectors 612 is not recognized as a "flat" portion along the wire such that it is flexible (e.g., as flexible as the material that forms a segment). In alternative embodiments, if the material that forms a connector is stiff it should be as short as possible to avoid the undesirable feel of a stiff connector section.

FIGS. 30, 31, 32, 33, and 34 illustrate another example wireguide 700. The wireguide 700 is similar to the wireguide 100 illustrated in FIGS. 1, 2, 3, and 4 and described above, except as detailed below. The wireguide 700 has a segmented construction and includes a series 708 of individual segments 710, a plurality of connectors 712, and a wireguide coating 716.

In the illustrated embodiment, the main body 724 defines an elongate member 734, a first step 770 between the first end 720 and the second end 722, a second step 772 between the first step 770 and the second end 722, a first dovetailed portion 774, and a second dovetailed portion 776. The main body 724 has a first outside diameter 727 (e.g., 0.018 inches) between the first step 770 and the second step 772, a second outside diameter 771 (e.g., 0.016 inches) between the first step 770 and the first dovetailed portion 774 and along a length (e.g., 0.021 inches) of the segment 710, and a third outside diameter 773 (e.g., 0.016 inches) between the second step 772 and the second dovetailed portion 776 and along a length (e.g., 0.021 inches) of the segment 710. The first outside diameter 727 is greater than the second outside diameter 771 and the third outside diameter 773. In the illustrated embodiment, the second outside diameter 771 and the third outside diameter 773 are equal. However, in alternative embodiments, a second outside diameter can be different than a third outside diameter. The first dovetailed portion 774 extends from the first end 720 toward the second end 722 and has a length 775 (e.g., 0.118 inches), a width 777, and a height 779. Each of the width 777 and the height 779 tapers from the first end 720 toward the second end 722. The height 779 tapers from a first height at the first end 720 (e.g., 0.011 inches) to a second height at the second end of the first dovetailed portion 774 (e.g., 0.007 inches). The second dovetailed portion 776 extends from the second end 722 toward the first end 720 and has a length, width, and height that is the same as the first dovetailed portion 774. The adjacent segments 730, 732 are insulated from one another using the segment coating 728 and a connector of the plurality of connectors 712.

In the illustrated embodiment, the wireguide 700 can be assembled by positioning an end of a first segment 730 within the passageway 748 of a connector, positioning an end of a second segment 732 within the passageway 748, applying a force on each of the segments toward one another to join the adjacent segments 710 to one another, and, when crimping is being utilized to attach the connector to the adjacent segments, crimping the connector to the adjacent segments 730, 732. This results in a portion of each of the first and second segments 730, 732 being disposed within the passageway 748 of the connector 712. This process is repeated until a desired wireguide length is achieved. Subsequently, a wireguide coating 716 is applied to the segments 710 and connectors 712.

The structural arrangement of example wireguide 700 is considered advantageous at least because it facilitates extruding the wireguide coating 716 over the segments 710 and connectors 714 that have the same outside diameter and avoids challenges associated with extruding a wireguide coating over diameter changes, or steps, along the length of a wireguide. The structural arrangement of a segment, or a plurality of segments, can be formed using any suitable technique or method of manufacture and selection of a suitable technique or method of manufacture can be based on various considerations, including the intended use of a wireguide. Examples of techniques and methods of manufacture considered suitable to form a segment, or a plurality of segments, include grinding, using an EDM machine, laser-cutting, those described herein, and any other technique or method considered suitable for a particular embodiment.

FIGS. 35, 36, 37, 38, and 39 illustrate another example wireguide 800. The wireguide 800 is similar to the wireguide 700 illustrated in FIGS. 30, 31, 32, 33, and 34 and described above, except as detailed below. The wireguide 800 has a segmented construction and includes a series 808 of individual segments 810, a plurality of connectors 812, and a wireguide coating 816.

In the illustrated embodiment, the main body 824 defines an elongate member 834, a first dovetailed portion 874, and a second dovetailed portion 876. The main body 824 has a first outside diameter 827 (e.g., 0.018 inches) between the first end 820 and the second end 822. The first dovetailed portion 874 extends from the first end 820 toward the second end 822 and the second dovetailed portion 876 extends from the second end 822 toward the first end 820. In the illustrated embodiment, each connector of the plurality of connectors 812 is a tubular member that has a wall thickness between about 0.002 inches and about 0.003 inches.

FIGS. 40, 41, 42, 43, and 44 illustrate another example wireguide 900. The wireguide 900 is similar to the wireguide 100 illustrated in FIGS. 1, 2, 3, and 4 and described above, except as detailed below. The wireguide has a segmented construction and includes a series 908 of individual segments 910, a plurality of connectors 912, a plurality of spacers 914, and a wireguide coating 916.

In the illustrated embodiment, the main body 924 defines an elongate member 934, a first step 970 between the first end 920 and the second end 922, a second step 972 between the first step 970 and the second end 922, a first saw-toothed section 974, and a second saw-toothed section 976. The main body 924 has a first outside diameter 927 (e.g., 0.020 inches) between the first step 970 and the second step 972, a second outside diameter 971 (e.g., 0.018 inches) between the first step 970 and the first saw-toothed section 974 and along a length (e.g., 0.010 inches) of the segment 910, and a third outside diameter 973 (e.g., 0.018 inches) between the second step 972 and the second saw-toothed section 976 and along a length (e.g., 0.010 inches) of the segment 910. The first outside diameter 927 is greater than the second outside diameter 971 and the third outside diameter 973. In the illustrated embodiment, the second outside diameter 971 and the third outside diameter 973 are equal. However, in alternative embodiments, a second outside diameter can be different than a third outside diameter. The first saw-toothed section 974 extends from the first end 920 toward the second end 922 and has a length 975 (e.g., 0.115 inches) and a height 977 (e.g., 0.008). The teeth 978 of the first saw-toothed section 974 have a tooth depth 979 (e.g., 0.005) and a gullet angle 980 (e.g., 90 degrees). The second saw-toothed section 976 extends from the second end 922 toward the first end 920 and has a length, a height, a tooth depth, and a gullet angle that are the same as those of the first saw-toothed section. The adjacent segments 930, 932 are insulated from one another using the segment coating 928, a connector of the plurality of connectors 912, and a spacer of the plurality of spacers 914. In an alternative embodiment, a first step and a second step can be omitted.

In the illustrated embodiment, a portion of adjacent segments 910 is disposed within the passageway 948 defined by a connector of the plurality of connectors 912 such that the adjacent segments 910 are joined to one another. Each of the connectors 912 comprises a tubular member 949 that has an outside diameter 947 that is equal to the outside diameter 927 of the adjacent segments 930, 932. In the illustrated embodiment, a spacer of the plurality of spacers 914 is disposed between each of the saw-toothed sections 974, 976 of adjacent segments 910 and comprises an elongated sheet formed of an insulating material, such as PEEK. In an alternative embodiment, a plurality of spacers can be omitted from a wireguide.

In the illustrated embodiment, the wireguide 900 can be assembled by positioning a spacer on a first saw-toothed section 974 of a first segment 930, mating the first saw-toothed section 974 with a second saw-toothed section 976 of a second segment 932, positioning a connector 912 over the saw-toothed sections 974, 976 and attaching the connector to the adjacent segments. This results in a portion of each of the first and second segments 930, 932 being disposed within the passageway 948 of the connector 912. This process is repeated until a desired wireguide length is achieved. Subsequently, the wireguide coating 916 is applied to the segments 910 and connectors 912.

The structural arrangement of example wireguide 900 is considered advantageous at least because it facilitates extruding the wireguide coating 916 over the segments 910 and connectors 914 that have the same outside diameter and avoids challenges associated with extruding a wireguide coating over diameter changes, or steps, along the length of a wireguide. In addition, the structural arrangement of example wireguide 900 is considered advantageous at least because it provides an interlocking structure that prevents axial movement of adjacent segments relative to one another during use.

FIGS. 45, 46, 47, 48, and 49 illustrate another example wireguide 1000. The wireguide 1000 is similar to the wireguide 100 illustrated in FIGS. 1, 2, 3, and 4 and described above, except as detailed below. The wireguide has a segmented construction and includes a series 1008 of individual segments 1010, a plurality of connectors 1012, a plurality of spacers 1014, and a wireguide coating 1016.

In the illustrated embodiment, the main body 1024 defines an elongate member 1034, a first stem 1070, and a second stem 1072. The main body 1024 has a first outside diameter 1027 (e.g., 0.018 inches) between the first stem 1070 and the second stem 1072. The first stem 1070 extends from the first end 1020 toward the second end 1022 and has a length 1075 (e.g., 0.1605 inches), a step 1076, a step length 1077 (e.g., 0.079), a first height 1079 (e.g., 0.011), and a second height 1081 (e.g., 0.0045). The second stem 1072 extends from the second end 1022 toward the first end 1020 and has a length 1083 (e.g., 0.1605 inches), a step 1078, a step length 1085 (e.g., 0.079), a first height 1087 (e.g., 0.011), and a second height 1089 (e.g., 0.0045). Each of the first stem 1070 and the second stem 1072 is not continuous with the outer surface 1026 of the segment 1010 on which it is formed. The adjacent segments 1030, 1032 are insulated from one another using the segment coating 1028, a connector of the plurality of connectors 1012, and a spacer of the plurality of spacers 1014.

In the illustrated embodiment, a portion of adjacent segments 1010 is disposed within the passageway 1048 defined by a connector of the plurality of connectors 1012 such that the adjacent segments 1010 are joined to one another. Each of the connectors 1012 comprises a tubular member 1049 that has an outside diameter that is equal to the outside diameter of the adjacent segments 1030, 1032. In the illustrated embodiment, a spacer of the plurality of spacers 1014 is disposed between each of the stems 1070, 1072 of adjacent segments 1010 and comprises an elongated sheet formed of an insulating material. In an alternative embodiment, a plurality of spacers can be omitted from a wireguide.

In the illustrated embodiment, the wireguide 1000 can be assembled by positioning a spacer 1014 on a first stem 1070 of a first segment 1030, mating the first stem 1070 with a second stem 1072 of a second segment 1032, positioning a connector 1012 over the stems 1070, 1072 and attaching the connector to the adjacent segments 1030, 1032. This results in a portion of each of the first and second segments 1030, 1032 being disposed within the passageway of the connector 1012. This process is repeated until a desired wireguide length is achieved. Subsequently, a wireguide coating 1016 is applied to the segments 1010 and connectors 1012.

The structural arrangement of example wireguide 1000 is considered advantageous at least because it facilitates extruding the wireguide coating 1016 over the segments 1010 and connectors 1014 that have the same outside diameter and avoids challenges associated with extruding a wireguide coating over diameter changes, or steps, along the length of a wireguide. In addition, the structural arrangement of example wireguide 1000 is considered advantageous at least because it provides an interlocking structure to prevent axial movement of adjacent segments relative to one another during use.

FIGS. 50, 51, and 52 illustrate another example wireguide 1100. The wireguide 1100 is similar to the wireguide 1000 illustrated in FIGS. 45, 46, 47, 48, and 49 and described above, except as detailed below. The wireguide 1100 has a segmented construction and includes a series 1108 of individual segments 1110, a plurality of connectors 1112, a plurality of spacers 1114, and a wireguide coating.

In the illustrated embodiment, each of the first stem 1170 and the second stem 1172 is continuous with the outer surface 1126 of the segment 1110 on which it is formed. The main body 1124 has a first outside diameter 1127 (e.g., 0.024 inches) between the first stem 1170 and the second stem 1172. The first stem 1170 extends from the first end 1120 toward the second end 1122 and has a length 1175 (e.g., 0.161 inches), a step 1176, a step length 1177 (e.g., 0.079), a first height 1179 (e.g., 0.013), and a second height 1181 (e.g., 0.014). The second stem 1172 extends from the second end 1122 toward the first end 1120 and has a length 1183 (e.g., 0.161 inches), a step 1178, a step length 1185 (e.g., 0.079), a first height 1187 (e.g., 0.013), and a second height 1189 (e.g., 0.014). The adjacent segments 1130, 1132 are insulated from one another using the segment coating 1128, a connector of the plurality of connectors 1112, and a spacer of the plurality of spacers 1114.

In the illustrated embodiment, a portion of adjacent segments 1110 is disposed within the passageway 1148 defined by a connector of the plurality of connectors 1112 such that the adjacent segments 1110 are joined to one another. Each of the connectors 1112 comprises a tubular member 1149 that has an outside diameter 1147 that is greater than the outside diameter 1127 of the adjacent segments 1130, 1132. In the illustrated embodiment, a spacer of the plurality of spacers 1114 is disposed between each of the stems 1170, 1172 of adjacent segments 1130, 1132 and comprises an elongated sheet formed of an insulating material. In an alternative embodiment, a plurality of spacers can be omitted from a wireguide.

The structural arrangement of example wireguide 1100 is considered advantageous at least because it provides an interlocking structure to prevent axial movement of adjacent segments relative to one another during use.

FIGS. 53, 54, 55, 56, 57, 58, 59, 60, and 61 illustrate another example wireguide 1200. The wireguide 1200 is similar to the wireguide 100 illustrated in FIGS. 1, 2, 3, and 4 and described above, except as detailed below. The wireguide 1200 has a segmented construction and includes a series 1208 of individual segments 1210, a plurality of connectors 1212, and a wireguide coating 1216.

In the illustrated embodiment, the main body 1224 defines an elongate member 1234, a first step 1270 between the first end 1220 and the second end 1222, a second step 1272 between the first step 1270 and the second end 1222, a first helical ground segment 1274, and a second helical ground segment 1276. The main body 1224 has a first outside diameter 1227 (e.g., 0.020 inches) between the first step 1270 and the second step 1272, a second outside diameter 1271 (e.g., 0.016 inches) along the first helical ground segment 1274, and a third outside diameter 1273 (e.g., 0.016 inches) along the second helical ground segment 1276. The first outside diameter 1227 is greater than the second outside diameter 1271 and the third outside diameter 1273. In the illustrated embodiment, the second outside diameter 1271 and the third outside diameter 1273 are equal. However, in alternative embodiments, a second outside diameter can be different than a third outside diameter. The adjacent segments 1230, 1232 are insulated from one another using a connector of the plurality of connectors 1112. In this embodiment, the segments 1210 omit the inclusion of a segment coating. However, any of the embodiments described herein can include a segment coating along any suitable portion of a segment (e.g., along an end, along a portion of the length extending from a first end toward a second end a distance equal to, greater than, less than, or about one half, one quarter, one third, or one fourth of the length of a segment).

In the illustrated embodiment, each connector of the plurality of connectors 1212 is formed of a non-conductive material (e.g., polymeric, PEEK, reinforced PEEK, polybenzimidazole (Celazole) tubing, fiberglass, toughened fiberglass, Quartz, ceramic composites, oriented fiber polishing stones), has a main body 1244 that defines a first recess 1278, a second recess 1280, and an outside diameter 1247 that is equal to the first outside diameter 1227 of a segment 1210 such that the outer surface 1246 is flush with the outer surface 1226 of the adjacent segments 1230, 1232 connected by the particular connector 1212. The first recess 1278 extends into the main body 1244 from the first end 1240 toward the second end 1242. The second recess 1280 extends into the main body 1244 from the second end 1242 toward the first end 1240. Each of the first recess 1278 and the second recess 1280 has an inside diameter 1279 that is less than the second outside diameter 1271 and the third outside diameter 1273 (e.g., 0.017 inches, less than 0.017 inches) and a depth 1281 (e.g., 0.130) that is sized and configured to receive a portion of a segment.

In the illustrated embodiment, the wireguide 1200 can be assembled by applying an adhesive to within the first recess 1278 and second recess 1280 defined by a connector of the plurality of connectors 1212, rotating an end of a first segment 1230 within the first recess 1278 such that it advances into the first recess 1278, and rotating an end of a second segment 1232 within the second recess 1280 such that it advances into the second recess 1280. This results in a portion of each of the first and second segments 1210 being disposed within the connector 1212. Alternatively, an adhesive can be omitted from the attachment between adjacent segments and a connector since the helical segments provide attachment between the segments and the connector. This process is repeated until a desired wireguide length is achieved. Subsequently, the wireguide coating 1216 is applied to the segments 1210 and connectors 1212.

The structural arrangement of example wireguide 1200 is considered advantageous at least because it facilitates extruding the wireguide coating 1216 over the segments 1210 and connectors 1214 that have the same outside diameter and avoids challenges associated with extruding a wireguide coating over diameter changes, or steps, along the length of a wireguide. In addition, the structural arrangement of example wireguide 1200 is considered advantageous at least because it allows for attachment via interaction with the threads defined by each segment and a connector (e.g., non-conductive), which prevents the segments from backing out of the connector and provides a complete lack of conductivity between adjacent wire segments. In addition, this structural arrangement does not require use of a spacer or a segment coating. However, alternative embodiments can include a spacer, or a plurality of spacers, and a segment coating on each, or a portion, of a series of segments included in a wireguide.

Figure 62:
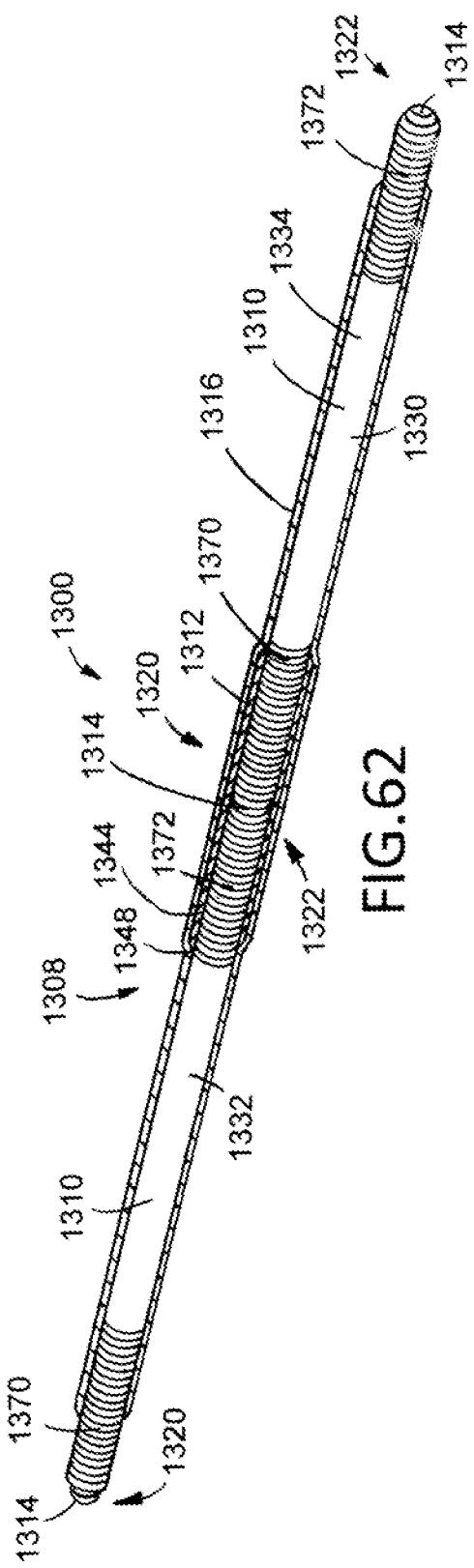
FIG. 62 is a perspective view of a portion of another example interventional wireguide partially broken away.

FIG. 62 illustrates another example wireguide 1300. The wireguide 1300 is similar to the wireguide 100 illustrated in FIGS. 1, 2, 3, and 4 and described above, except as detailed below. The wireguide 1300 has a segmented construction and includes a series 1308 of individual segments 1310, a plurality of connectors 1312, a plurality of spacers 1314, and a wireguide coating 1316.

In the illustrated embodiment, the main body 1324 defines an elongate member 1334, a first threaded portion 1370 that extends from the first end 1320 toward the second end 1322 and a second threaded portion 1372 that extends from the second end 1322 toward the first end 1320. Each of the first threaded portion 1370 and the second threaded portion 1372 defines micro-threads in the range of 0000-160 or 000-120 that are formed by rolling the segments. However, other types of threads and techniques or methods of forming threads on a segment can be utilized. This use of threads on a segment is considered advantageous at least because it imparts texture to a surface of the segment to aid in securement to a connector.

In the illustrated embodiment, each connector of the plurality of connectors 1312 is formed of a non-conductive material (e.g., polymeric, PEEK, reinforced PEEK, polybenzimidazole (Celazole) tubing, fiberglass, toughened fiberglass, Quartz, ceramic composites, oriented fiber polishing stones) and has a main body 1344 that defines a passageway 1348 that extends through the connector. In the illustrated embodiment, a spacer of the plurality of spacers 1314 is disposed between adjacent segments 1310 and comprises a disc member formed of an insulating material (e.g., PEEK, ceramic, fiber-filled polymer). In an alternative embodiment, such that those in which each segment includes a segment coating, a plurality of spacers can be omitted from a wireguide.

In the illustrated embodiment, the wireguide 1300 can be assembled by applying an adhesive within the passageway 1348 defined by a connector of the plurality of connectors 1312, rotating an end of a first segment 1330 within the passageway 1348 such that it advances into the passageway 1348, and rotating an end of a second segment 1332 within the passageway 1348 such that it advances into the passageway 1348. This results in a portion of each of the first and second segments 1330, 1332 being disposed within the connector 1312. Alternatively, an adhesive can be omitted from the attachment between adjacent segments and a connector since the threaded portion provides attachment between the segments and the connector. This process is repeated until a desired wireguide length is achieved. Subsequently, the wireguide coating 1316 is applied to the segments 1310 and the connectors 1312.

The structural arrangement of example wireguide 1300 is considered advantageous at least because it allows for attachment via interaction with the threads defined by each segment and a connector (e.g., non-conductive), which prevents the segments from backing out of the connector and increases tensile strength. In addition, this structural arrangement does not require use of a segment coating.

FIGS. 63 and 64 illustrate another example wireguide 1400. The wireguide 1400 is similar to the wireguide 100 illustrated in FIGS. 1, 2, 3, and 4 and described above, except as detailed below. The wireguide 1400 has a segmented construction and includes a series 1408 of individual segments 1410, a plurality of connectors 1412, a plurality of spacers 1414, a wireguide coating 1416, and a plurality of pins 1470.

In the illustrated embodiment, the main body 1424 defines an elongate member 1434, a first passageway 1472 that extends through the main body 1424 and a second passageway 1474 that extends through the main body 1424. Each of the passageways can have any suitable inside diameter. Examples of inside diameters considered suitable include inside diameters that are equal to, less than, greater than, or about 0.010 inches, inside diameters between about 0.05 and about 0.015 inches, and any other inside diameter considered suitable for a particular embodiment. The adjacent segments 1430, 1432 are insulated from one another using a connector of the plurality of connectors 1412, a spacer of the plurality of spacers 1414, and a plurality of pins 1470.

In the illustrated embodiment, each connector of the plurality of connectors 1412 is formed of a non-conductive material (e.g., polymeric, PEEK, reinforced PEEK, polybenzimidazole (Celazole) tubing, fiberglass, toughened fiberglass, Quartz, ceramic composites, oriented fiber polishing stones) and has a main body 1444 that defines a first passageway 1448 that extends through the connector and a plurality of passageways 1482 that extend through the main body 1444 and are in communication with the first passageway 1448. In the illustrated embodiment, a spacer of the plurality of spacers 1414 is disposed between adjacent segments 1410 and comprises a disc member formed of an insulating material (e.g., PEEK, ceramic, fiber-filled polymer). In an alternative embodiment, in which increased electrical insulation is not desired, a plurality of spacers can be omitted from a wireguide.

Each pin of the plurality of pins 1470 has a main body 1476 that defines an elongate member sized and configured to be received by a passageway 1472, 1474 defined by a segment and a passageway of the plurality of passageways 1482 defined by a connector 1412. In the illustrated embodiment, a first pin 1478 is disposed within the first passageway 1472 and a second pin 1480 is disposed within the second passageway 1474. Each of the pins of the plurality of pins 1470 has an outside diameter that is slightly larger than the inside diameter of a passageway and can be formed of any suitable material, such as those described herein with respect to a segment, a connector, and/or a spacer. For example, in the illustrated embodiment, each pin of the plurality of pins 1470 is formed of an electrically insulating material (e.g., electrically non-conductive material). However, alternative embodiments can include pins that have outside diameters that are less than an inside diameter of a passageway and/or that are formed of any suitable material, such as an electrically conductive material, and include a pin coating, such as those described with respect to a segment coating and/or a wireguide coating.

In the illustrated embodiment, the wireguide 1400 can be assembled by positioning a spacer between adjacent segments, advancing a connector over the segments such that each passageway of the plurality of passageways 1482 is aligned with a passageway 1472, 1474 defined by a segment, advancing a first pin 1478 through a first passageway of the plurality of passageways 1482, the first passageway 1472, and a second passageway of the plurality of passageways 1482, and advancing a second pin 1480 through a third passageway of the plurality of passageways 1482, the second passageway 1474, and a fourth passageway of the plurality of passageways 1482. This results in a portion of each of the first and second segments 1410 and a spacer of the plurality of spacers 1414 being disposed within the connector 1412. Alternatively, an adhesive can be applied within a passageway defined by a segment and/or connector to increase attachment between adjacent segments and a connector and/between a pin and a connector and/or segment. This process is repeated until a desired wireguide length is achieved. Subsequently, the wireguide coating 1416 is applied to the segments 1410 and connectors 1412.

The structural arrangement of example wireguide 1400 is considered advantageous at least because it allows for attachment via interaction with the pins disposed through each segment and connector (e.g., non-conductive), which prevents the segments from moving axially relative to one another. In addition, this structural arrangement doesn't require use of an adhesive, but an adhesive could be utilized if desired.

FIGS. 65, 66, 67, and 68 illustrate another example wireguide 1500. The wireguide 1500 is similar to the wireguide 100 illustrated in FIGS. 1, 2, 3, and 4 and described above, except as detailed below. The wireguide 1500 has a segmented construction and includes a series 1508 of individual segments 1510, a plurality of connectors 1512, a plurality of spacers 1514, and a wireguide coating 1516.

In the illustrated embodiment, the main body 1524 defines an elongate member 1534, a first plurality of skived cuts 1570, and a second plurality of skived cuts 1572. Each of the skived cuts 1570, 1572 defines an area where a portion of the main body 1524 has been removed. The first plurality of skived cuts 1570 is defined between the first end 1520 and the second end 1522 and the second plurality of skived cuts 1572 is defined between the first plurality of skived cuts 1570 and the second end 1522. The area removed by each of the skived cuts 1570, 1572 has a thickness 1571 (e.g., 0.002 inches) and a length 1573 (e.g., 0.012). Each of the skived cuts 1570, 1572 is offset from an adjacent skive cut at an angle (e.g., 90 degrees), and is disposed a distance 1577 (e.g., 0.044 inches) from an end 1520, 1522. Each skived cut can be formed using any suitable technique or method, such as laser technology. While skived cuts have been illustrated, a main body can define any suitable structural arrangement that defines a void in the main body (e.g., passageway through main body, cut into main body, blind hole, recess).

In the illustrated embodiment, each connector of the plurality of connectors 1512 has a main body 1544 that defines a first passageway 1548 that extends through the connector and a plurality of passageways 1582 that extend through the main body 1544 and are in communication with the first passageway 1548. Each passageway of the plurality of passageways 1582 can be formed using any suitable technique or method, such as laser technology. In the illustrated embodiment, a spacer of the plurality of spacers 1514 is disposed between adjacent segments 1530, 1532 and comprises a disc member formed of an insulating material (e.g., PEEK, ceramic, fiber-filled polymer). In an alternative embodiment, in which increased electrical insulation is not desired, a plurality of spacers can be omitted from a wireguide.

In the illustrated embodiment, the wireguide 1500 can be assembled by positioning a spacer between adjacent segments 1530, 1532, advancing a connector over the segments such that each passageway of the plurality of passageways 1582 is aligned with a skived cut 1570, 1572 defined by a segment, and applying an adhesive within each passageway of the plurality of passageways 1582 such that the adhesive is disposed within the void created by the skived cuts 1570, 1572. This results in a portion of each of the first and second segments 1530, 1532 and a spacer of the plurality of spacers 1514 being disposed within the connector 1512. This process is repeated until a desired wireguide length is achieved. Subsequently, the wireguide coating 1516 is applied to the segments 1510 and the connectors 1512.

The structural arrangement of example wireguide 1500 is considered advantageous at least because it allows for attachment via interaction between the adhesive disposed within the voids created by the skived cuts, the segments, and the connector. In addition, this structural arrangement results in an increase in strength of the wireguide 1500 and is believed to contribute to an extremely high tensile force between the segments and connectors.

FIGS. 69 and 70 illustrate another example wireguide 1600. The wireguide 1600 is similar to the wireguide 100 illustrated in FIGS. 1, 2, 3, and 4 and described above, except as detailed below. The wireguide 1600 has a segmented construction and includes a series 1608 of individual segments 1610, a plurality of connectors 1612, a plurality of spacers 1614, and a wireguide coating 1616.

In the illustrated embodiment, each connector of the plurality of connectors 1612 has a main body 1644 that defines a first passageway 1648 that extends through the connector and a plurality of passageways 1682 that extend through the main body 1644 and are in communication with the first passageway 1648. Each passageway of the plurality of passageways 1682 can be formed using any suitable technique or method, such as laser technology. In the illustrated embodiment, a spacer of the plurality of spacers 1614 is disposed between adjacent segments 1610 and comprises a disc member formed of an insulating material (e.g., PEEK, ceramic, fiber-filled polymer). In an alternative embodiment, in which increased electrical insulation is not desired, a plurality of spacers can be omitted from a wireguide.

In the illustrated embodiment, the wireguide 1600 can be assembled by positioning a spacer between adjacent segments, advancing a connector over the segments such that each passageway of the plurality of passageways 1682 is disposed over a segment 1610, and applying an adhesive within each passageway of the plurality of passageways 1682 such that the adhesive contacts a segment. This results in a portion of each of the first and second segments 1630, 1632 and a spacer of the plurality of spacers 1614 being disposed within the connector 1612. This process is repeated until a desired wireguide length is achieved. Subsequently, the wireguide coating 1616 is applied. The adhesive can be introduced into the plurality of passageways 1682 using any suitable technique or method, such as capillary action, an adhesive application pump (e.g., Nordson EFD Fluid Dispensing Systems), or any other technique or method considered suitable for a particular embodiment.

The structural arrangement of example wireguide 1600 is considered advantageous at least because it allows for attachment via interaction between the adhesive, the segment coating 1628, and connector 1612.

FIGS. 71, 72, 73, and 74 illustrate another example wireguide 1700. The wireguide 1700 is similar to the wireguide 100 illustrated in FIGS. 1, 2, 3, and 4 and described above, except as detailed below. The wireguide 1700 has a segmented construction and includes a series 1708 of individual segments 1710, a plurality of connectors 1712, a plurality of spacers 1714, and a wireguide coating 1716.

In the illustrated embodiment, the main body 1724 defines an elongate member 1734, a first plurality of recesses 1770, and a second plurality of recesses 1772. Each of the recesses 1770, 1772 defines an area where a portion of the main body 1724 has been removed and has a hemispheroid configuration (e.g., half egg-shaped configuration). However, alternative embodiments, can define recesses that have any suitable configuration. The first plurality of recesses 1770 is defined between the first end 1720 and the second end 1722 and the second plurality of recesses 1772 is defined between the first plurality of recesses 1770 and the second end 1722. Each of the recesses 1770, 1772 has a radius of curvature 1771 (e.g., 0.008 inches). Each recess can be formed using any suitable technique or method, such as laser technology, grinding, or any other technique or method considered suitable for a particular embodiment.

In the illustrated embodiment, each connector of the plurality of connectors 1712 has a main body 1744 that defines a first passageway 1748 that extends through the connector and a plurality of passageways 1782 that extend through the main body 1744 and are in communication with the first passageway 1748. Each connector of the plurality of connectors 1712 is formed of an electrically non-conductive material (e.g., PEEK, ceramic, insulated Nitinol tube). Each passageway of the plurality of passageways 1782 can be formed using any suitable technique or method, such as laser technology. In the illustrated embodiment, a spacer of the plurality of spacers 1714 is disposed between adjacent segments 1710 and comprises a disc member formed of an insulating material (e.g., PEEK, ceramic, fiber-filled polymer). In an alternative embodiment, in which increased electrical insulation is not desired, a plurality of spacers can be omitted from a wireguide.

In the illustrated embodiment, the wireguide 1700 can be assembled by positioning a spacer between adjacent segments, advancing a connector over the segments such that a portion of the plurality of passageways 1782, or each passageway of the plurality of passageways 1782, is aligned with a recess of the plurality of recesses 1770, 1772 defined by a segment, and applying an adhesive (e.g., thermoset polymer, epoxy filler) within the portion of the plurality of passageways 1782, or each passageway of the plurality of passageways 1782, aligned with a recess such that the adhesive is disposed within the void created by the recesses 1770, 1772. This results in a portion of each of the first and second segments 1710 and a spacer of the plurality of spacers 1714 being disposed within the connector 1712. This process is repeated until a desired wireguide length is achieved. Subsequently, the wireguide coating 1716 is applied. Alternative embodiments can utilize an adhesive that is compounded with Iron Oxide or other MRI visible material. Optionally, a connector can be rotated subsequent to the application of an adhesive.

The structural arrangement of example wireguide 1700 is considered advantageous at least because it allows for attachment via interaction between the adhesive disposed within the voids created by the recesses, the segments, and the connector. In addition, it increases the surface area to be used as a bonding interlock relative to embodiments that do not include hemispheroid recesses.

FIGS. 75, 76, 77, 78, 79, and 80 illustrate another example wireguide 1800. The wireguide 1800 is similar to the wireguide 100 illustrated in FIGS. 1, 2, 3, and 4 and described above, except as detailed below. The wireguide 1800 has a segmented construction and includes a series 1808 of individual segments 1810, a plurality of connectors 1812, a plurality of spacers 1814, and a wireguide coating 1816.

In the illustrated embodiment, the main body 1824 defines an elongate member 1834, a first plurality of skived cuts 1870, and a second plurality of skived cuts 1872. Each of the skived cuts 1870, 1872 defines an area where a portion of the main body 1824 has been removed. The first plurality of skived cuts 1870 is defined between the first end 1820 and the second end 1822 and the second plurality of skived cuts 1872 is defined between the first plurality of skived cuts 1870 and the second end 1822. Each of the skived cuts 1870, 1872 has a has a thickness 1871 (e.g., 0.003 inches), a length 1873 (e.g., 0.036), opposably positioned from an adjacent skive cut, is cut into the main body 1824 at an angle 1875 (e.g., 5 degrees), and is disposed a distance 1877 (e.g., 0.019 inches) from an end 1820, 1822. Each skived cut can be formed using any suitable technique or method, such as laser technology, grinding, or any other technique or method considered suitable for a particular embodiment.

In the illustrated embodiment, each connector of the plurality of connectors 1812 has a main body 1844 that defines a passageway 1848 that extends through the connector and a plurality of tabs 1882 that are moveable relative to, and within, the main body 1844 and are biased towards a position in which each tab is disposed within the passageway 1848 (e.g., by heat setting). Each connector of the plurality of connectors 1812 is formed of any suitable material, such as those described herein. Each tab of the plurality of tabs 1882 can be formed using any suitable technique or method, such as laser technology. In the illustrated embodiment, a spacer of the plurality of spacers 1814 is disposed between adjacent segments 1810 and comprises a disc member formed of an insulating material (e.g., PEEK, ceramic, fiber-filled polymer). In an alternative embodiment, in which increased electrical insulation is not desired, a plurality of spacers can be omitted from a wireguide.

In the illustrated embodiment, the wireguide 1800 can be assembled by positioning a spacer between adjacent segments and advancing a connector over the segments such that a tab of the plurality of tabs 1882 is disposed with each skive of the plurality of skived cuts 1870, 1872. Optionally, an axial force can be applied on each of the segments to confirm whether they are attached to the connector and/or to position a tab with a skive cut. This results in a portion of each of the first and second segments 1810 and a spacer of the plurality of spacers 1814 being disposed within the connector 1812. This process is repeated until a desired wireguide length is achieved.

The structural arrangement of example wireguide 1800 is considered advantageous at least because it allows for attachment via interaction between the tabs disposed within the voids created by the skive cuts. In this embodiment, a segment coating should be utilized that is strong and resistant to scoring. Each of the segments 1810 and connectors 1812 can be formed of any suitable material, such as nickel-titanium alloys, which are considered particularly advantageous for use in this embodiment.

FIGS. 81, 82, 83, 84, 85, 86, and 87 illustrate another example wireguide 1900. The wireguide 1900 is similar to the wireguide 200 illustrated in FIGS. 5, 6, and 7 and described above, except as detailed below. The wireguide 1900 has a segmented construction and includes a series 1908 of individual segments 1910, a plurality of connectors 1912, a plurality of spacers 1914, and a wireguide coating 1916.

In the illustrated embodiment, the main body 1924 defines an elongate member 1934, a first step 1970 between the first end 1920 and the second end 1922, and a second step 1972 between the first step 1970 and the second end 1922. The main body 1924 has a first outside diameter 1927 (e.g., 0.024) between the first step 1970 and the second step 1972, a second outside diameter 1971 (e.g., 0.020) between the first step 1970 and the first end 1920, and a third outside diameter 1973 (e.g., 0.020) between the second step 1972 and the second end 1922. The first outside diameter 1927 is greater than the second outside diameter 1971 and the third outside diameter 1973. In the illustrated embodiment, the second outside diameter 1971 and the third outside diameter 1973 are equal.

In the illustrated embodiment, each connector of the plurality of connectors 1912 has an outside diameter 1947 that is equal to the first outside diameter 1927 of a segment 1910 such that the outside surface 1946 is flush with the outer surface 1926 of the adjacent segments 1930, 1932 connected by the particular connector 1912. The main body 1944 of each connector 1912 defines a first spiral cut 1974 and a second spiral cut 1976. The first spiral cut 1972 extends from the first end 1940 toward the second end 1942 and the second spiral cut extends from the second end 1942 toward the first end 1940. Each of the spiral cuts 1972, 1974 (e.g., helical coils) extends through the main body 1944. However, alternative embodiments could include a spiral cut that does not extend through the main body of a connector. In the illustrated embodiment, each connector the plurality of connectors 1912 has an inside diameter 1975 (e.g., 0.0205). Alternative embodiments, can include a spiral cut that extends along any suitable length of a connector (e.g., entire length, portion of a length), through any suitable depth of a main body, that has any suitable thread configuration, and/or that has any suitable depth.

The structural arrangement of example wireguide 1900 is considered advantageous at least because it facilitates extruding the wireguide coating 1916 over the segments 1910 and connectors 1914 that have the same outside diameter and avoids challenges associated with extruding a wireguide coating over diameter changes, or steps, along the length of a wireguide. In addition, the structural arrangement of example wireguide 1900 is considered advantageous at least because the spiral cuts 1974, 1976 can act as reservoirs within which adhesives, such as glue, epoxy, or thermosetting resins, can be disposed and/or within which MRI visible wires, such as those formed of Iron Oxide, Gadolinium, or Ferromagnetic Stainless Steel, can be positioned and used as a marker.

FIGS. 88, 89, 90, 91, 92, 93, and 94 illustrate another example wireguide 2000. The wireguide 2000 is similar to the wireguide 1900 illustrated in FIGS. 81, 82, 83, 84, 85, 86, and 87 and described above, except as detailed below. The wireguide 2000 has a segmented construction and includes a series 2008 of individual segments 2010, a plurality of connectors 2012, a plurality of spacers 2014, and a wireguide coating 2016.

In the illustrated embodiment, the main body 2044 of each connector 2012 defines a spiral cut 2074 (e.g., helical coil) that extends between the first end 2040 and the second end 2042 and extends through the main body 2044. In the illustrated embodiment, each connector the plurality of connectors 1912 has an inside diameter 1975 (e.g., 0.020). Alternative embodiments, can include a spiral cut that extends along any suitable length of a connector (e.g., entire length, portion of a length), through any suitable depth of a main body, that has any suitable thread configuration, and/or that has any suitable depth.

The structural arrangement of example wireguide 2000 is considered advantageous at least because it facilitates extruding the wireguide coating 2016 over the segments 2010 and connectors 2014 that have the same outside diameter and avoids challenges associated with extruding a wireguide coating over diameter changes, or steps, along the length of a wireguide. In addition, the structural arrangement of example wireguide 2000 is considered advantageous at least because the spiral cut 2074 can be constructed such that the flexibility and stiffness of the connector matches that of the segments 2010 and can be used to impart features such as curves and angles into the connector, as desired.

FIGS. 95, 96, 97, and 98 illustrate another example wireguide 2100. The wireguide 2100 is similar to the wireguide 100 illustrated in FIGS. 1, 2, 3, and 4 and described above, except as detailed below. The wireguide 2100 has a segmented construction and includes a series 2108 of individual segments 2110, a plurality of connectors 2112, a plurality of spacers 2114, a wireguide coating 2116, and a plurality of connector spacers 2170.

In the illustrated embodiment, the main body 2144 of each connector 2112 defines a spiral cut 2172 (e.g., helical coil) that extends between the first end 2140 and the second end 2142 and extends through the main body 2144. In the illustrated embodiment, each connector the plurality of connectors 2112 has an outside diameter 2173 (e.g., 0.033 inches) and a length 2175 (e.g., between about 9 and about 10 centimeters). Alternative embodiments, can include a spiral cut that extends along any suitable length of a connector (e.g., entire length, portion of a length), through any suitable depth of a main body (e.g., only partially through the thickness of a main body of a connector), that has any suitable thread configuration, and/or that has any suitable depth. Alternatively, or in combination with defining a spiral cut, a connector can define a plurality of slots that extend about the circumference of the connector and through a main body of the connector. Each spacer of the plurality of connector spacers 2170 is disposed between two connectors and is formed of any suitable material (e.g., PEEK).

In the illustrated embodiment, the wireguide 2100 can be assembled by positioning a spacer between each pair of adjacent segments, 2130, 2132, applying a segment coating 2128 over the full length, or a portion of the length, of the series 2008 of segments 2110 and spacers 2114, advancing a connector 2112 over the segments such that it is disposed over adjacent segments 2130, 2132 and a spacer 2114, advancing a first connector spacer 2170 over the segment coating 2128 such that it is disposed adjacent to a first end of the connector 2112, advancing a second connector spacer 2170 over the segment coating 2128 such that it is disposed adjacent to a second end of the connector 2112, advancing a second connector 2112 over the segments such that it is disposed over adjacent segments 2130, 2132 and a spacer 2114 and its first end is disposed adjacent a connector spacer 2170, advancing a third connector spacer 2170 over the segment coating 2128 such that it is disposed adjacent to a second end of the second connector 2112. The steps of advancing a connector over the segments such that it is disposed over adjacent segments and a spacer and its first end is disposed adjacent a connector spacer, advancing a connector spacer over the segment coating such that it is disposed adjacent to a second end of the connector are repeated until a desired wireguide length is achieved. Subsequently, a wireguide coating is applied to the device.

The structural arrangement of example wireguide 2100 is considered advantageous at least because it facilitates extruding the wireguide coating 2116 over the connectors 2114 and connector spacers 2170 that have the same outside diameter and avoids challenges associated with extruding a wireguide coating over diameter changes, or steps, along the length of a wireguide. In addition, the structural arrangement of example wireguide 2100 is considered advantageous at least because the spiral cuts 2172 can act as reservoirs within which adhesives, such as glue, epoxy, or thermosetting resins, can be disposed and/or within which MRI visible wires, such as those formed of Iron Oxide, Gadolinium, or Ferromagnetic Stainless Steel, can be positioned and used as a marker.

Various methods of using an interventional wireguide are described herein. While the methods described herein are shown and described as a series of acts, it is to be understood and appreciated that the methods are not limited by the order of acts, as some acts may in accordance with these methods, occur in the order shown and/or described, in different orders, and/or concurrently with other acts described herein.

Figure 99:
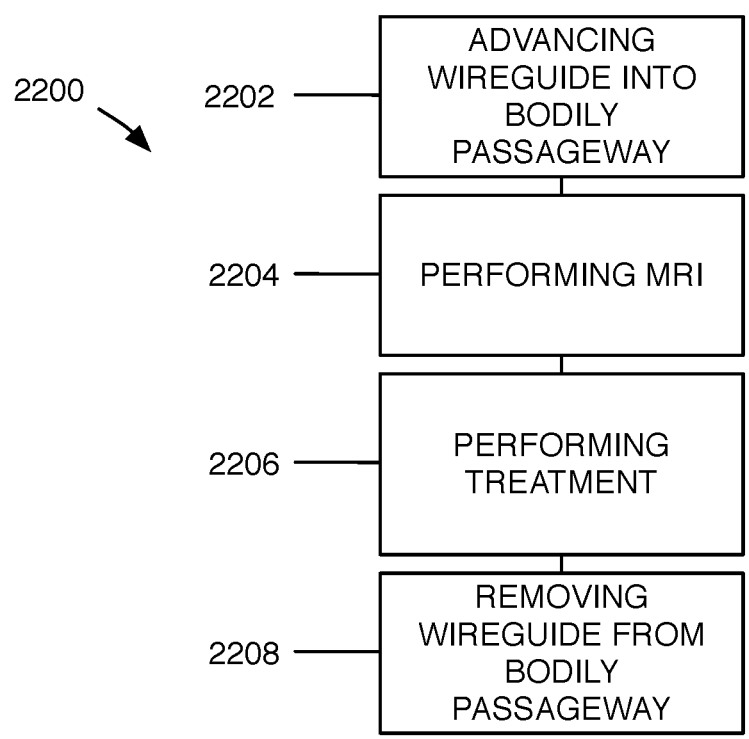
FIG. 99 is a schematic illustration of an example method of using an interventional wireguide.

FIG. 99 is a schematic illustration of an example method 2200 of using an interventional wireguide.

A step 2202 comprises advancing a wireguide into a bodily passageway. Another step 2204 comprises performing MRI. Another step 2206 comprises performing treatment. Another step 2208 comprises removing the wireguide from the bodily passageway.

Step 2202, and any method described herein, can be accomplished using any suitable wireguide capable of being used during performance of an MRI and selection of a suitable wireguide can be based on various considerations, including the material that forms a wireguide and/or the structural arrangement of a wireguide. Examples of wireguides considered suitable to complete a method described herein include wireguide 100, wireguide 200, wireguide 300, wireguide 400, wireguide 500, wireguide 600, wireguide 700, wireguide 800, wireguide 900, wireguide 1000, wireguide 1100, wireguide 1200, wireguide 1300, wireguide 1400, wireguide 1500, wireguide 1600, wireguide 1700, wireguide 1800, wireguide 1900, wireguide 2000, wireguide 2100, and any other wireguide considered suitable for a particular embodiment.

Step 2202 can be accomplished by locating a bodily passageway and applying an axial force on the wireguide toward the bodily passageway until the wireguide (e.g., wireguide distal end) is disposed within the bodily passageway. Optionally, this step can be performed concurrently with step 2204 such that visualization of the wireguide can be accomplished while advancing the wireguide into the bodily passageway. An optional step comprises advancing the wireguide to a point of treatment. This optional step can be accomplished by applying an axial force on the wireguide until the distal end, or a portion of the length, of the wireguide is positioned at, or near, a point of treatment.

Step 2204 can be accomplished by activating a magnetic resonance scanner such that the portion of the bodily passageway containing the wireguide can be visualized. This step can optionally be performed such that any other portion of the body, or bodily passageway, can be visualized. An optional step comprises confirming placement of the wireguide under MRI. This optional step can be accomplished by visualizing the wireguide, or a portion of the wireguide (e.g., segment, connector, spacer, marker), using the magnetic resonance scanner. For example, one or more markers (e.g., plurality of markers, distal tip marker) can be located using the magnetic resonance scanner (e.g., three views provided under MRI, axial, sagittal, and coronal) to determine the current location of the wireguide and/or distal tip within the bodily passageway. Another optional step comprises manipulating the position of the wireguide. This optional step can be accomplished by applying an axial force on the wireguide until the distal end, or a portion of the length, of the wireguide is positioned at, or near, a point of treatment and tracking movement of the wireguide under MRI (e.g., using continuous scans). Subsequently, an optional step comprises confirming placement of the wireguide using MRI. Another optional step comprises adjusting the image being received by the magnetic resonance scanner (e.g., adjusting set of sequences) such that a wireguide, or a portion of a wireguide, can be located under MRI.

Step 2206 can be accomplished by performing any suitable treatment. For example, treatments that utilize the wireguide to track another device into the bodily passageway, such as catheterization procedures and/or interventional cardiac procedures, can be accomplished using the wireguide. Optional steps comprise advancing a medical device into the bodily passageway and over the wireguide. Another optional step comprises advancing the medical device to a point of treatment. Another optional step comprises performing treatment using the medical device. Another optional step comprises removing the medical device from the bodily passageway. Each of these optional steps can optionally be accomplished concurrently with step 2204. In alternative embodiments, step 2206 can be omitted from method 2200. Optionally, step 2204, step 2206, and/or step 2208 can be accomplished while the magnetic resonance scanner is activated and creating an image (e.g., such that these steps, or any other step described herein, is being completed in real-time relative to the MRI image).

Step 2208 can be accomplished by applying an axial force on the wireguide away from the bodily passageway until the wireguide (e.g., wireguide distal end) is disposed outside of the bodily passageway. Optionally, this step can be performed concurrently with step 2204 such that visualization of the wireguide can be accomplished while advancing the wireguide out of the bodily passageway. An optional step comprises deactivating the magnetic resonance scanner.

Figure 100:
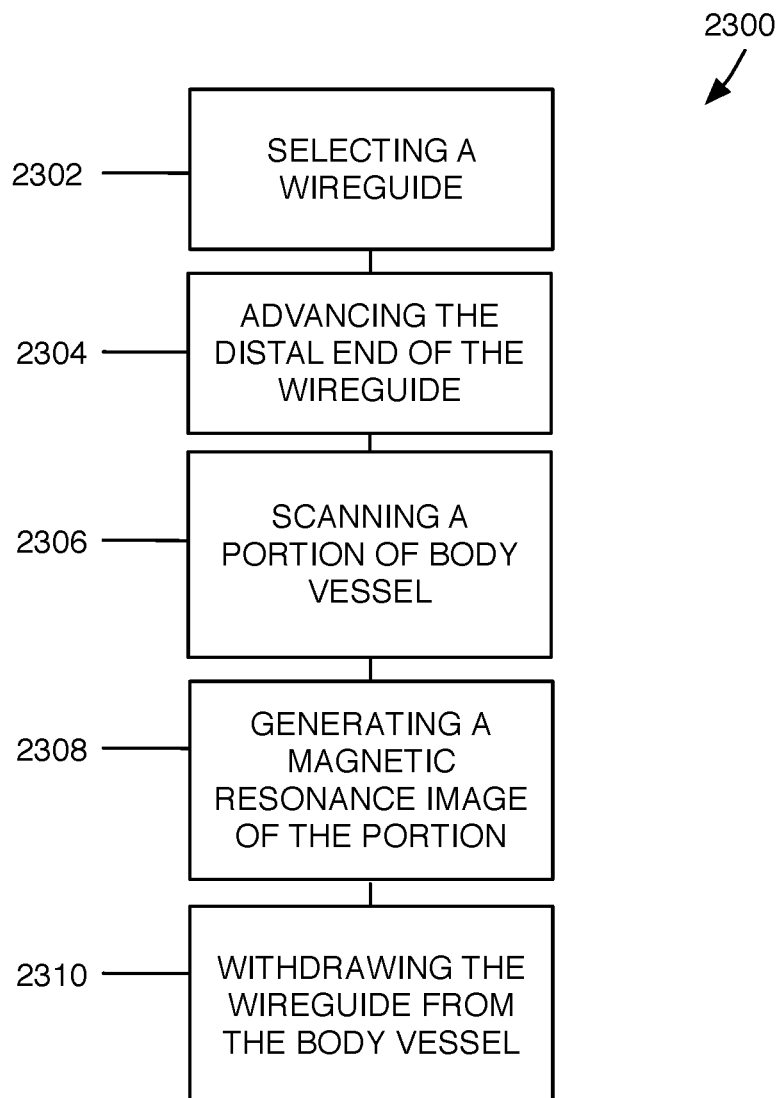
FIG. 100 is a schematic illustration of an example imaging method.

FIG. 100 is a schematic illustration of an example imaging method 2300. An initial step 2302 comprises selecting a wireguide having proximal and distal ends and comprising a marker. Another step 2304 comprises advancing the distal end of the wireguide to a first location within a body vessel of a patient and until the marker is disposed at a second location within the body vessel. Another step 2306 comprises scanning a portion of the body vessel that includes the first and second locations within the body vessel using a magnetic resonance scanner. Optionally, step 2306 can be accomplished concurrently with step 2304 and/or step 2310. Another step 2308 comprises obtaining a magnetic resonance image of the portion of the body vessel such that the image includes an artifact indicative of the presence of the marker within the portion of the body vessel. For this step 2308, a single still image can be obtained. Also, and optionally, this step 2308 can be repeated any desired number of times to obtain multiple magnetic resonance images that can be grouped as a cine to show motion. Another step 2310 comprises withdrawing the wireguide from the body vessel.

Figure 101:
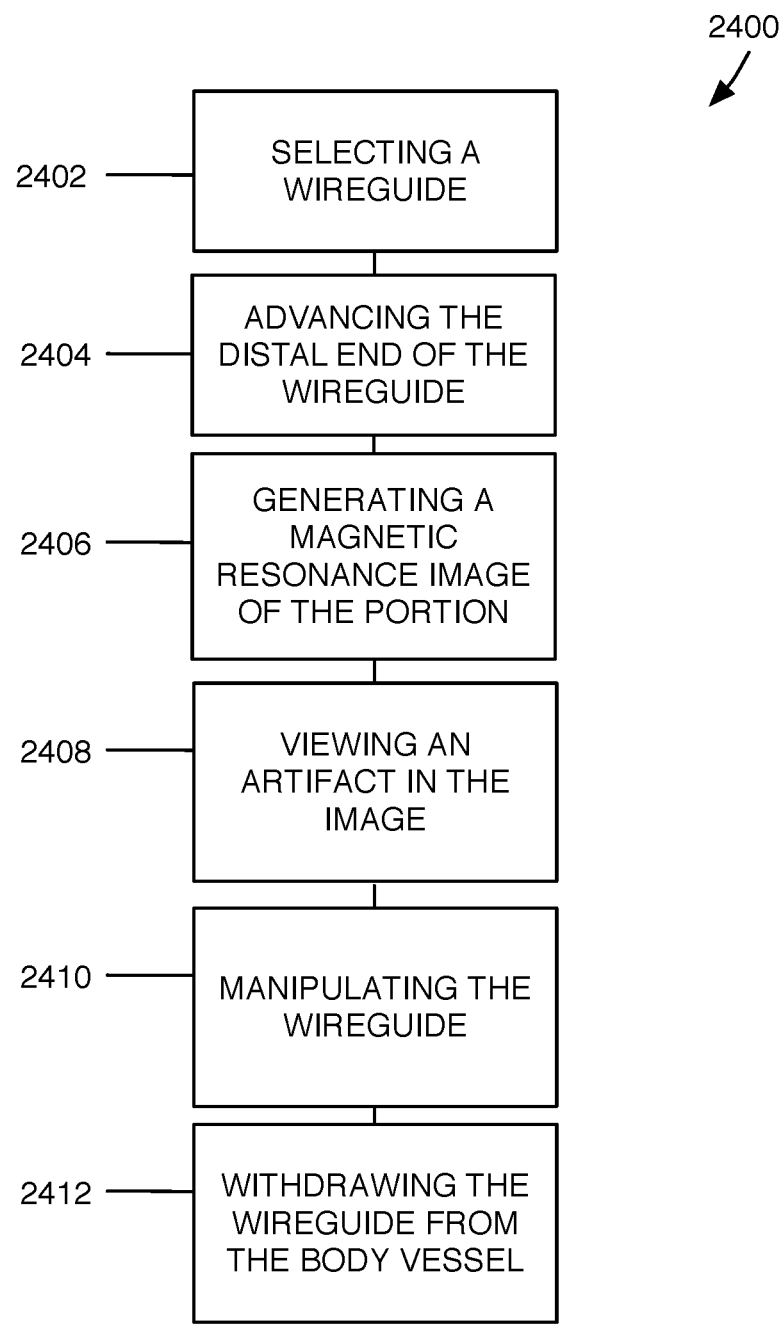
FIG. 101 is a schematic illustration of an example method of performing an interventional medical treatment.

FIG. 101 is a schematic illustration of an example method 2400 of performing an interventional medical treatment. An initial step 2402 comprises selecting a wireguide having proximal and distal ends and comprising a marker. Another step 2404 comprises advancing the distal end of the wireguide to a first location within a body vessel of a patient and until the marker is disposed at a second location within the body vessel. Another step 2406 comprises obtaining a magnetic resonance image of the portion of the body vessel while the marker is disposed at the second location within the body vessel. Optionally, step 2406 can be accomplished concurrently with step 2404, step 2408, step 2410, and/or step 2412. Another step 2408 comprises viewing an artifact in the image generated by the presence of the marker during the generating. Another step 2410 comprises manipulating the wireguide based on the location of the artifact relative to the body vessel. Another step 2412 comprises withdrawing the wireguide from the body vessel.

Figure 102:
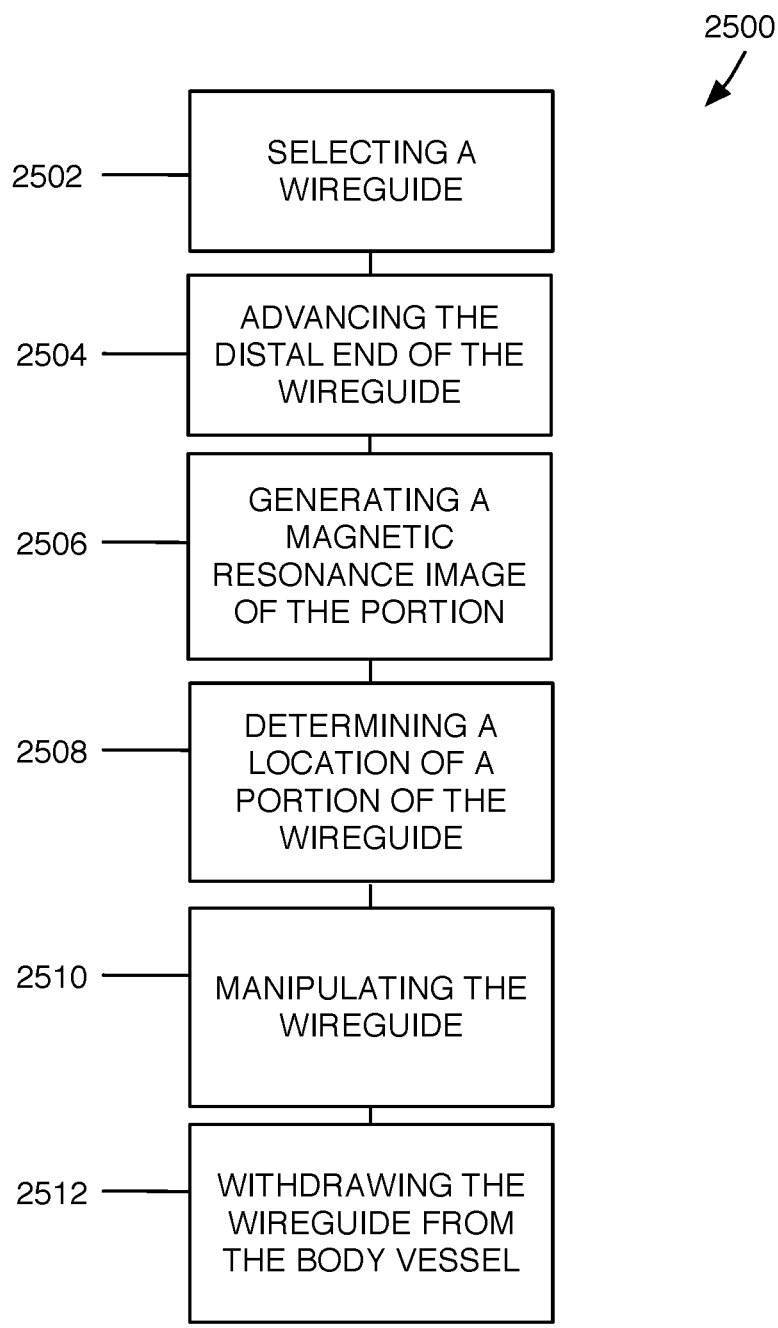
FIG. 102 is a schematic illustration of another example method of performing an interventional medical treatment.

FIG. 102 is a schematic illustration of an example method 2500 of performing an interventional medical treatment. An initial step 2502 comprises selecting a wireguide having proximal and distal ends and comprising a marker. Another step 2504 comprises advancing the distal end of the wireguide to a first location within a body vessel of a patient and until the marker is disposed at a second location within the body vessel. Another step 2506 comprises obtaining a magnetic resonance image of the portion of the body vessel while the marker is disposed at the second location within the body vessel. Optionally, step 2506 can be accomplished concurrently with step 2504, step 2508, step 2510, and/or step 2512. Another step 2508 comprises determining a location of a portion of the wireguide within the body vessel based at least partially on an artifact in the image generated by the presence of the marker during the generating. Another step 2510 comprises manipulating the wireguide within the body vessel. Another step 2512 comprises withdrawing the wireguide from the body vessel.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simply to describe and illustrate examples of the invention and are not intended to limit the scope of the invention or its protection, which is to be given the full breadth of the appended claims and any and all equivalents thereof.

What is claimed is:

1. A wireguide, comprising:
    a connector having a connector first end, a connector second end, and a circumferential wall defining a connector outer surface and a connector lumen extending between the connector first end and the connector second end, the connector defining a connector outer diameter;
    a first segment having a first segment first end, a first segment second end, a first segment body extending between the first segment first end and the first segment second end, a first segment end portion extending from the first segment second end to a location on the first segment body between the first segment first end and the first segment second end, and a first segment coating disposed on the first segment end portion, the first segment body having a first segment body outer surface and defining a first segment body outer diameter equal to the connector outer diameter, the first segment end portion defining a first segment end portion outer diameter that is less than the first segment body outer diameter and disposed in the connector lumen such that the connector outer surface is flush with the first segment body outer surface;
    a second segment having a second segment first end, a second segment second end, a second segment body extending between the second segment first end and the second segment second end, a second segment end portion extending from the second segment first end to a location on the second segment body between the second segment first end and the second segment second end, and a second segment coating disposed on the second segment end portion, the second segment body having a second segment body outer surface and defining a second segment body outer diameter equal to the connector outer diameter, the second segment end portion defining a second segment end portion outer diameter that is less than the second segment body outer diameter and disposed in the connector lumen such that the connector outer surface is flush with the second segment body outer surface; and
    a wireguide coating disposed over the first segment, the second segment, and the connector.

2. The wireguide of claim 1, further comprising a spacer disposed between the first segment second end and the second segment first end in the connector lumen.

3. The wireguide of claim 2, wherein the spacer comprises a polymeric material.

4. The wireguide of claim 1, wherein each of the first segment and the second segment comprises a nickel-titanium alloy.

5. The wireguide of claim 4, wherein the connector comprises a nickel-titanium alloy.

6. The wireguide of claim 1, wherein each of the first segment coating and the second segment coating comprises a polymeric material.

7. The wireguide of claim 6, wherein each of the first segment coating and the second segment coating comprises a polyimide.

8. The wireguide of claim 1, wherein the wireguide coating comprises a polymeric material.

9. The wireguide of claim 1, further comprising a marker disposed on one of the first segment and the second segment; and
    wherein the marker comprises a material that is visible under MRI.

10. The wireguide of claim 1, wherein the first segment end portion defines a first tapered portion.

11. The wireguide of claim 10, wherein the first tapered portion has a first tapered portion first outside diameter at the first segment second end and a first tapered portion second outside diameter between the first segment second end the first segment body.

12. The wireguide of claim 11, wherein the first tapered portion first outside diameter is greater than the first tapered portion second outside diameter.

13. The wireguide of claim 12, wherein the second segment end portion defines a second tapered portion.

14. The wireguide of claim 13, wherein the second tapered portion has a second tapered portion first outside diameter at the second segment first end and a first tapered portion second outside diameter between the second segment first end the second segment body.

15. The wireguide of claim 14, wherein the second tapered portion first outside diameter is greater than the second tapered portion second outside diameter.

16. A wireguide, comprising:
    a connector having a connector first end, a connector second end, and a circumferential wall defining a connector outer surface and a connector lumen extending between the connector first end and the connector second end;
    a first coated segment having a first main body defining a first segment outer surface and first and second tapered portions, the second tapered portion disposed in the connector lumen such that the connector outer surface is flush with the first segment outer surface;
    a second coated segment having a second main body defining a second segment outer surface and third and fourth tapered portions, the third tapered portion disposed in the connector lumen such that the connector outer surface is flush with the second segment outer surface; and
    a wireguide coating disposed over the first coated segment, the second coated segment, and the connector.

17. The wireguide of claim 16, further comprising a spacer disposed between the second tapered end and the third tapered end in the connector lumen.

18. The wireguide of claim 16, wherein each of the first segment and the second segment comprises a nickel-titanium alloy.

19. The wireguide of claim 18, wherein the connector comprises a nickel-titanium alloy.

20. A wireguide, comprising:
    a connector having a connector first end, a connector second end, and a circumferential wall defining a connector outer surface and a connector lumen extending between the connector first end and the connector second end;

a first coated segment having a first main body defining a first segment outer surface, a first end, a second end, a first tapered portion including the first end, and a second tapered portion including the second end, the first main body defining a first outer diameter between the first and second tapered portions and a second outer diameter at the second end that is less than the first outer diameter, the second tapered portion disposed in the connector lumen such that the connector outer surface is flush with the first segment outer surface;

a second coated segment having a second main body defining a second segment outer surface, a third end, a fourth end, a third tapered portion including the third end, and a fourth tapered portion including the fourth end, the second main body defining a third outer diameter between the third and fourth tapered portions and a fourth outer diameter at the third end that is less than the third outer diameter, the third tapered portion disposed in the connector lumen such that the connector outer surface is flush with the second segment outer surface; and a wireguide coating disposed over the first coated segment, the second coated segment, and the connector;

wherein the first outer diameter and the third outer diameter are equal; and wherein the second outer diameter and the fourth outer diameter are equal.

* * * * *

UNITED STATES PATENT AND TRADEMARK OFFICE
CERTIFICATE OF CORRECTION

| | | |
|---|---|---|
| PATENT NO. | : 11,724,073 B2 | Page 1 of 1 |
| APPLICATION NO. | : 17/539683 | |
| DATED | : August 15, 2023 | |
| INVENTOR(S) | : Ram H Paul, Jr. et al. | |

It is certified that error appears in the above-identified patent and that said Letters Patent is hereby corrected as shown below:

In the Specification

Column 1, please add after Line 11:
--GOVERNMENT LICENSE RIGHTS
This invention was created in the performance of a Cooperative Research and Development Agreement with the National Institutes of Health, an Agency of the Department of Health and Human Services. The Government of the United States has certain rights in this invention.--

Signed and Sealed this
Fifteenth Day of April, 2025

Coke Morgan Stewart
*Acting Director of the United States Patent and Trademark Office*